US012699099B2

(12) United States Patent
Mallick

(10) Patent No.: US 12,699,099 B2
(45) Date of Patent: Aug. 4, 2026

(54) METHODS AND APPLICATIONS OF PROTEIN IDENTIFICATION

(71) Applicant: NAUTILUS SUBSIDIARY, INC., Seattle, WA (US)

(72) Inventor: Parag Mallick, San Mateo, CA (US)

(73) Assignee: NAUTILUS SUBSIDIARY, INC., Seattle, WA (US)

( * ) Notice: Subject to any disclaimer, the term of this patent is extended or adjusted under 35 U.S.C. 154(b) by 1185 days.

(21) Appl. No.: 16/972,341

(22) PCT Filed: Jun. 5, 2019

(86) PCT No.: PCT/US2019/035654
§ 371 (c)(1),
(2) Date: Dec. 4, 2020

(87) PCT Pub. No.: WO2019/236749
PCT Pub. Date: Dec. 12, 2019

(65) Prior Publication Data
US 2021/0239705 A1 Aug. 5, 2021

Related U.S. Application Data

(60) Provisional application No. 62/681,644, filed on Jun. 6, 2018.

(51) Int. Cl.
*G01N 33/68* (2006.01)
*G01N 33/58* (2006.01)

(52) U.S. Cl.
CPC ....... *G01N 33/6842* (2013.01); *G01N 33/582* (2013.01)

(58) Field of Classification Search
CPC ............. G01N 33/6842; G01N 33/582; G01N 33/54306; G01N 33/6803; G01N 33/5014;
(Continued)

(56) References Cited

U.S. PATENT DOCUMENTS 5,445,934 A 8/1995 Fodor et al.
5,849,878 A 12/1998 Cantor et al.
(Continued)

FOREIGN PATENT DOCUMENTS

CN 100500865 C 6/2009
EP 2872898 B1 12/2016
(Continued)

OTHER PUBLICATIONS 44, 47-49 & 63-66 is/are rejected under 35 U.S.C. 103 as being obvious by Nielsen in Profiling receptor tyrosine kinase activation by using Ab microarrays. 2003. (Year: 2003).*
(Continued)

*Primary Examiner* — Rebecca M Fritchman

(74) *Attorney, Agent, or Firm* — Knobbe, Martens, Olson & Bear LLP

(57) ABSTRACT

Methods and systems for identifying a protein within a sample are provided herein. A panel of antibodies are acquired, none of which are specific for a single protein or family of proteins. Additionally, the binding properties of the antibodies in the panel are determined. Further, the protein is iteratively exposed to a panel of antibodies. Additionally, a set of antibodies which bind the protein are determined. The identity of the protein is determined using one or more deconvolution methods based on the known binding properties of the antibodies to match the set of antibodies to a sequence of a protein.

17 Claims, 19 Drawing Sheets

(58) Field of Classification Search

CPC ............ G01N 33/5067; G01N 33/5088; C40B 30/04; A61K 35/407; C12N 15/86; C12N 15/907; C12N 2310/20; C12N 2501/15; C12N 2501/727; C12N 2506/45; C12N 2740/15043; C12N 2800/80; C12N 15/1137; C12N 2310/16; C12N 2310/3519; C12N 2320/11; C12N 2501/60; C12N 2510/00; C12N 2740/16043

See application file for complete search history.

(56)                References Cited

U.S. PATENT DOCUMENTS

| | | | |
|---|---|---|---|
| 6,720,595 | B2 | 4/2004 | Clevenger et al. |
| 6,998,241 | B2 | 2/2006 | Boga |
| 7,252,954 | B2 | 8/2007 | Wang et al. |
| 7,842,793 | B2 | 11/2010 | Rothemund |
| 7,932,060 | B2 | 4/2011 | Nadeau et al. |
| 8,501,923 | B2 | 8/2013 | Rothemund |
| 9,340,416 | B2 | 5/2016 | Maune et al. |
| 9,528,984 | B2 | 12/2016 | Mitra |
| 9,880,175 | B2 | 1/2018 | Mitra |
| 10,175,248 | B2 | 1/2019 | Mitra |
| 10,351,909 | B2 | 7/2019 | Drmanac et al. |
| 10,473,654 | B1 | 11/2019 | Mallick |
| 10,571,473 | B2 | 2/2020 | Mitra |
| 10,741,382 | B2 | 8/2020 | Sills et al. |
| 10,829,816 | B2 | 11/2020 | Staker et al. |
| 10,921,317 | B2 | 2/2021 | Mallick |
| 10,948,488 | B2 | 3/2021 | Mallick |
| 2003/0054408 | A1* | 3/2003 | Ravi ...................... G16B 20/50 |
| | | | 435/7.1 |
| 2004/0023413 | A1 | 2/2004 | Opalsky |
| 2004/0091931 | A1 | 5/2004 | Gold |
| 2004/0166106 | A1 | 8/2004 | Wang et al. |
| 2006/0160234 | A1 | 7/2006 | Lopez-Avila et al. |
| 2006/0263769 | A1 | 11/2006 | Luo et al. |
| 2007/0188750 | A1 | 8/2007 | Lundquist et al. |
| 2007/0218503 | A1 | 9/2007 | Mitra |
| 2009/0214591 | A1 | 8/2009 | Manucharyan et al. |
| 2011/0065807 | A1 | 3/2011 | Radovic-Moreno et al. |
| 2011/0263688 | A1 | 10/2011 | Barany et al. |
| 2012/0077688 | A1 | 3/2012 | Bergo et al. |
| 2014/0274782 | A1* | 9/2014 | Carlson .............. C07K 14/4702 |
| | | | 435/352 |
| 2015/0160204 | A1 | 6/2015 | Mitra |
| 2015/0185199 | A1 | 7/2015 | Joo et al. |
| 2015/0330974 | A1 | 11/2015 | Staker et al. |
| 2016/0102344 | A1 | 4/2016 | Niemeyer et al. |
| 2016/0310926 | A1 | 10/2016 | Sun et al. |
| 2017/0044245 | A1 | 2/2017 | Meng et al. |
| 2017/0175184 | A1 | 6/2017 | Drmanac et al. |
| 2017/0191051 | A1 | 7/2017 | Nikiforov |
| 2017/0283868 | A1 | 10/2017 | Beechem et al. |
| 2019/0204339 | A1 | 7/2019 | Mitra |
| 2020/0025752 | A1 | 1/2020 | Gopinath et al. |
| 2020/0025757 | A1 | 1/2020 | Gopinath et al. |
| 2020/0158722 | A1 | 5/2020 | Mallick |
| 2020/0173988 | A1 | 6/2020 | Mallick |
| 2020/0232994 | A1 | 7/2020 | Mitra |
| 2020/0318101 | A1 | 10/2020 | Mallick et al. |
| 2021/0223238 | A1 | 7/2021 | Mallick |
| 2021/0355483 | A1* | 11/2021 | Chee ...................... G01N 33/68 |

FOREIGN PATENT DOCUMENTS

| | | | |
|---|---|---|---|
| WO | WO-02086081 | A2 | 10/2002 |
| WO | WO-2006135527 | A2 | 12/2006 |
| WO | WO-2007117444 | A2 | 10/2007 |
| WO | WO-2010065531 | A1 | 6/2010 |
| WO | WO-2014078855 | A1 | 5/2014 |
| WO | WO-2015097077 | A2 | 7/2015 |
| WO | WO-2016174525 | A1 | 11/2016 |
| WO | WO-2017127762 | A1 | 7/2017 |
| WO | WO-2018102759 | A1 | 6/2018 |
| WO | WO-2019036055 | A2 | 2/2019 |
| WO | WO-2019195633 | | 10/2019 |
| WO | WO-2019236749 | A2 | 12/2019 |
| WO | WO-2020106889 | A1 | 5/2020 |
| WO | WO-2020223368 | A1 | 11/2020 |

OTHER PUBLICATIONS

Ayoglu, et al., Autoantibody Profiling in Multiple Sclerosis Using Arrays of Human Protein Fragments, Molecular & Cellular Proteomics, (12)9 Sep. 1, 2013 (Sep. 1, 2013), pp. 2657-2672, XP055294116, US , ISSN: 1535-9476, DOI: 10.1074/mcp.M112.026757.

Choung, et al. Determination of B-Cell Epitopes in Patients with Celiac Disease: Peptide Microarrays. PloS one vol. 11(1) e0147777. Jan. 29, 2016, doi:10.1371/journal.pone.0147777.

Co-pending U.S. Appl. No. 17/390,666, inventor Mallick; Parag, filed Jul. 30, 2021.

Co-pending U.S. Appl. No. 17/424,435, inventors Klein; Joshua et al., filed Jul. 20, 2021.

Co-pending U.S. Appl. No. 17/496,742, inventors Gremyachinskiy; Dmitriy et al., filed Oct. 7, 2021.

EP18846671.8 Extended European Search Report dated Apr. 23, 2021.

Fodor, et al. Light-Directed, Spatially Addressable Parallel Chemical Synthesis. Science , vol. 251, 767-773, 1991.

Kang, H. The prevention and handling of the missing data. Korean journal of anesthesiology vol. 64,5 (2013): 402-6. doi:10.4097/kjae.2013.64.5.402.

Laurenson, et al. Development of peptide aptamer microarrays for detection of HPV16oncoproteins in cell extracts, Analytical Biochemistry, Academic Press, Amsterdam, NL, vol. 410, No. 2, Oct. 30, 2010 (Oct. 30, 2010), pp. 161-170, XP028146256,ISSN: 0003-2697,DOI: 10.1016/J.AB.2010.10.038.

Lin et al. Development of a novel peptide microarray for large-scale epitope mapping of food allergens, Journal of Allergy and Clinical Immunology, Elsevier, Amsterdam, NL, vol. 124, No. 2, Aug. 1, 2009 (Aug. 1, 2009), pp. 315-322.e3, XP026390934, ISSN: 0091-6749,DOI: 10.1016/J.JACI.2009.05.024.

Nonobe et al. A tabu search approach to the constraint satisfaction problem as a general problem solver. Eur. J. Oper. Res. 106 (1998): 599-623.

Price, et al., On silica peptide microarrays for high-resolution mapping of antibody epitopes and diverse protein-protein interactions, Nature Medicine, vol. 18, No. 9, Aug. 19, 2012, pp. 1434-1440, XP055793803, New York ISSN: 1078-8956, DOI: 10.1038/nm.2913Retrieved from the Internet:URL:http://www.nature.com/articles/nm.2913.

Reineke, et al. Epitope mapping protocols. Preface. Methods in molecular biology (Clifton, N.J.) vol. 524 (2009): v-vi.

Riccelli, et al. Hybridization of single-stranded DNA targets to immobilized complementary DNA probes: comparison of hairpin versus linear capture probes. Nucleic acids research vol. 29,4 (2001): 996-1004. doi:10.1093/nar/29.4.996.

Richer, et al., Epitope identification from fixed-complexity random-sequence peptide microarrays, Molecular & cellular proteomics, vol. 14, No. 1, Nov. 3, 2014, pp. 136-147.

Rothemund, et al. Folding DNA to create nanoscale shapes and patterns. Nature. Mar. 16, 2006;440(7082):297-302.

Sjoberg et al. Validation of affinity reagents using antigen microarrays, Newbiotechnology, vol. 29, No. 5, Jun. 1, 2012 pp. 555-563, XP055793929,Nlissn: 1871-6784, DOI: 10.1016/j.nbt.2011.11.009.

Tessler, L. Digital Protein Analysis: Technologies for Protein Diagnostics and Proteomics through Single-Molecule Detection (2011). All Theses and Dissertations (ETDs). 346 https://openscholarship.wustl.edu/etd/346.

U.S. Appl. No. 16/791,456 Office Action dated Jul. 6, 2021.

U.S. Appl. No. 17/062,405 Final Office Action dated Aug. 24, 2021.

U.S. Appl. No. 17/062,405 Notice of Allowance dated Sep. 30, 2021.

U.S. Appl. No. 17/062,405 Office Action dated Apr. 14, 2021.

(56) References Cited

OTHER PUBLICATIONS

U.S. Appl. No. 17/191,632 Examiner's Interview Summary dated Nov. 9, 2021.
U.S. Appl. No. 17/191,632 Final Office Action dated Sep. 17, 2021.
U.S. Appl. No. 17/191,632 Office Action dated May 12, 2021.
Zandian, Arash et al. Whole-Proteome Peptide Microarrays for Profiling Autoantibody Repertoires within Multiple Sclerosis and Narcolepsy. Journal of proteome research 16(3) 2017: 1300-1314.
3-Aminopropyl)triethoxysilane. Wikipedia.org. Apr. 5, 2019 (Apr. 5, 2019), entire document esp p. 1 (https://en.wikipedia.org/w/index.php?title=(3- Aminopropyl)triethoxysilaneoldid&oldid=891131780).
Arnold et al. "The majority of immunogenic epitopes generate CD44-T cells that are dependent on MHC class II-bound peptide-flanking residues," J Immunol, Jul. 15, 2002 (Jul. 15, 2002), vol. 169, No. 2, pp. 739-749.
Blatch, et al. The tetratricopeptide repeat: a structural motif mediating protein-protein interactions. Bioessays Nov. 1999;21 (11):932-939.
Buenrostro, et al. Quantitative analysis of RNA-protein interactions on a massively parallel array for mapping biophysical and evolutionary landscapes. Nat Biotechnol. Jun. 2014; 32(6): 562-568.
Bunka et al. "Production and characterization of RNA aptamers specific for amyloid fibril epitopes," J Biol Chem, Sep. 18, 2007 (Sep. 18, 2007), vol. 282, No. 47, pp. 34500-34509.
Buus, et al. High-resolution mapping of linear antibody epitopes using ultrahigh-density peptide microarrays.Molecular & Cellular Proteomics 11.12 (2012): 1790-1800.
Co-pending U.S. Appl. No. 17/062,405, inventors Gremyachinskiy; Dmitriy et al., filed Oct. 2, 2020.
Co-pending U.S. Appl. No. 17/153,877, inventor Mallick; Parag, filed Jan. 20, 2021.
Domenyuk, et al. Plasma Exosome Profiling of Cancer Patients by a Next Generation Systems Biology Approach. Sci Rep. 2017; 7: 42741.
EP17877076.4 The Extended European Search Report dated Aug. 11, 2020.
Ford et al. "Degenerate recognition of T cell epitopes: impact of T cell receptor reserve and stability of peptide:MHC complexes," Mol Immunol, Feb. 1, 2004 (Feb. 1, 2004), vol. 40, No. 14-15, pp. 1019-1025.
Hung, et al. Large-area spatially ordered arrays of gold nanoparticles directed by lithographically confined DNA origami. Nat Nanotechnol. Feb. 2010;5(2):121-6. doi: 10.1038/nnano.2009.450. Epub Dec. 20, 2009.
Hunniger, et al. Just in time-selection: A rapid semiautomated SELEX of DNA aptamers using magnetic separation and BEAM-ing. Anal Chem. Nov. 4, 2014;86(21):10940-7.

Lutz, et al. Efficient construction of therapeutics, bioconjugates, biomaterials and bioactive surfaces using azide-alkyne "click" chemistry. Adv Drug Deliv Rev. Jun. 10, 2008;60(9):958-70. doi: 10.1016/j.addr.2008.02.004. Epub Mar. 4, 2008.
Mckay, et al. Click Chemistry in Complex Mixtures: Bioorthogonal Bioconjugation. Chem Biol. Sep. 18, 2014; 21(9): 1075-1101.
Meldal, et al. Cu-catalyzed azide-alkyne cycloaddition. Chem Rev. Aug. 2008; 108(8):2952-3015. doi: 10.1021/cr0783479.
Patronov et al. "Peptide binding prediction for the human class II MHC allele HLA-DP2: a molecular docking approach," BMC Struct Biol, Jul. 14, 2011 (Jul. 14, 2011), vol. 11, No. 32, pp. 1-10.
PCT/US17/64322 International Search Report and Written Opinion dated Apr. 25, 2018.
PCT/US18/00364 International Search Report and Written Opinion dated Mar. 22, 2019.
PCT/US2019/025909 International Search Report and Written Opinion dated Jun. 14, 2019.
PCT/US2019/035654 International Search Report dated Nov. 25, 2019.
PCT/US2019/062482 International Search Report dated Mar. 3, 2020.
PCT/US2020/030501 International Search Report dated Aug. 11, 2020.
Reyes et al. "Critical role of HLA-DR11" binding peptides' peripheral flanking residues in fully-protective malaria vaccine development, Biochem Biophys Res Commun, May 23, 2017 (May 23, 2017), vol. 489, No. 3, pp. 339-345.
Sant'Angelo et al. "Recognition of core and flanking amino acids of MHC class II-bound peptides by the T cell receptor," Eur J Immunol, Sep. 1, 2002 (Sep. 1, 2002), vol. 32, No. 9, pp. 2510-2520.
She, et al. Comprehensive and quantitative mapping of RNA-protein interactions across a transcribed eukaryotic genome. Proc Natl Acad Sci U S A. Apr. 4, 2017; 114(14): 3619-3624.
Speltz, et al. Design of Protein-Peptide Interaction Modules for Assembling Supramolecular Structures in Vivo and in Vitro. ACS Chem Biol. Sep. 18, 2015;10(9):2108-15. doi: 10.1021/acschembio.5b00415. Epub Jul. 17, 2015.
Stöhr, et al. A 31-residue peptide induces aggregation of tau's microtubule-binding region in cells. Nat Chem. Sep. 2017; 9(9): 874-881. Published online Apr. 3, 2017.doi: 10.1038/nchem.2754.
U.S. Appl. No. 16/659,132 Notice of Allowance dated Jan. 14, 2021.
U.S. Appl. No. 16/659,132 Office Action dated Oct. 8, 2020.
U.S. Appl. No. 16/788,536 Notice of Allowance dated Dec. 9, 2020.
U.S. Appl. No. 16/788,536 Office Action dated Mar. 10, 2020.
U.S. Appl. No. 16/788,536 Office Action dated Sep. 24, 2020.
U.S. Appl. No. 16/426,917 Notice of Allowance dated Oct. 1, 2019.
Wilson, et al. Single-Step Selection of Bivalent Aptamers Validated by Comparison with SELEX Using High-Throughput Sequencing. PLoS One. 2014; 9(6): e100572.

* cited by examiner

Protein Sample

Protein Quantification by multiaffinity probe Decoding

Protein Sample

FIG. 7

Protein Identification/Quantification by Multiaffinity probe Decoding

Whole proteome quantification: counts for all proteins

| Protein | #Mol | #multiaffinity probe_hits |
|---|---|---|
| Protein 1 | 106 | 10 |
| Protein 2 | 832 | 6 |
| Protein 3 | $1.6 \times 10^6$ | 30 |
| ... | | |
| Protein 25K | 1 | 22 |

FIG. 11 anomaly list: likely mutant and modified proteins

| Location | LikelyProtein | extra hits |
|---|---|---|
| Spot 1, 2 | Protein1 | TRT, Y', ... |
| Spot 12, 36 | Protein2 | RBM, ... |
| ... | | |

FIG. 12

Fluorescence Imaging of Single Protein Molecules

FIG. 16A

Identifying A Protein

>sp|P42212|GFP_AEQVI Green fluorescent protein OS=Aequorea victoria GN=GFP PE=1 SV=1 6-HIS
MSKGEELFTGVVPILVELDGDVNGHKFSVSGEGEGDATYGKLTLKFICTTGKLPVPWPTLVTTFSYGVQCFSRYPDHMKQHDFFKSAMPEGYVQER
TIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGP
VLLPDNHYLSTQSALSKDPNEKRDHMVLLEFVTAAGITHGMDELYKHHHHHH >sp|P61823|RNAS1_BOVIN Ribonuclease pancreatic OS=Bos taurus GN=RNASE1 PE=1 SV=1
MALKSLVLLSLLVLVLLLVRVQPSLGKETAAAKFERQHMDSSTSAASSNYCNQMKSRNLTKDRCKPVNTFVHESLADVQAVCSQKNVACKNGQT
NCYQSYSTMSITDCRETGSSKYPNCAYKTTQANKHIIVACEGNPYVPVHFDASV >sp|P02788|TRFL_HUMAN Lactotransferrin OS=Homo sapiens GN=LTF PE=1 SV=6
MKLVFLVLLFLGALGLCLAGRRRSVQWCAVSQPEATKCFQWQRNMRKVRGPPVSCIKRDSPIQCIQAIAENRADAVTLDGGFIYEAGLAPYKLRPV
AAEVYGTERQPRTHYYAVAVVKKGGSFQLNELQGLKSCHTGLRRTAGWNVPIGTLRPFLNWTGPPEPIEAAVARFFSASCVPGADKGQFPNLCRLC
AGTGENKCAFSSQEPYFSYSGAFKCLRDGAGDVAFIRESTVFEDLSDEAERDEYELLCPDNTRKPVDKFKDCHLARVPSHAVVARSVNGKEDAIWN
LLRQAQEKFGKDKSPKFQLFGSPSGQKDLLFKDSAIGFSRVPPRIDSGLYLGSGYFTAIQNLRKSEEVAARRARVVWCAVGEQELRKCNQWSGLS
EGSVTCSSASTTEDCIALVLKGEADAMSLDGGYVYTAGKCGLVPVLAENYKSQQSSDPDPNCVDRPVEGYLAVAVVRRSDTSLITWNSVKGKKSCHT
AVDRTAGWNIPMGLLFNQTGSCKFDEYFSQSCAPGSDPRSNLCALCIGDEQGENKCVPNSNERYYGYTGAFRCLAENAGDVAFVKDVTVLQNTDGN
NNEAWAKDLKLADFALLCLDGKRKPVTEARSCHLAMAPNHAVVSRMDKVERLKQVLLHQQAKFGRNGSDCPDKFCLFQSETKNLLFNDNTECLARL
HGKTTYEKYLGPQYVAGITNLKKCSTSPLLEACEFLRK >tr|C1L9P1|C1L9P1_SCHJA Glutathione S-transferase M1 OS=Schistosoma japonicum GN=GSTM1 PE=2 SV=1
HIS-V5-GSTM1 CAX71422 SjCD00671637
STMSPILGYWKIKGLVQPTRLLLEYLEEKYEEHLYERDEGDKWRNKFELGLEFPNLPYIDGDVKLTQSMAIIRYIADKHNMLGGCPKERAEISM
LEGAVLDIRYGVSRIAYSKDFETLKVDFLSKLPEMLKMFEDRLCHKTYLNGDHVTHPDFMLYDALDVVLYMDPMCLDAFPKLVCFKKRIEAIPQID
KYLKSSKYIAWPLQGWQATFGGGDHPFKSDLVPRGSPLEVLFQGPCGSYGS

FIG. 18

METHODS AND APPLICATIONS OF PROTEIN IDENTIFICATION

CROSS-REFERENCE

This application is a national stage entry of International Patent Application No. PCT/US2019/035654, filed Jun. 5, 2019, which claims the benefit of U.S. Provisional Patent Application No. 62/681,644, filed Jun. 6, 2018, entitled METHODS AND APPLICATIONS OF PROTEIN IDEN-TIFICATION, each of which is entirely incorporated herein by reference.

BACKGROUND OF THE INVENTION

Current techniques for protein identification typically rely upon either the binding and subsequent readout of highly specific and sensitive antibodies or upon peptide-read data (typically on the order of 12-30 AA long) from a mass spectrometer.

SUMMARY OF THE INVENTION

The present disclosure provides methods and systems for assaying proteins. In some embodiments, the present dis-closure provides approaches in which the identities of pro-teins, i.e. their sequence, in a mixture are inferred from a series of measurements that may be highly incomplete and/or are not specific to a particular protein. Methods and systems described herein may also be used to characterize and/or identify biopolymers, including proteins. Addition-ally, methods and systems described herein may be used to identify proteins more quickly than techniques for protein identification that rely upon data from a mass spectrometer. In some examples, methods and systems described herein may be used to identify at least 400 different proteins with at least 50% accuracy at least 10% more quickly than techniques for protein identification that rely upon data from a mass spectrometer. In some examples, methods and sys-tems described herein may be used to identify at least 1000 different proteins with at least 50% accuracy at least 10% more quickly than techniques for protein identification that rely upon data from a mass spectrometer.

An aspect of the invention provides a method of deter-mining protein characteristics. The method comprises obtaining a substrate with portions of one or more proteins conjugated to the substrate such that each individual protein molecule has a unique, resolvable, spatial address. In some cases, each individual protein molecule may have a unique, optically resolvable, spatial address. The method further comprises applying a fluid containing a first through nth set of one or more affinity reagents to the substrate. In some embodiments, the affinity reagents may contain or be coupled to an identifiable tag. After each application of the first through nth set of one or more of affinity reagents to the substrate, the method comprises performing the following steps: observing the affinity reagent or identifiable tag; identifying one or more unique spatial addresses of the substrate having one or more observed signal; and deter-mining that each portion of the one or more proteins having an identified unique spatial address contains the one or more epitopes associated with the one or more observed signals. In some instances, each of the conjugated portions of the one or more proteins is associated with a unique spatial address on the substrate. In some instances, each affinity reagent of the first through nth set of one or more affinity reagents is not specific to an individual protein or protein family. In some instances, the binding epitope of the affinity reagent is not known or specific to an individual protein or protein family.

In some cases, the methods of this disclosure may also be used with a substrate which has multiple proteins bound in a single location, wherein at least about 50%, 60%, 70%, 80%, 90%, or more than 90% of the proteins at a single location comprise a common amino acid sequence. In some cases, the methods of this disclosure may also be used with a substrate which has multiple proteins bound in a single location, wherein at least about 50%, 60%, 70%, 80%, 90%, or more than 90% of the proteins at a single location comprise at least 95% amino acid sequence identity.

In some embodiments, the one or more proteins may comprise one single protein molecule. In some embodi-ments, the one or more proteins may comprise bulk proteins. In some embodiments, the one or more proteins may com-prise a plurality of a same protein that is conjugated at a same unique spatial address on the substrate.

In some embodiments, each affinity reagent of the first through nth set of one or more affinity reagents recognizes a family of one or more epitopes that are present in more than one proteins. In some embodiments, the method further comprises determining the identity of the portion of the one or more proteins to a threshold degree of accuracy based on the determined one or more epitopes within the portion. In some instances, the first through nth set of one or more affinity reagents comprises more than 100 affinity reagents. In some embodiments the method further comprises the use of affinity reagents which bind a single protein or single protein isoform.

In some embodiments, the method further comprises determining the identity of the portion of the one or more proteins to a threshold degree of accuracy based on the pattern of binding of the affinity reagents. In some instances the substrate is a flow cell. In some instances, the portions of one or more proteins are conjugated to the substrate using a photo-activatable linker. In some instances, the portions of one or more proteins are conjugated to the substrate using a photo-cleavable linker.

In some instances, at least a portion of the at least one set of affinity reagents is modified to be conjugated to an identifiable tag. In some instances the identifiable tag is a fluorescent tag. In some instances the identifiable tag is a magnetic tag. In some instances an identifiable tag is a nucleic acid barcode. In some instances an identifiable tag is an affinity tag (e.g. Biotin, Flag, myc). In some instances, the number of spatial addresses occupied by an identified por-tion of a protein is counted to quantify the level of that protein in the sample. In some instances, the identity of the portion of the one or more proteins is determined using deconvolution software. In some instances, the identity of the portion of the one or more proteins is determined by decoding combinations of epitopes associated with unique spatial addresses. In some instances, the method further comprises denaturing the one or more proteins prior to conjugating the portions of the one or more proteins to the substrate. In some instances, the portions of one or more proteins to a substrate are present in a complex mixture of multiple proteins. In some instances, the method is used to identify multiple proteins.

An additional aspect of the invention provides a method of identifying a protein comprising: acquiring a panel of affinity reagents none of which are specific for a single protein or family of proteins, determining the binding prop-erties of the antibodies in the panel, iteratively exposing the protein to the panel of antibodies, determining a set of the antibodies which bind the protein, and using one or more deconvolution methods based on the known binding properties of the antibodies to match the set of antibodies to a sequence of a protein, thereby determining the identity of the protein. In some instances, the protein to be identified is identified within a sample containing multiple different proteins. In some instances, the method is able to simultaneously identify multiple proteins within a single sample.

Another aspect of the invention provides a method of identifying a protein. The method comprises acquiring a panel of antibodies none of which are specific for a single protein or family of proteins, determining the binding properties of the antibodies in the panel, iteratively exposing the protein to the panel of antibodies, determining a set of the antibodies which do not bind the protein, and using one or more deconvolution methods based on the known binding properties of the antibodies to match the set of antibodies to a sequence of a protein, thereby determining the identity of the protein.

Another aspect of the invention provides a method of uniquely identifying and quantifying n proteins in a mixture of proteins using m affinity reagents, wherein n is larger than m, and n and m are positive integers greater than 1, and wherein the proteins have not been separated by an intrinsic property. In some instances, n is approximately 5, 10, 20, 50, 100, 500, 1,000, 5,000, or 10,000 times larger than m.

Another aspect of the invention provides a method of uniquely identifying and quantifying n proteins in a mixture of proteins using m binding reagents, wherein n is larger than m, and wherein the proteins are randomly arranged. In some instances, the proteins have not been separated by a size based, or charge based, separation method.

Another aspect of the invention provides a method of uniquely identifying and quantifying n single protein molecules in a mixture of protein molecules using m affinity reagents. The method further comprises that n is larger than m, and that the single protein molecules are conjugated to a substrate and spatially separated such that each individual protein molecule has a unique, optically resolvable, spatial address.

Another aspect of the invention provides a method to identify, with certainty above a threshold amount, an unknown single protein molecule from a pool of n possible proteins. The method comprises using a panel of affinity reagents, wherein the number of affinity reagents in the panel is m, and wherein m is less than one tenth of n.

Another aspect of the invention provides a method to select a panel of m affinity reagents capable of identifying an unknown protein selected from a pool of n possible proteins, wherein m is less than n−1.

Another aspect of the invention provides a method to select a panel of m affinity reagents capable of identifying an unknown protein selected from a pool of n possible proteins, wherein m is less than one tenth of n.

Another aspect of the invention provides a method to select a panel of less than 4000 affinity reagents, such that the panel of less than 4000 affinity reagents is capable of uniquely identifying each of 20,000 different proteins. In some embodiments, an affinity reagent may comprise a group of different components. In some embodiments, each component within an affinity reagent may share a common label. In some embodiments, each component of a group of different components within an affinity reagent may share a common label. In some embodiments, a component of a group of components within an affinity reagent may be an antibody, an antibody fragment, an aptamer, an avimer, a binding protein, a kinase, or a peptide.

Another aspect of the invention provides a method of uniquely identifying and quantifying n proteins in a mixture of proteins using m binding reagents, wherein m is less than n−1, and wherein each protein is identified via a unique profile of binding by a subset of the m the binding reagents.

In some instances, the method is capable of identifying more than 20% of proteins in the human proteome from a human protein sample, wherein the proteins are not substantially destroyed in the process. In some instances, the method is capable of identifying more than 20% of proteins in the proteome for any organism with an available protein sequence database (e.g. yeast, E. coli, C. elegans). In some instances, a protein sequence database may be generated by genome, exome, and/or transcriptome sequencing. In some instances, the method does not require more than 4000 affinity reagents. In some instances, the method does not require more than 100 mg of the protein sample.

Another aspect of the invention provides a method of uniquely identifying a single protein molecule. The method comprises obtaining a panel of affinity reagents, exposing the single protein molecule to each of the affinity reagents in the panel, determining whether each affinity reagent binds or does not bind the single protein molecule, and using the collected binding data to determine the identity of the single protein molecule. Additionally, in some embodiments, the identity of the single protein molecule cannot be determined by the binding data of any individual affinity reagent in the panel of affinity reagents. In some instances, affinity reagents with overlapping binding characteristics may be used to enrich affinity for any particular target.

Another aspect of the invention provides a method of determining protein characteristics. The method comprises conjugating portions of one or more proteins to a substrate, wherein each of the conjugated portions of the one or more proteins is associated with an unique spatial address on the substrate. In some examples, a unique spatial address may be a spatial address that is associated with a particular portion of a protein. The method also comprises applying a first through nth set of one or more affinity reagents to the substrate, wherein each affinity reagent of the first through nth set of one or more affinity reagents recognizes an epitope that is between one and ten residues in length, and wherein each affinity reagent of the first through nth set of one or more of affinity reagents is linked to an identifiable tag. Additionally, the method comprises that after each application of the first through nth set of one or more of affinity reagents to the substrate, the following steps are performed: observing the identifiable tag; identifying one or more unique spatial addresses of the substrate having one or more observed signal; and determining that each portion of the one or more proteins having an identified unique spatial address contains the one or more epitopes associated with the one or more observed signals.

Another aspect of the invention provides a method of determining protein characteristics. The method comprises conjugating portions of one or more proteins to a substrate, wherein each of the conjugated portions of the one or more proteins is associated with an unique spatial address on the substrate. The method also comprises applying a first through nth set of one or more affinity reagents to the substrate, wherein each affinity reagent of the first through nth set of one or more affinity reagents recognizes a family of one or more epitopes that are present in one or more proteins, and wherein each affinity reagent of the first through nth set of one or more of affinity reagents is linked to an identifiable tag. Further, the method comprises that after each application of the first through nth set of one or more affinity reagents to the substrate, the following steps are performed: observing the identifiable tag; identifying one or more unique spatial addresses of the substrate having an observed signal; and determining that each portion of the one or more proteins having an identified unique spatial address contains the epitope.

A further aspect of the invention provides a method of identifying a protein, the method comprising: acquiring a panel of affinity reagents of a known degree of nonspecificity, determining the binding properties of the affinity reagents in the panel, iteratively exposing the protein to the panel of affinity reagents, determining a set of the affinity reagents which bind the protein, and using one or more deconvolution methods based on the known binding properties of the affinity reagents to match the set of affinity reagents to a sequence of a protein, thereby determining the identity of the protein.

Additionally, another aspect of the invention provides a method of identifying a protein, the method comprising acquiring a panel of affinity reagents of a known degree of nonspecificity, determining the binding properties of the affinity reagents in the panel, iteratively exposing the protein to the panel of affinity reagents, determining a set of the affinity reagents which do not bind the protein, and using one or more deconvolution methods based on the known binding properties of the affinity reagents to match the set of affinity reagents to a sequence of a protein, thereby determining the identity of the protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 illustrates observation of a first set of anti-peptide antibodies, in accordance with some embodiments;

FIG. 8 illustrates observation of a second set of anti-peptide antibodies, in accordance with some embodiments;

FIG. 9 illustrates observation of a third set of anti-peptide antibodies, in accordance with some embodiments;

FIG. 11 illustrates proteome quantification in accordance with some embodiments;

FIG. 12 illustrates an example of an anomaly list, in accordance with some embodiments;

FIG. 16A illustrates an image showing single protein molecules conjugated on a substrate, in accordance with embodiments herein.

FIG. 18 illustrates a schematic for identification of a protein, in accordance with embodiments herein.

DETAILED DESCRIPTION OF THE INVENTION

Figure 1:
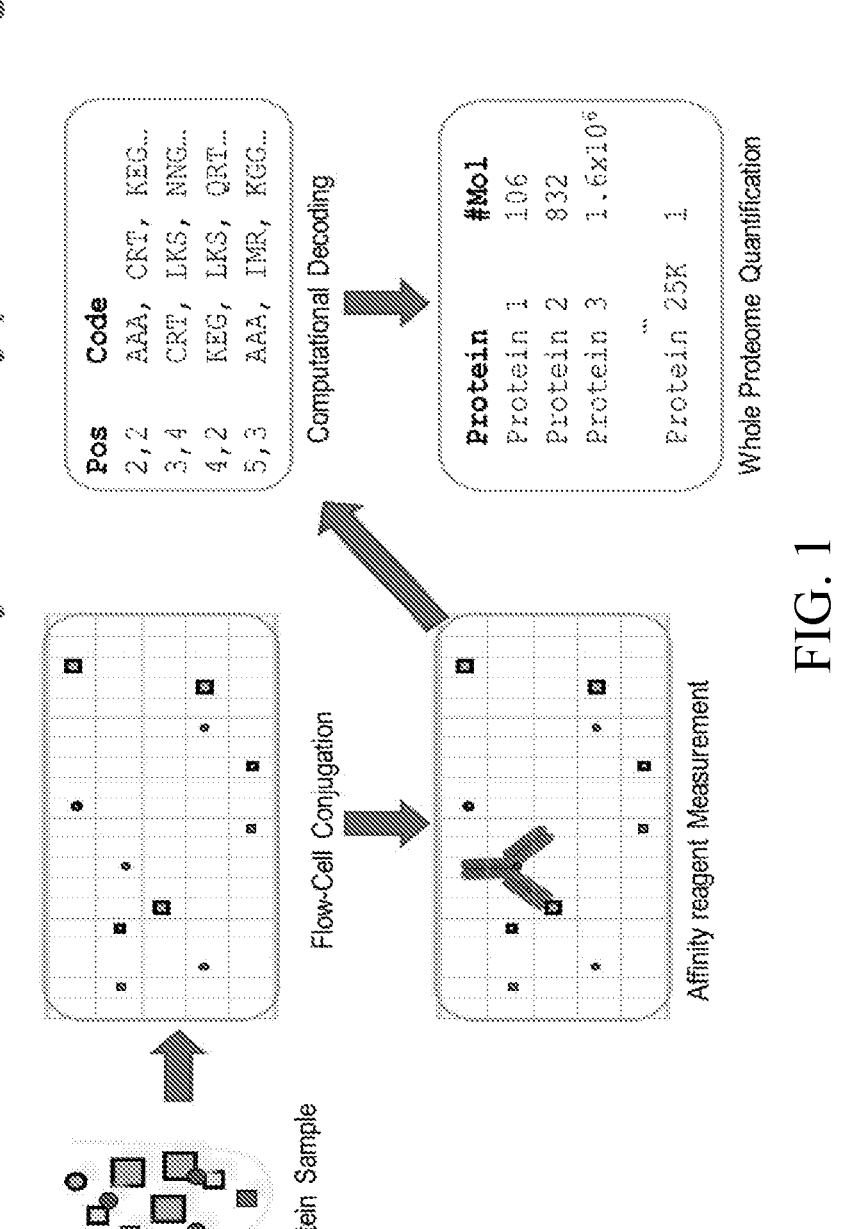
FIG. 1 illustrates a first schematic of protein quantification by anti-peptide antibody decoding, in accordance with some embodiments.

In some examples, the approach can comprise three aspects: 1) an addressable substrate in which proteins and/or protein fragments can be conjugated; 2) a set of affinity reagents, e.g. where each affinity reagent can bind to a peptide with varying specificity; and 3) a software that is able to use a combination of prior knowledge about the binding characteristics of the affinity reagents, the specific pattern of binding of affinity reagents at each address in the substrate, and/or a database of the possible sequences of the proteins in the mixture (e.g. the human proteome) to infer the identity of a protein at a precise spatial address in the substrate. In some examples, the precise spatial address may be an unique spatial address.

The phrase "individual protein molecule" is used to refer to a single molecule of protein. The molecule may comprise a full length intact protein molecule, or may be a fragment of a larger protein.

Samples

The samples may be any biological sample containing protein. The samples may be taken from tissue or cells or from the environment of tissue or cells. In some examples, the sample can comprise a tissue biopsy, blood, blood plasma, extracellular fluid, cultured cells, culture media, discarded tissue, plant matter, synthetic proteins, archael, bacterial and/or viral samples, fungal tissue, archaea, or protozoans. In some cases, a sample can comprise a mutation, a gene insertion, a gene deletion, or a combination thereof. In some cases, a sample can be a model of a state of health or a state of disease, such as an in vitro model, an ex vivo model, or an in vivo model. In some cases, the sample may be a plant or a part of a plant. Examples of plant parts which could be studied using the methods of the present disclosure include, but are not limited to: leaves, roots, stems, branches, flowers, seeds, fruits, cereal grains, growth tips, wood samples, bark samples and pollen samples. In some cases, the methods of the present disclosure may be used with parts of a fruit, leaf or seed, for example a food product such as refined flour, bran or germ. In some cases, the sample may be a food item, such as, for example, fruits, vegetables, grains, legumes, nuts, sprouts, salad leaves, leaves, fish, meat, milk, an animal or vegetable oil, eggs, or honey. In some examples, the protein can be isolated from its primary source (cells, tissue, bodily fluids such as blood, environmental samples etc) during sample preparation. The protein may or may not be purified from its primary source. In some cases the primary source can be homogenized prior to further processing. In some cases cells can be lysed using a buffer such as RIPA (RadioImmuno-Precipitation Assay) buffer, an NP-40 lysis buffer, a sodium dodecyl sulfate (SDS) lysis buffer, an ammonium-chloride-potassium (ACK) lysis buffer, or other lysis buffer. Denaturing buffers, such as a buffer which can comprise urea, dithiothreitol, or other denaturing agent, may also be used at this stage. The sample may be filtered or centrifuged to remove lipids and particulate matter. The sample may also be purified to remove nucleic acids, or may be treated with RNases and DNases. The sample may contain intact proteins, denatured proteins, protein fragments or partially degraded proteins.

The sample may be taken from a subject with a disease or disorder. The disease or disorder may be an infectious disease, an immune disorder or disease, a cancer, an allergic reaction, a toxicological disease or disorder, a genetic disease, a degenerative disease, a lifestyle disease, an injury, a rare disease or an age related disease. The infectious disease may be caused by one or more of a bacteria, a viruse, a prion, a fungus and/or a parasite. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, depression, anxiety, psychiatric disorders, post-traumatic stress disorder, sleep disorders, sleep apnea, chronic stress, stress-related disorder, substance abuse, vitamin deficiency, nutrient deficiency, arthritis, psoriasis, rhabdomyolysis, arteriosclerosis, heart disease, stroke, hypertension, liver cirrhosis, nephritis, cancer, chronic obstructive pulmonary disease (copd), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash. Some examples of toxicological diseases or disorders may include, but are not limited to, lead poisoning, radiation injuries, insect or spider envenomation, snake envenomation, and food poisoning. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time.

The sample may be taken from a subject known or suspected of having an infectious disease for which diagnostic antibodies are not available.

The sample may be taken from a subject who is believed to be healthy, such as part of a general check-up. The sample may be taken from a subject suspected of having a disease or a disorder. The sample may be taken from a subject experiencing unexplained symptoms, such as fatigue, nausea, weight loss, aches and pains, weakness, allergic reaction, muscle degradation, organ malfunction, dehydration, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

The sample may be taken from an embryo, fetus, or pregnant woman. In some examples, the sample may comprise of proteins isolated from the mother's blood plasma. In some examples, the sample may comprise proteins isolated from circulating fetal cells in the mother's blood.

The sample may be taken from a subject which is a human. In some cases, the human can be a patient, a healthy subject, or a volunteer. In some cases, the sample may be taken from a subject which is an animal which is not a human. The sample can be taken from a mouse, rat, fish, frog, woodchuck, guinea pig, hamster, rabbit, pig, cow, dog, cat, fruit fly, nematode, or other animal. The subject can be alive or deceased. In some cases, a non-human subject may comprise a model for a human disease or disorder.

In some cases, multiple samples may comprise a control sample and treatment samples. For example, an experiment may be conducted on cultured cells wherein some cells are cultured with a drug while others are cultured with a vehicle control. In another example, biopsies may be taken from two or more groups of subjects which have been exposed to different conditions, for example different diets or a therapeutic treatment. In another example, biopsies may be taken from subjects before and after an experimental treatment, such as dietary changes, exercise, or therapeutic treatments. In some cases, biopsies may be taken from subjects at regular or irregular intervals. In cases, multiple samples such as samples taken at intervals can be from the same subject or from different subjects.

In some cases, a sample may be modified before proteins are extracted. For example, a sample may be treated with a reagent to cross link proteins to each other or to other cellular components, such as nucleic acids, lipids, and carbohydrates. In some cases, a sample can be spiked with an internal standard prior to protein extraction, during protein extraction, or after protein extraction.

In some cases, proteins of a sample may be separated into fractions. For example, proteins may be separated into membrane associated proteins and non-membrane associated proteins. In some cases, proteins may be fractionated by size. For example, proteins above a certain size or below a certain size may be discarded from a sample. In some cases, proteins may be retained or discarded based upon a physical characteristic such as hydrodynamic radius, hydrophobicity, hydrophilicity, or electrical charge. In some cases, lipid rafts may be isolated from cells or tissue, and then dissociated to determine the proteins present in, or associated with, the lipid rafts. In some cases, cellular organelles may be separated prior to protein extraction, such that proteins may be separated by cellular localization. In some embodiments, cellular organelles which may be isolated prior to protein extraction may include, but may not be limited to: nuclei, nucleolei, smooth endoplasmic reticulum, rough endoplasmic reticulum, golgi apparatus, golgi vesicles, mitochondria, chloroplasts, lysosomes, vacuoles, peroxisomes, melanosomes, starch granules, and plastids. For example, a sample may be treated to isolate nuclei such that nuclear proteins can be isolated and analyzed. In some cases, a sample may be fractionated into multiple fractions, and one or more fraction may be analyzed. In some embodiments, separating the sample into different subcellular fractions may facilitate the protein identification stage, the protein preparation steps, or may provide information regarding the cellular localization of each protein.

Protein may be treated to remove modifications that may interfere with epitope binding. For example the protein may be glycosidase treated to remove post translational glycosylation. The protein may be treated with a reducing agent to reduce disulfide binds within the protein. The protein may be treated with a phosphatase to remove phosphate groups. Other non-limiting examples of post translational modifications that may be removed include acetate, amide groups, methyl groups, lipids, ubiquitin, myristoylation, palmitoylation, isoprenylation or prenylation (e.g. farnesol and geranylgeraniol), farnesylation, geranylgeranylation, glypiation, lipoylation, flavin moiety attachment, phosphopantetheinylation, and retinylidene Schiff base formation. Samples may also be treated to retain posttranslational protein modifications. In some examples, phosphatase inhibitors may be added to the sample. In some examples, oxidizing agents may be added to protect disulfide bonds.

Next, proteins may be denatured in full or in part. In some embodiments, proteins can be fully denatured. Proteins may be denatured by application of an external stress such as a detergent, a strong acid or base, a concentrated inorganic salt, an organic solvent (e.g., alcohol or chloroform), radiation or heat. Proteins may be denatured by addition of a denaturing buffer. Proteins may also be precipitated, lyophilized and suspended in denaturing buffer. Proteins may be denatured by heating. In some cases, more than one denaturation method can be used, such as heating a protein exposed to a concentrated inorganic salt, an organic solvent, a detergent, or a strong acid or base. Methods of denaturing that are unlikely to cause chemical modifications to the proteins may be preferred in some cases.

Proteins of the sample may be treated to produce shorter polypeptides, either before or after conjugation. Remaining proteins may be partially digested with an enzyme such as ProteinaseK to generate fragments or may be left intact. In further examples the proteins may be exposed to proteases such as trypsin. Additional examples of proteases may include serine proteases, cysteine proteases, threonine proteases, aspartic proteases, glutamic proteases, metalloproteases, and asparagine peptide lyases.

In some cases it may be useful to remove extremely large and small proteins (e.g. Titin), such proteins may be removed by filtration or other appropriate methods. In some examples, extremely large proteins may include proteins that are over 400 kD, 450 kD, 500 kD, 600 kD, 650 kD, 700 kD, 750 kD, 800 kD or 850 kD. In some examples, extremely large proteins may include proteins that are over about 8,000 amino acids, about 8,500 amino acids, about 9,000 amino acids, about 9,500 amino acids, about 10,000 amino acids, about 10,500 amino acids, about 11,000 amino acids or about 15,000 amino acids. In some examples, small proteins may include proteins that are less than about 10 kD, 9 kD, 8 kD, 7 kD, 6 kD, 5 kD, 4 kD, 3 kD, 2 kD or 1 kD. In some examples, small proteins may include proteins that are less than about 50 amino acids, 45 amino acids, 40 amino acids, 35 amino acids or about 30 amino acids. Extremely large or small proteins can be removed by size exclusion chromatography. Extremely large proteins may be isolated (e.g., by size exclusion chromatography, vacuum filter purification, or centrifuge filter purification), treated with proteases to produce moderately sized polypeptides and recombined with the moderately size proteins of the sample.

In some cases, proteins may be ordered by size. In some embodiments, proteins may be ordered by size before being denatured. In some embodiments, proteins may be ordered by size after being denatured. In some embodiments, proteins may be initially ordered by size before being denatured and may again be ordered by size after being denatured. In some cases, proteins may be ordered by sorting proteins into microwells. In some cases, proteins may be ordered by sorting proteins into nanowells. In some cases, proteins may be ordered by running proteins through a gel such as an SDS-PAGE gel. In some cases, the proteins may be separated by size using a sizing column, gradient centrifugation, size filtration, or any other suitable method. In some cases, proteins may be ordered by other size-dependent fractionation methods. In some cases, proteins may be separated based on charge. In some cases, proteins may be separated based on hydrophobicity. In some cases, proteins may be separated based on other physical characteristics. In some cases, proteins may be separated under denaturing conditions. In some cases, proteins may be separated under non-denaturing conditions. In some cases, different fractions of fractionated proteins may be placed on different regions of the substrate. In some cases, different portions of separated proteins may be placed on different regions of the substrate. In some cases, a protein sample may be separated in an SDS-PAGE gel and transferred from the SDS-PAGE gel to the substrate such that the proteins are sorted by size in a continuum. In some cases, a protein sample may be sorted into three fractions based on size, and the three fractions may be applied to a first, second, and third region of the substrate, respectively. In some cases, proteins used in the systems and methods described herein may be sorted. In some cases, proteins used in the systems and methods described herein may not be sorted.

Samples may be fully or partially processed and stored prior to assaying according to the methods described herein. In some cases, samples may be stored prior to processing. In some cases, samples may be stored with, or without, a storage buffer at 25° C., 2° C., −4° C., −20° C., −80° C., −196° C., −200° C. or less than −200° C. In some cases, samples may be stored in liquid nitrogen. In some cases, samples may be stored in a buffer which does not contain Tris or Phosphate ions. In some cases, samples may be stored in a buffered saline solution. In some cases, samples may be stored in a denaturing buffer. In some cases, samples may be lyophilized and stored as a powder. In some cases, a lyophilized powder may be stored in a desiccator. In some cases, a lyophilized powder may be stored with a desiccating agent.

In some cases, samples may be partially processed at one location and transported to another location for further processing. In some cases, samples may be transferred in an insulated container. In some cases, samples may be transported with an icepack, on ice, on dry ice, or in liquid nitrogen. In some cases, samples may be transported at room temperature. In some cases, samples may be transported in a denaturing buffer. In some cases, samples may be stored and/or transported as a lyophilized powder. In some embodiments, lyophilized samples may be transported in a desiccator, or with a desiccating agent.

Samples may be collected, stored, processed, and transported in any suitable container. Containers may be plastic or glass. Generally containers have a lid which provides an airtight seal. Containers may be standard laboratory collection tubes such as Eppendorf tubes, Falcon tubes, vacutainers, hematocrit tubes, micro hematocrit tubes, or test tubes. In some cases, containers with low protein binding properties may be preferred. In some cases, containers for sample collection may be treated with a reagent to prevent, or minimize, blood coagulation. For example, blood samples may be collected in tubes with EDTA coating. Containers may be treated to decrease protein binding to the walls of the container. For example, containers may be treated by passivation.

Proteins may be tagged, e.g. with identifiable tags, to allow for multiplexing of samples. Some non-limiting examples of identifiable tags include: fluorophores or nucleic acid barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, R-Phycoerythrin, Allophcocyanin, or other fluorophores known in the art.

A protein tag can be a tag which is not fluorescent, such as a peptide tag. A peptide tag can be an AviTag, a C-tag, a calmodulin-tag, an E-tag, a FLAG-tag, an HA-tag, a His-tag, a Myc-tag, an NE-tag, a RholD4-tag, an S-tag, an SBP-tag, a Softag 1, a Softag3, a Spot-tag, a Strep-tag, a TC tag, a Ty tag, a V5 tag a VSV-tag, or an Xpress tag. In some cases, a protein tag can comprise a radiolabel.

In some cases, a protein can be tagged with more than one tag. For example, a protein can be tagged with a fluorophore and a barcoded base linker, with a fluorophore and a peptide tag, with a fluorophore and a radiolabel, with a barcoded base linker and a peptide tag, with a barcoded base linker and a radiolabel, or with a peptide tag and a radiolabel. In some cases, a protein can be tagged with more than one fluorophore, more than one barcoded base linker, more than one radiolabel, or more than one peptide tag. In some cases, a protein can be tagged with 2, 3, 4, 5, or more tags.

Any number of protein samples may be multiplexed. For example a multiplexed reaction may contain proteins from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100 or more than 100 initial samples. The identifiable tags may provide a way to interrogate each protein as to its sample of origin, or may direct proteins from different samples to segregate to different areas on a solid support.

In some embodiments, a sample may be spiked with an amount of a protein which is foreign to the sample. This can be done e.g. as an internal measurement control, purification control, or other control. In some cases, the protein which is foreign to the sample may not interact with the sample. In some cases, the protein which is foreign to the sample may interact with the sample, for example to facilitate or improve detection of a protein in the sample. Generally a sample may be spiked with a protein that does not have a homolog in the species, or group of species, from which the sample was isolated. In some cases, the sample may be spiked with a protein from a species which is phylogenetically distant from the species, or group of species, from which the sample was isolated. For example a human derived sample may be spiked with a phylogenetically distant protein such as a jellyfish green fluorescent protein (GFP). Generally, since the human sample should not contain any GFP, the total amount of GFP in the sample may be determined by the amount of GFP spiked into the sample. In this case, since the GFP is known to be in the spiked sample, and since the amount of GFP that was spiked into the sample is known, the GFP can be used as a positive control (e.g., for either or both of the detection and quantification steps).

Substrate

In some embodiments, the proteins are then applied to a functionalized substrate to chemically attach proteins to the substrate. In some cases, the proteins may be attached to the substrate via biotin attachment. In some cases, the proteins may be attached to the substrate via nucleic acid attachment. In some embodiments, the proteins may be applied to an intermediate substance, where the intermediate substance is then attached to the substrate. In some cases, proteins may be conjugated to beads (e.g., gold beads) which may then be captured on a surface (e.g., a thiolated surface). In some cases, one protein may be conjugated to each bead. In some cases, proteins may be conjugated to beads (e.g., one protein per bead) and the beads may be captured on a surface (e.g. in microwells and/or nanowells).

The substrate may be any substrate capable of forming a solid support. Substrates, or solid substrates, as used herein can refer to any solid surface to which proteins can be covalently or non-covalently attached. Non-limiting examples of solid substrates include particles, beads, slides, surfaces of elements of devices, membranes, flow cells, wells, chambers, macrofluidic chambers, be flat or curved, or can have other shapes, and can be smooth or textured. In some cases, substrate surfaces may contain microwells. In some cases, substrate surfaces may contain nanowells. In some cases, substrate surfaces may contain one or more microwells in combination with one or more nanowells. In some embodiments, the substrate can be composed of glass, carbohydrates such as dextrans, plastics such as polystyrene or polypropylene, polyacrylamide, latex, silicon, metals such as gold, or cellulose, and may be further modified to allow or enhance covalent or non-covalent attachment of the oligonucleotides. For example, the substrate surface may be functionalized by modification with specific functional groups, such as maleic or succinic moieties, may be functionalized to confer positive or negative charge, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The substrate may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane. The substrate and process for oligonucleotide attachment are preferably stable for repeated binding, washing, imaging and eluting steps. In some examples, the substrate may be a slide or a flow cell.

An ordered array of functional groups, or of regions of functional groups forming attachment sites, may be created by, for example, photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, local oxidation nanolithography, molecular self-assembly, stencil lithography, or electron-beam lithography. In some cases, all attachment sites on a substrate may comprise the same functional groups. In some cases, most attachment sites on a substrate may comprise the same functional groups. In some cases, a substrate may comprise two or more different types of attachment sites, which may differ by size, spacing, or chemical or physical properties. Attachment sites in an ordered array may be located such that each attachment site is less than 200 nanometers (nm), or about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, or more than 2000 nm from any other functional group. Functional groups in a random spacing may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than 100 nm from any other functional group.

In some cases, a substrate may comprise an array of attachment sites. In some embodiments, a substrate may have an uncharged surface except for the areas of the attachment sites which may be positively charged. A substrate may comprise less than about 103 attachment sites, about 105 attachment sites, about 106 attachment sites, about 107 attachment sites, about 108 attachment sites, about 109 attachment sites, about 1010 attachment sites, about 1011 attachment sites, about 1012 attachment sites, about 1013 attachment sites, or more than about 1015 attachment sites. In some cases, the substrate may have about 1010 attachment sites. In some cases, the attachment sites may be arranged into groups of about 104, about 105, about 106, about 107, about 108, about 109, or about 1010. In some cases, each group of attachment sites may also contain a fiducial. In some cases, each group of attachment sites may also contain fluorescent controls. In some cases, one or more of the attachment sites in the group of attachment sites may have a different chemistry than other attachment sites so as to allow a control to be targeted to that site. In some cases, attachment sites in a first group may differ from attachment sites of a second group. In some embodiments, attachment sites in different groups may differ by size, spacing, chemical, and/or physical properties. In some cases attachment sites within a group may differ by size, spacing, chemical, and/or physical properties.

The substrate may be indirectly functionalized. For example, the substrate may be PEGylated and a functional group may be applied to all or a subset of the PEG molecules. Additionally, as discussed above, in some cases beads (e.g., gold beads or magnetic beads) may be conjugated, and then the beads may be captured on a surface (e.g., a thiolated surface or a magnetic surface). In some cases, one protein may be conjugated to each bead. In some cases, proteins may be conjugated to beads (e.g., one protein per bead) and the beads may be captured on a surface (e.g. in microwells and/or nanowells).

The substrate may be functionalized using techniques suitable for microscaled or nanoscaled structures (e.g., an ordered structure such as microwells, nanowells, micropillars, single molecular arrays, nanoballs, nanopillars, or nanowires). In some cases, a substrate may have microwells of different sizes. In some cases, microwells may be 1 micrometer (μm), may be about 2 μm, about 3 μm, about 4 μm, about 5 μm, about 6 μm, about 7 μm, about 8 μm, about 9 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, about 200 μm, about 205 μm, about 210 μm, about 215 μm, about 220 μm, about 225 μm, about 230 μm, about 235 μm, about 240 μm, about 245 μm, about 250 μm, about 255 μm, about 260 μm, about 265 μm, about 270 μm, about 275 μm, about 280 μm, about 285 μm, about 290 μm, about 295 μm, about 300 μm, about 305 μm, about 310 μm, about 315 μm, about 320 μm, about 325 μm, about 330 μm, about 335 μm, about 340 μm, about 345 μm, about 350 μm, about 355 μm, about 360 μm, about 365 μm, about 370 μm, about 375 μm, about 380 μm, about 385 μm, about 390 μm, about 395 μm, about 400 μm, about 405 μm, about 410 μm, about 415 μm, about 420 μm, about 425 μm, about 430 μm, about 435 μm, about 440 μm, about 445 μm, about 450 μm, about 455 μm, about 460 μm, about 465 μm, about 470 μm, about 475 μm, about 480 μm, about 485 μm, about 490 μm, about 495 μm, about 500 μm, or more than 500 μm. In some cases, a substrate may have microwells that range in size from 5 μm to 500 μm. In some cases, a substrate may have microwells that range in size from about 5 μm to about 500 μm. In some cases, a substrate may have microwells that range in size from 10 μm to 100 μm. In some cases, a substrate may have microwells that range in size from about 10 μm to about 100 μm. In some cases, a substrate may have a range of different sized microwells such that proteins of different sizes may be sorted into different sized microwells. In some cases, microwells in the substrate may be distributed by size (e.g. with larger microwells distributed in a first region and with smaller microwells distributed in a second region). In some cases, a substrate may have microwells of about 10 different sizes. In some cases, a substrate may have microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

In some cases, a substrate may have nanowells of different sizes. In some cases, nanowells may be about 100 nanometers (nm), about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or between 950 nm and 1 micrometer. In some cases, a substrate may have nanowells that range in size from 100 nm to 1 micrometer. In some cases, a substrate may have nanowells that range in size from 100 nm to 500 nm. In some cases, a substrate may have a range of different sized nanowells such that proteins of different sizes may be sorted into different sized nanowells. In some cases, nanowells in the substrate may be distributed by size (e.g. with larger nanowells distributed in a first region and with smaller nanowells distributed in a second region). In some cases, a substrate may have nanowells of about ten different sizes. In some cases, a substrate may have nanowells of about 20 different sizes, or more than 30 different sizes.

In some cases, a substrate may have a range of different sized nanowells and/or microwells such that proteins of different sizes may be sorted into different sized nanowells and/or microwells. In some cases, nanowells and/or microwells in the substrate may be distributed by size (e.g. with larger microwells distributed in a first region and with smaller nanowells distributed in a second region). In some cases, a substrate may have nanowells and/or microwells of about ten different sizes. In some cases, a substrate may have nanowells and/or microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

The substrate may comprise any material, including metals, glass, plastics, ceramics or combinations thereof. In some preferred embodiments, the solid substrate can be a flow cell. The flow cell can be composed of a single layer or multiple layers. For example, a flow cell can comprise a base layer (e.g., of boro silicate glass), a channel layer (e.g., of etched silicon) overlaid upon the base layer, and a cover, or top, layer. When the layers are assembled together, enclosed channels can be formed having inlet/outlets at either end through the cover. The thickness of each layer can vary, but is preferably less than about 1700 μm. Layers can be composed of any suitable material known in the art, including but not limited to photosensitive glasses, borosilicate glass, fused silicate, PDMS or silicon. Different layers can be composed of the same material or different materials.

In some embodiments, flow cells can comprise openings for channels on the bottom of the flow cell. A flow cell can comprise millions of attached target conjugation sites in locations that can be discretely visualized. In some embodiments, various flow cells of use with embodiments of the invention can comprise different numbers of channels (e.g., 1 channel, 2 or more channels, 3 or more channels, 4 or more channels, 6 or more channels, 8 or more channels, 10 or more channels, 12 or more channels, 16 or more channels, or more than 16 channels). Various flow cells can comprise channels of different depths or widths, which may be different between channels within a single flow cell, or different between channels of different flow cells. A single channel can also vary in depth and/or width. For example, a channel can be less than about 50 μm deep, about 50 μmdeep, less than about 100 μm deep, or about 100 μm deep. In some cases, a channel can be up to about about 500 μm deep, about 500 μm deep, or more than about 500 μm deep at one or more points within the channel. Channels can have any cross sectional shape, including but not limited to a circular, a semi-circular, a rectangular, a trapezoidal, a triangular, or an ovoid cross-section.

The proteins may be spotted, dropped, pipetted, flowed, washed or otherwise applied to the substrate. In the case of a substrate that has been functionalized with a moiety such as an NHS ester, no modification of the protein is required. In the case of a substrate that has been functionalized with alternate moieties (e.g. a sulfhydryl, amine, or linker nucleic acid), a crosslinking reagent (e.g. disuccinimidyl suberate, NHS, sulphonamides) may be used. In the case of a substrate that has been functionalized with linker nucleic acid the proteins of the sample may be modified with complementary nucleic acid tags.

In some cases, a protein may be conjugated to a nucleic acid. Using the nucleic acid, a nucleic acid nanoball may be formed, thereby having the protein linked to the nucleic acid nanoball. When the nucleic acid nanoball is attached to a substrate, the protein attached to the nucleic acid is attached to the substrate by way of the nucleic acid nanoball. A DNA nanoball can be attached (e.g. by adsorption or by conjugation) to a substrate. The substrate may have an amine functionalized surface to which the nucleic acid nanoballs can attach.

In some cases, a nucleic acid nanoball or structured nucleic acid particle may be formed with a functionally active terminus (e.g. a maleimide, NHS-Ester, etc.). The protein may then be conjugated to the nanoball or structured nucleic acid particle, thereby having the protein linked to the nucleic acid nanoball or structured nucleic acid particle. When the nucleic acid nanoball or structured nucleic acid particle is attached to a substrate, the protein attached to the nucleic acid is attached to the substrate by way of the nucleic acid nanoball. A nucleic acid nanoball or structured nucleic acid particle can be attached (e.g. by adsorption or by conjugation) to a substrate. The substrate may have an amine functionalized surface to which a nucleic acid nanoball or structured nucleic acid particle can attach. A structured nucleic acid particle may comprise at least two conjugated oligonucleotides. Structured nucleic acid particles may comprise one or more sections of double-stranded nucleic acids, single-stranded nucleic acids, or combinations thereof. A structured nucleic acid may comprise a nucleic acid origami structure.

Photo-activatable cross linkers may be used to direct cross linking of a sample to a specific area on the substrate. Photo-activatable cross linkers may be used to allow multiplexing of protein samples by attaching each sample in a known region of the substrate. Photo-activatable cross linkers may allow the specific attachment of proteins which have been successfully tagged, for example by detecting a fluorescent tag before cross linking a protein. Examples of photo-activatable cross linkers include, but are not limited to, N-5-azido-2-nitrobenzoyloxysuccinimide, sulfosuccinimidyl 6-(4'-azido-2'-nitrophenylamino) hexanoate, succinimidyl 4,4'-azipentanoate, sulfosuccinimidyl 4,4'-azipentanoate, succinimidyl 6-(4,4'-azipentanamido) hexanoate, sulfosuccinimidyl 6-(4,4'-azipentanamido) hexanoate, succinimidyl 2-((4,4'-azipentanamido)ethyl)-1,3'-dithiopropionate, and sulfosuccinimidyl 2-((4,4'-azipentanamido) ethyl)-1,3'-dithiopropionate.

Samples may also be multiplexed by restricting the binding of each sample to a discrete area on the substrate. For example the substrate may be organized into lanes. Another method for multiplexing is to apply the samples iteratively across the substrate, following each sample application with a protein detection step utilizing a nonspecific protein binding reagent or dye. In some cases, examples of dyes may include fluorescent protein gel stains such as SYPRO® Ruby, SYPRO® Orange, SYPRO® Red, SYPRO® Tangerine, and Coomassie™ Fluor Orange.

By tracking the locations of all proteins after each addition of sample it is possible to determine the stage at which each location on the substrate first contained a protein, and thus from which sample that protein was derived. This method may also determine the saturation of the substrate after each application of sample and allows for maximization of protein binding on the substrate. For example if only 30% of functionalized locations are occupied by protein after a first application of a sample then either a second application of the same sample or an application of a different sample may be made.

One or more polypeptides may be attached to the substrate by one or more residues. In some examples, the polypeptide(s) may be attached via the N terminal, C terminal, both terminals, or via an internal residue.

In addition to permanent crosslinkers, it may be appropriate for some applications to use photo-cleavable linkers and that doing so enables proteins to be selectively extracted from the substrate following analysis. In some cases photo-cleavable cross linkers may be used for several different multiplexed samples. In some cases photo-cleavable cross linkers may be used from one or more samples within a multiplexed reaction. In some cases a multiplexed reaction may comprise control samples cross linked to the substrate via permanent crosslinkers and experimental samples cross linked to the substrate via photo-cleavable crosslinkers.

Each conjugated protein may be spatially separated from each other conjugated protein such that each conjugated protein is optically resolvable. Proteins may thus be individually labeled with a unique spatial address. In some embodiments, this can be accomplished by conjugation using low concentrations of protein and low density of attachment sites on the substrate so that each protein molecule is spatially separated from each other protein molecule. Low concentrations of protein can be less than about 100 µM, less than about 50 µM, less than about 10 µM, less than about 5 µM, less than about 1 µM, less than about 0.5 µM, or less than about 0.1 µM. Low density of attachment sites can be less than 1 attachment site per 0.1 µm, less than 1 attachment site per 1 µm, less than 1 attachment site per 10 µm, or less than 1 attachment site per 100 µm. In some examples where photo-activatable crosslinkers are used, a light pattern may be used such that proteins are affixed to predetermined locations.

In some methods, bulk proteins that have been purified may be conjugated to a substrate and processed using methods described herein so as to identify the purified protein. Bulk proteins may comprise purified proteins that have been collected together or pooled. In some examples, bulk proteins may be conjugated at a location that is spatially separated from each other conjugated protein or bulk proteins such that each conjugated protein or bulk protein is optically resolvable. Proteins, or bulk proteins, may thus be individually labeled with a unique spatial address. In some embodiments, this can be accomplished by conjugation using low concentrations of protein and low density of attachment sites on the substrate so that each protein molecule is spatially separated from each other protein molecule. In examples where photo-activatable crosslinkers are used, a light pattern may be used such that one or more proteins are affixed to predetermined locations.

Figure 3:
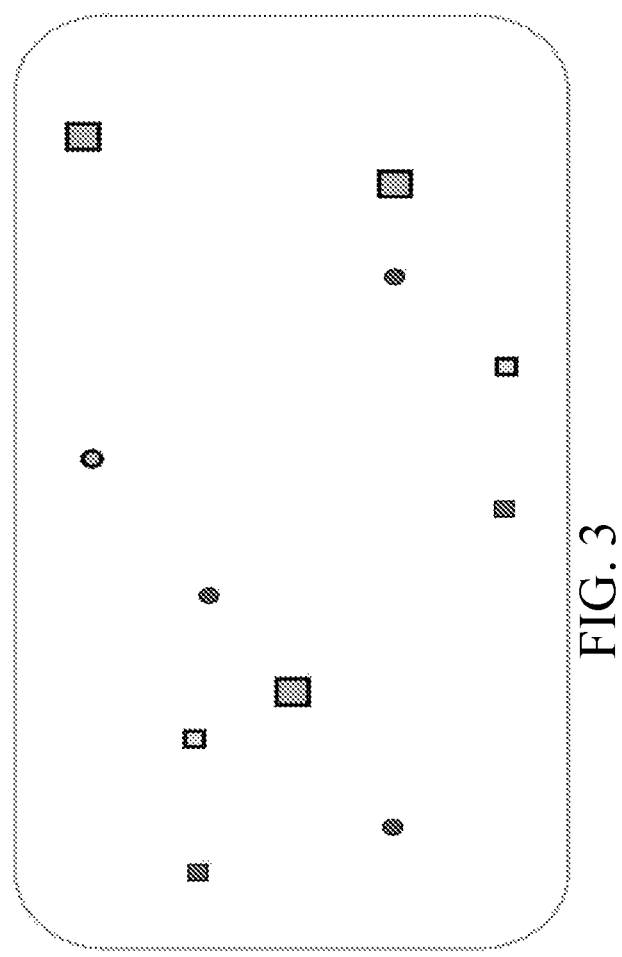
FIG. 3 illustrates flow cell conjugation, in accordance with some embodiments.
Figure 3:
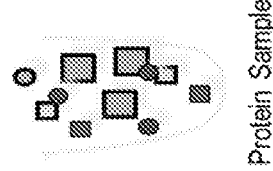
Figure 4:
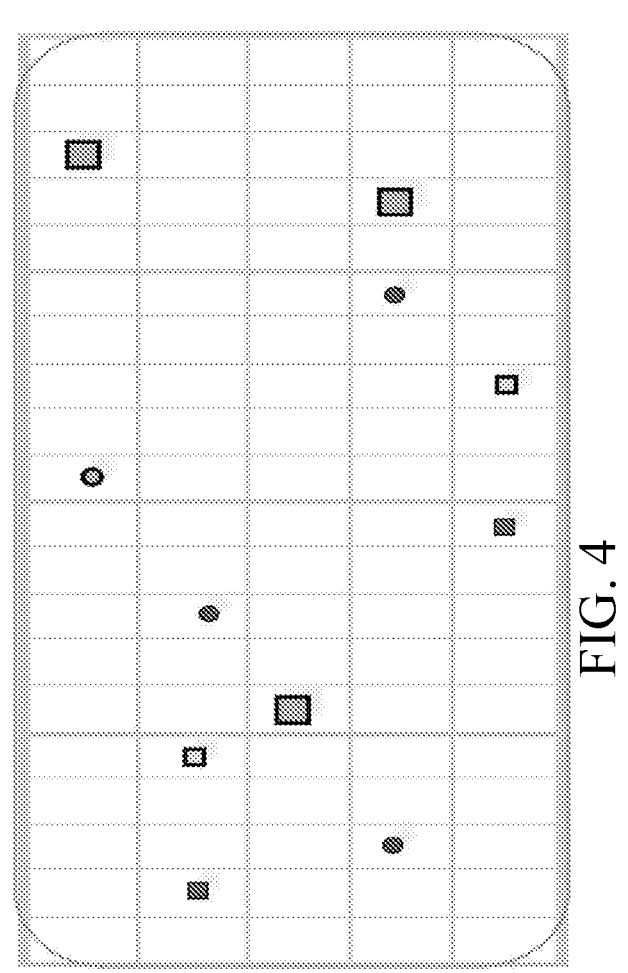
FIG. 4 illustrates a grid of unique spatial addresses on a flow cell, in accordance with some embodiments.
Figure 4:
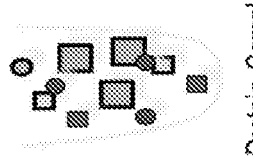

In some embodiments, each protein may be associated with a unique spatial address. For example, once the proteins are attached to the substrate in spatially separated locations, each protein can be assigned an indexed address, such as by coordinates (see FIG. 3). In some examples, a grid of pre-assigned unique spatial addresses may be predetermined. In some embodiments the substrate may contain easily identifiable fixed marks such that placement of each protein can be determined relative to the fixed marks of the substrate. In some examples the substrate may have grid lines and/or an "origin" or other fiducials permanently marked on the surface (see FIG. 4). In some examples the surface of the substrate may be permanently or semi-permanently marked to provide a reference by which to locate cross-linked proteins. The shape of the patterning itself, such as the exterior border of the conjugated polypeptides may also be used as fiducials for determining the unique location of each spot.

The substrate may also contain conjugated protein standards and controls. Conjugated protein standards and controls may be peptides or proteins of known sequence which have been conjugated in known locations. In some examples, conjugated protein standards and controls may serve as internal controls in an assay. The proteins may be applied to the substrate from purified protein stocks, or may be synthesized on the substrate through a process such as Nucleic Acid-Programmable Protein Array (NAPPA).

In some examples, the substrate may comprise fluorescent standards. These fluorescent standards may be used to calibrate the intensity of the fluorescent signals, for example from assay to assay. These fluorescent standards may also be used to correlate the intensity of a fluorescent signal with the number of fluorophores present in an area. Fluorescent standards may comprise some or all of the different types of fluorophores used in the assay.

In some cases, the substrate can comprise another standard, such as a colorimetric standard, a radiolabeled standard, or a magnetic standard.

Affinity Reagents

Once the substrate has been conjugated with the proteins from the sample, multi-affinity reagent measurements can be performed. The measurement processes described herein may utilize various affinity reagents.

Affinity reagents may be any reagents which bind proteins or peptides with reproducible specificity. For example the affinity reagents may be antibodies, antibody fragments, aptamers, avimers, binding proteins, kinases or peptides. In some cases, an antibody can be an IgG, an IgD, an IgE, an IgA, an IgM, or a combination thereof. In some cases an antibody fragment can be a nanobody, an Fab, a Fc, an IgNAR, a hcIgG, or an scFv. An aptamer can be for example a DNA aptamer, an RNA aptamer, an XNA aptamer, or a peptide aptamer. An aptamer may comprise non-naturally occurring nucleotides or amino acids. A binding protein can be a binding protein which is naturally occurring in the same organism as the sample is from, naturally occurring in a different organism as the sample is from, modified from a naturally occurring protein, or a synthetic protein. In some cases, a kinase can be a protein kinase. In some cases, a peptide can be a short amino acid chain. A peptide can be less than 100 amino acids, less than 75 amino acids, less than 50 amino acids, less than 25 amino acids, or less than 10 amino acids long. In some cases, an affinity reagent can be a hybrid of two or more of an antibody, an antibody fragment, an avimer, a binding protein, a kinase, or a peptide. In some cases, an affinity reagent can be monovalent, bivalent, trivalent, or multivalent.

In some cases, the affinity reagents may comprise a mix of different types of affinity reagents. In some cases, the affinity reagents used for an assay as described herein may comprise 1, 2, 3, 4, or more than 4 different types of affinity reagents. For example, an assay may utilize 100 affinity reagents of which 80 affinity reagents are aptamers, 10 are antibodies, and 10 are avimers. In another example, an assay may utilize about 1000 affinity reagents, of which about 400 may be aptamers, about 30 may be antibodies, about 300 may be avimers, and about 70 may be peptides. In another example, an assay may utilize a number of affinity reagents, of which about 50% may be antibodies, about 40% may be aptamers, and about 10% may be peptides. In another example, an assay may use a number of affinity reagents, of which about 90% may be aptamers, and about 10% may be peptides. In some cases, at least about 5%, 10%, 15%, 20%, 25%, 30%, 35%, 40%, 45%, 50%, 55%, 60%, 65%, 70%, 75%, 80%, 85%, 90%, 95%, 98%, or 99% of affinity reagents used in an assay may be of the same type. In some cases, the affinity reagents used for an assay as described herein may be predominantly a single type of affinity reagent.

Figure 5:
FIG. 5 illustrates de-constructing a protein as sets of peptides that can be matched with multiaffinity antibodies, in accordance with some embodiments.

In some examples, monoclonal antibodies may be preferred as affinity reagents. In some examples, antibody fragments such as Fab fragments may be preferred. In some cases the affinity reagents may be commercially available affinity reagents, such as commercially available antibodies. In some cases the desired affinity reagents may be selected by screening commercially available affinity reagents to identify those with useful characteristics. In some cases, affinity reagents may be screened for their ability to bind a single protein. In some cases, affinity reagents may be screened for their ability to bind an epitope or amino-acid sequence (see FIG. 5). In some cases, groups of affinity reagents may be screened for their ability to collectively resolve similar proteins (e.g those with highly similar sequence) through differential binding. In some cases, affinity reagents may be screened for to have overlapping binding characteristics to increase binding specificity for a particular protein. Screening of affinity reagents may be performed in a variety of different ways. One example would be to screen affinity reagents against a NAPPA or an epitope tiling array. In some cases, protein-specific affinity reagents designed to bind to a protein target may be used (e.g. commercially available antibodies or aptamers). In some cases, multiple protein-specific affinity reagents may be mixed prior to binding measurement. For example, for each binding measurement pass, a new mixture of protein specific affinity reagents may be selected comprising a subset of the available affinity reagents selected at random from the complete set. For example, each subsequent mixture may be generated in the same random manner, with the expectation that many of the affinity reagents will be present in more than one of the mixtures. In some cases, protein identifications may be generated more rapidly using mixtures of protein-specific affinity reagents. In some cases, such mixtures of protein-specific affinity reagents may increase the percentage of unknown proteins for which an affinity reagent binds in any individual pass. Mixtures of affinity reagents may consist of 1%, 5%, 10%, 20%, 30%, 40%, 50%, 60%, 70%, 80%, 90% or more of all available affinity reagents.

An affinity reagent can have a specificity of at most about $10^{-5}$ M, at most about $10^{-6}$ M, at most about $10^{-7}$ M, at most about $10^{-8}$ M, at most about $10^{-9}$ M, at most about $10^{-10}$ M, at most about $10^{-11}$ M, or at most about $10^{-12}$ M.

The affinity reagents may have high, moderate or low specificity. In some examples the affinity reagents may recognize several different epitopes. In some examples the affinity reagents may recognize epitopes present in two or more different proteins. In some examples the affinity reagents may recognize epitopes present in many different proteins. In some cases an affinity reagent used in the methods of this disclosure may be highly specific for a single epitope. In some cases an affinity reagent used in the methods of this disclosure may be highly specific for a single epitope containing a posttranslational modification.

Figure 6:
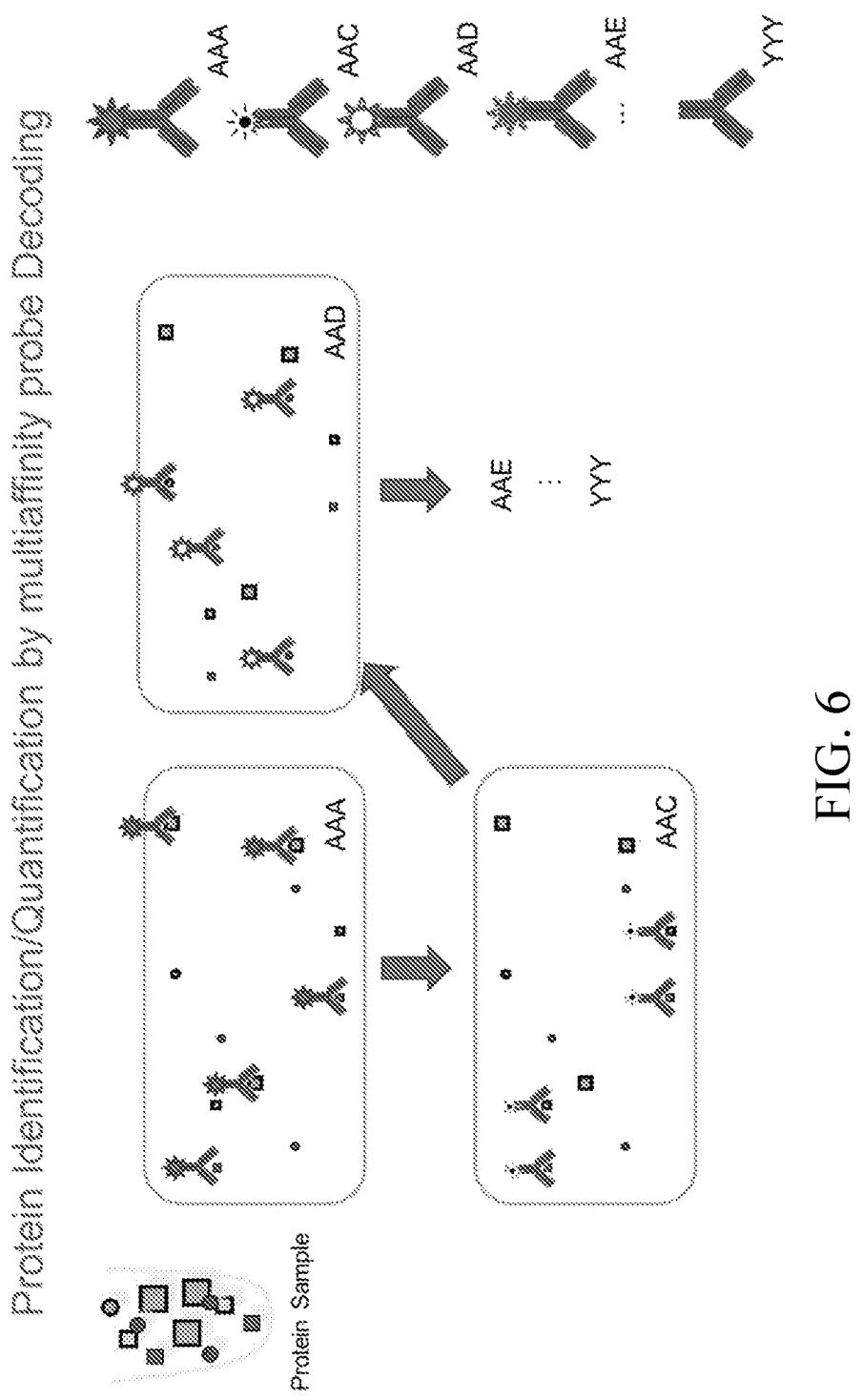
FIG. 6 illustrates a schematic of protein identification/quantification by anti-peptide antibody decoding, in accordance with some embodiments.

In some embodiments, an affinity reagent that is directed towards identifying a target amino acid sequence may comprise a group of different components which are not differentiated or distinguishable from each other as used in methods described herein. In some embodiments, an affinity reagent may comprise a group of different components. In some embodiments, each component within an affinity reagent may share a common label. In some embodiments, each component of a group of different reagents within an affinity reagent may share a common label. In some embodiments, a component of a group of components within an affinity reagent may be an antibody, an aptamer, an avimer, a binding protein, or a peptide. In particular, the different components that may be used to identify the same target amino acid sequence may use the same detection moiety to identify the same target amino acid sequence. For example, an affinity reagent which binds a trimer amino acid sequence (AAA) regardless of flanking sequences may comprise either a single probe which binds the trimer AAA sequence without any effect from flanking sequences. In some cases, an affinity reagent which binds a trimer AAA sequence regardless of flanking sequences can comprise a group of probes which can bind to different amino acid epitopes. In some cases, a group of probes can comprise at least 50, 100, 200, 300, 400, 500, or 600 probes. In some cases, the group of probes can bind to 2, 3, 4, 5, 6, 7, 8, 9, or 10 different amino acid epitopes (see FIG. 6). In some examples, a group of 400 probes, each of which binds to a different 5 amino acid epitope of the form aAAAB, where a and B may be any amino acid. In the some embodiments, the 400 probes may be combined such that there is an equal amount of each one. In some cases of the second case, the 400 probes may be combined such that the amounts of each probe may be weighted by the characteristic binding affinities of each probe such that there is an equal probability of any given 5 amino acid epitope being bound.

An affinity reagent having multiple components that share a common identifiable tag is distinct from a multiplexed affinity reagent pool. An affinity reagent comprising multiple components which share a common identifiable tag may be referred to as composite affinity reagent. Additionally, the detected signal from each component of a composite affinity reagent may be indistinguishable from the detected signals of each other component of the composite affinity reagent. Data from a composite affinity reagent may be collected and analyzed as if from a single-component affinity reagent having the composite binding properties.

In some cases, multiple components of a composite affinity reagent may be of the same type. For example, an affinity reagent may comprise a group of about 2, 3, 4, 5, 6, 7, 8, 9, 10, 15, 20, 25, 30, 40, 50, 75, 100, or more than 100 aptamers. In some cases, the multiple components of an affinity reagent, such as a composite affinity reagent, may be of different types. For example, an affinity reagent can comprise a combination of two or more of aptamers, avimers, antibodies, antibody fragments, or peptides. Such an affinity reagent can comprise at least about 1, 5, 10, 15, 20, 25, 30, 35, 40, 45, 50, 55, or 60 aptamers, at least about 1, 5, 10, 15, 20, 25, 30, 35, 40, 45, 50, 55, or 60 avimers, at least about 1, 5, 10, 15, 20, 25, 30, 35, 40, 45, 50, 55, or 60 antibodies, at least about 1, 5, 10, 15, 20, 25, 30, 35, 40, 45, 50, 55, or 60 antibody fragments, or at least about 1, 5, 10, 15, 20, 25, 30, 35, 40, 45, 50, 55, or 60 peptides. For example, an affinity reagent may comprise 15 aptamers and 5 antibodies. In another example, an affinity reagent may comprise 45 aptamers, 7 antibodies, and 3 avimers. In another example, an affinity reagent may comprise 14 antibodies and 2 aptamers.

In some cases, a plurality of composite affinity reagents may be designed for a given genome. In some cases, two different composite affinity reagents may be designed to be highly orthogonal to each other (i.e., to bind very different sets of proteins from the given proteome). In some cases, two different composite affinity reagents may be designed to be highly similar to each other (i.e., to bind very similar sets of proteins from the given proteome). In some cases, a large proteome can be identified using a set of reagents which is at least about 100 fold, at least about 500, fold, at least about 1000 fold, at least about 5000 fold, at least about 10000 fold, or at least about 50000 fold smaller than the size of the proteome. In some cases, strategic design of composite affinity reagents may allow most or all proteins in a proteome of about 30,000 proteins to be identified using only 15, 16, 17, 18, 19, or 20 composite affinity reagents. In some cases, strategic design of composite affinity reagents may allow most or all proteins in a proteome of about 50,000 proteins to be identified using only 16, 17, 18, 19, 20, or 21 composite affinity reagents. In some cases, strategic design of composite affinity reagents may allow most or all proteins in a proteome of about 100,000 proteins to be identified using only 17, 18, 19, 20, 21, or 22 composite affinity reagents. In some cases, strategic design of composite affinity reagents may allow most or all proteins in a proteome of about 250,000 proteins to be identified using only 18, 19, 20, 21, 22, or 23 composite affinity reagents.

In some cases, an affinity reagent may comprise a set of components, such that the affinity reagent binds to about half of the proteins in a given proteome. Several such affinity reagents may be designed which can bind to about half of the proteins in a proteome. Several such affinity reagents which each bind to about half of the proteins in a proteome may be used sequentially to identify proteins in a sample. Provided each affinity reagent which binds about half of the proteins in a proteome has a different binding profile from each of the other affinity reagents, the number of unique binding profiles recognized by N such affinity reagents can be about $2^N$. For example, where N is 1, 2 distinct binding profiles possible (bound or not bound) can be possible. Where N is 2, 4 distinct binding profiles (e.g., bound by both, bound by $1^{st}$ and not $2^{nd}$, not bound by first and bound by $2^{nd}$, and not bound by either) can be possible. Where N is 3, 8 distinct binding profiles can be possible. Where N is 4, 16 distinct binding profiles can be possible. Where N is 5, 32 distinct binding profiles can be possible. Where N is 6, 64 distinct binding profiles can be possible. Where N is 7, 128 distinct binding profiles can be possible. Where N is 8, 256 distinct binding profiles can be possible. Where N is 9, 512 distinct binding profiles can be possible. Where N is 10, 1,024 distinct binding profiles can be possible. Where N is 11, 2,048 distinct binding profiles can be possible. Where N is 12, 4,096 distinct binding profiles can be possible. Where N is 13, 8,192 distinct binding profiles can be possible. Where N is 14, 16,384 distinct binding profiles can be possible. Where N is 15, 32,768 distinct binding profiles can be possible. Where N is 16, 56,636 distinct binding profiles can be possible. Where N is 17, 131,072 distinct binding profiles can be possible. Where N is 18, 262, 144 distinct binding profiles can be possible. Where N is 19, 524,288 distinct binding profiles can be possible. Where N is 20, 1,048,576 distinct binding profiles can be possible. In some embodiments, it may be possible to identify all proteins in a proteome using 10, 11, 12, 13, 14, 15, 16, 17, 18, 19, or 20 rounds of binding and detection with affinity reagents which each recognize a different about half of the proteome.

Novel affinity reagents may be generated by any method known in the art. Methods of developing affinity reagents include SELEX, phage display, and inoculation. In some examples affinity reagents may be designed using structure based drug design methods. Structure-based drug design (or direct drug design) utilizes knowledge of the three dimensional structure of the epitope of interest and the binding site of the affinity reagent.

In some cases the affinity reagents may be labeled with nucleic acid barcodes. In some examples, nucleic acid barcodes may be used to purify affinity reagents after use. In some examples, nucleic acid barcodes may be used to sort the affinity reagents for repeated uses. In some cases the affinity reagents may be labeled with fluorophores which may be used to sort the affinity reagents after use.

Figure 7:
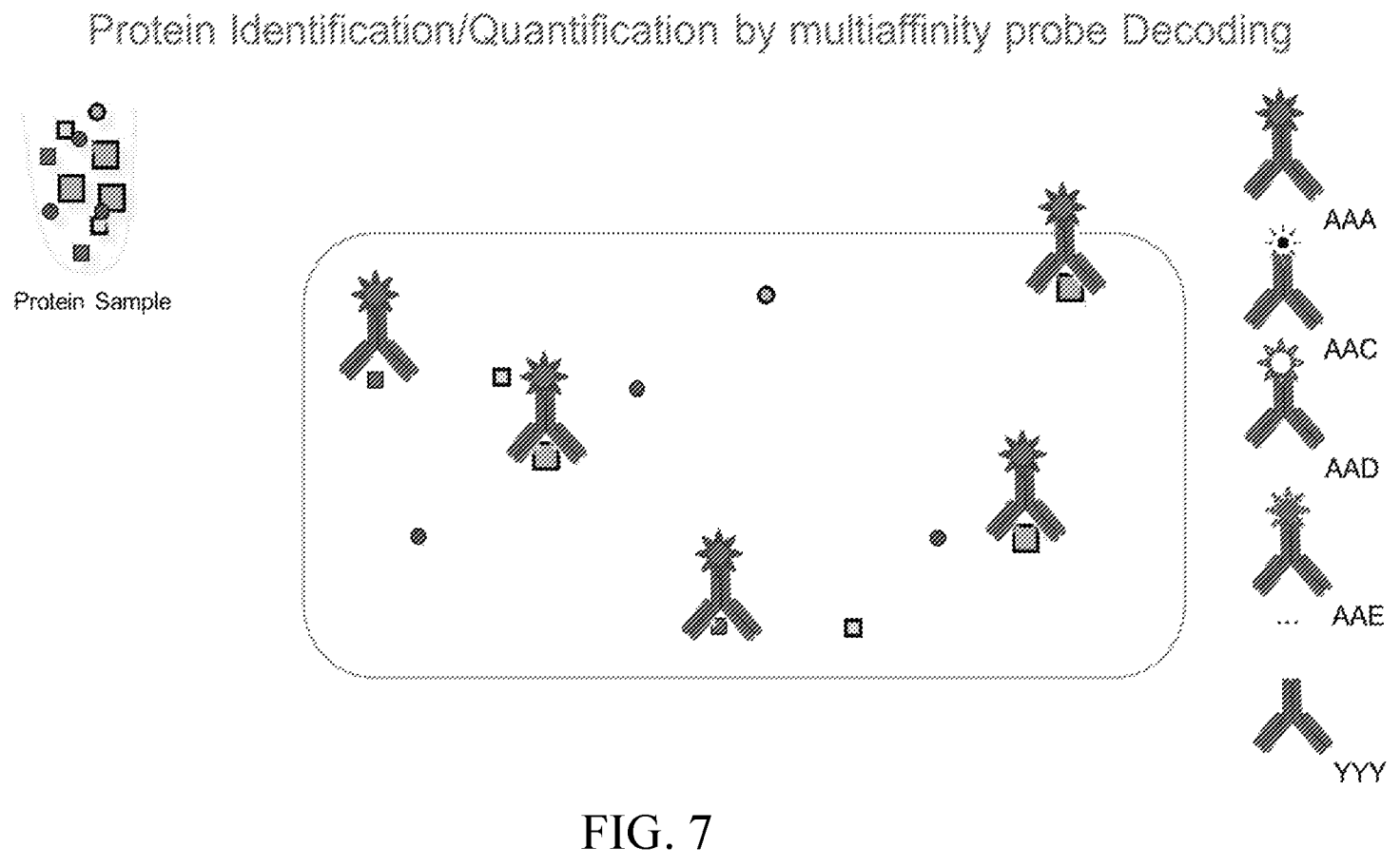
Figure 8:
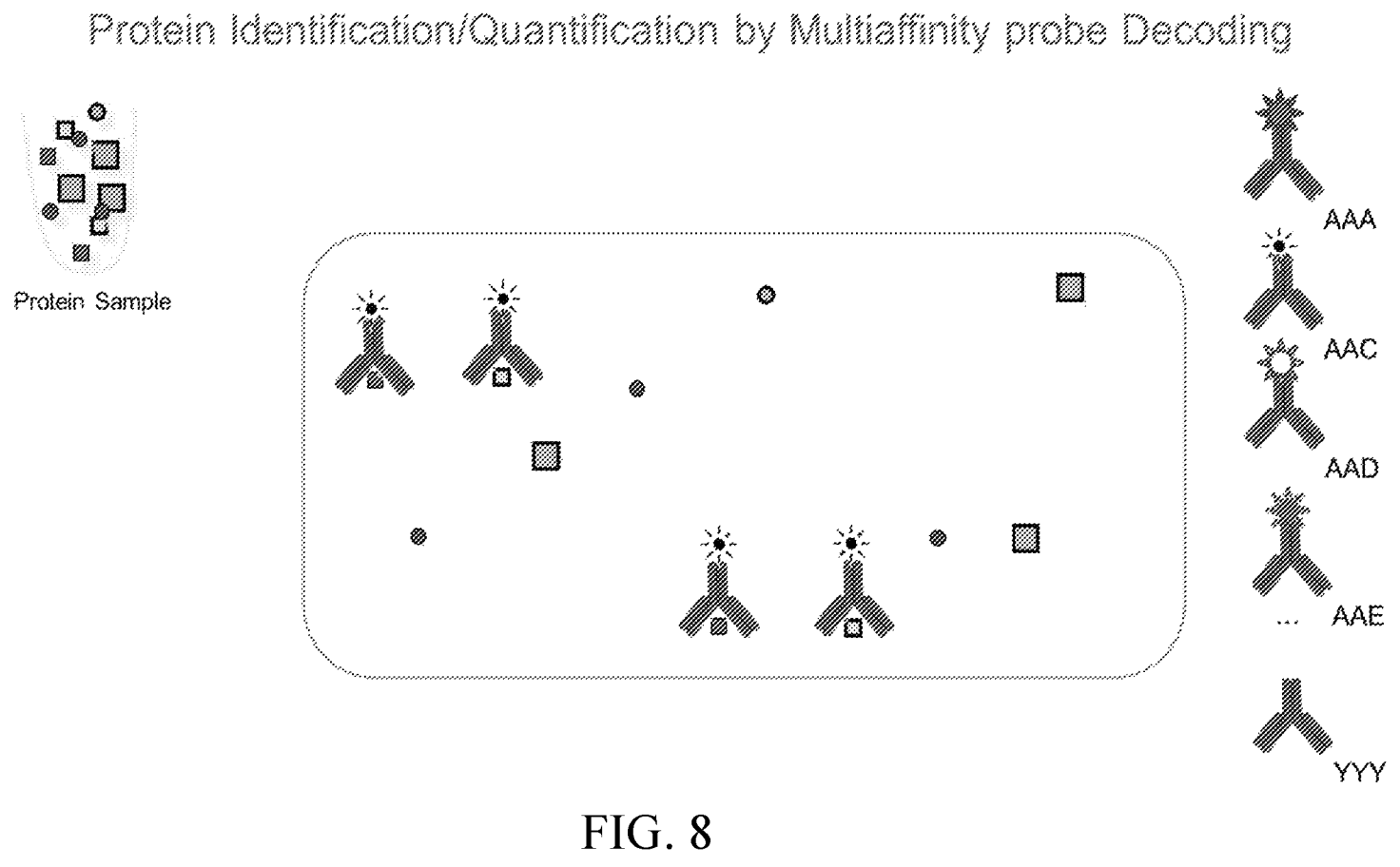
Figure 9:
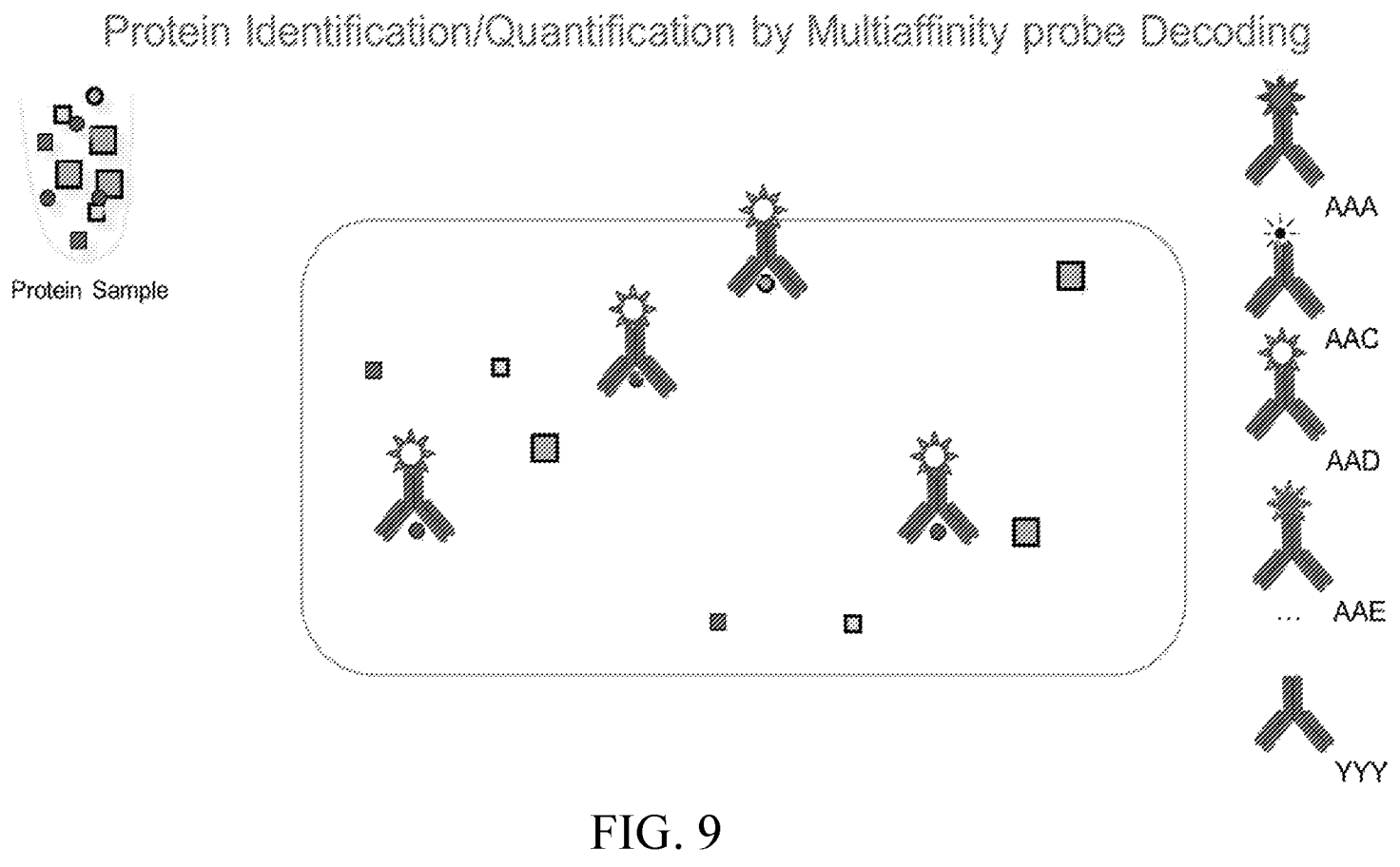

In some cases, multiple affinity reagents that are labeled with nucleic acid barcodes may be multiplexed and then detected using complementary nucleic acid probes (see FIG. 7, FIG. 8, and FIG. 9). A multiplexed group of affinity reagents may be detected in a single cycle using multiple complementary nucleic acids with distinct detection moieties. In some cases, a multiplexed group of affinity reagents may be detected in multiple cycles using a single complementary nucleic acid conjugated to a detection moiety. In some cases, a multiplexed group of affinity reagents may be detected in multiple cycles using multiple complementary nucleic acids each conjugated to a distinct detection moiety. In some cases, a multiplexed group of affinity reagents may be detected in multiple cycles using multiple complementary nucleic acids each conjugated to a distinct group detection moieties.

In some cases, one or more affinity reagents, that are labeled with nucleic acid barcodes, may be cross-linked to a bound protein. Once the one or more affinity reagents are cross-linked to the protein, the barcodes may be sequenced to determine the identity of the cross-linked affinity reagent. In some cases, multiple bound proteins may be exposed to the one or more affinity reagents. In some cases, when multiple bound proteins are cross-linked with one or more affinity reagents, the barcodes associated with the bound affinity reagents may be sequenced to determine the identity of the cross-linked affinity reagents associated with each of the multiple bound proteins.

The family of affinity reagents may comprise one or more types of affinity reagents. For example the methods of the present disclosure may use a family of affinity reagents comprising one or more of antibodies, antibody fragments, Fab fragments, aptamers, peptides, and proteins.

The affinity reagents may be modified. Modifications include, but are not limited to, attachment of a detection moiety. Detection moieties may be directly or indirectly attached. For example the detection moiety may be directly covalently attached to the affinity reagent, or may be attached through a linker, or may be attached through an affinity reaction such as complementary nucleic acid tags or a biotin streptavidin pair. Attachment methods that are able to withstand gentle washing and elution of the affinity reagent may be preferred. An attachment method can be reversible or irreversible.

Detection moieties include, but are not limited to, fluorophores, bioluminescent proteins, nucleic acid segments including a constant region and barcode region, or chemical tethers for linking to a nanoparticle such as a magnetic particle. Detection moieties may include several different flurophores with different patterns of excitation or emission.

The detection moiety may be cleavable from the affinity reagent. This can allow for a step in which the detection moieties are removed from affinity reagents that are no longer of interest to reduce signal contamination.

In some cases the affinity reagents can be unmodified. In some cases, an affinity reagent can be modified, for example by cleaving, tagging, phosphorylating, denaturing, or otherwise. In some cases, an affinity reagent can be modified to be detectable, such as by conjugation to an enzyme, a fluorophore, a radioactive particle, a magnetic particle, a colorimetric particle, or some other method.

In some cases, the affinity reagent can be detected. Detection can be via a microscope, a magnetic detector, film such as X-ray film, a CCD detector, visual detection, or by some other method. For example if the affinity reagent is an antibody then the presence of the antibody may be detected by atomic force microscopy. The affinity reagents may be unmodified and may be detected, for example, by having antibodies specific to one or more of the affinity reagents. For example if the affinity reagent is a mouse antibody then the mouse antibody may be detected by using an anti-mouse secondary antibody. Alternately the affinity reagent may be an aptamer which is detected by an antibody specific for the aptamer. The secondary antibody may be modified with a detection moiety as described above. In some cases the presence of the secondary antibody may be detected by atomic force microscopy.

In some examples, two or more affinity reagents may comprise the same modification, for example a conjugated green fluorescent protein, or may comprise two or more different types of modification. For example, each affinity reagent may be conjugated to one of several different fluorescent moieties, each with a different wavelength of excitation or emission. This may allow multiplexing of the affinity reagents as several different affinity reagents may be combined and/or distinguished.

In some cases, two or more affinity reagents can be conjugated to two or more fluorescent moieties. In such cases, the fluorescent moieties can be different, such that the affinity reagents can be detected without interference. For example, a first affinity reagent may be conjugated to a green fluorescent protein, a second affinity reagent may be conjugated to a yellow fluorescent protein and a third affinity reagent may be conjugated to a red fluorescent protein, thus the three affinity reagents can be multiplexed and identified by their fluorescence. In a further example a first, fourth and seventh affinity reagent may be conjugated to a green fluorescent protein, a second, fifth and eighth affinity reagent may be conjugated to a yellow fluorescent protein and a third, sixth and ninth affinity reagent may be conjugated to a red fluorescent protein; in this case the first, second and third affinity reagents may be multiplexed together while the second, fourth and seventh, and third, sixth and ninth affinity reagents form two further multiplexing reactions. The number of affinity reagents which can be multiplexed together may depend on the detection moieties used to differentiate them. For example, the multiplexing of affinity reagents labeled with fluorophores may be limited by the number of unique fluorophores available. For further example, the multiplexing of affinity reagents labeled with nucleic acid tags may be determined by the length of the nucleic acid bar code.

The specificity of each affinity reagent can be determined prior to use in an assay. The binding specificity of the affinity reagents can be determined in a control experiment using known proteins. Any appropriate experimental methods may be used to determine the specificity of the affinity reagent. In one example a substrate may be loaded with known protein standards at known locations and used to assess the specificity of a plurality of affinity reagents. In another example, a substrate may contain both experimental samples and a panel of controls and standards such that the specificity of each affinity reagent can be calculated from the binding to the controls and standards and then used to identify the experimental samples. In some cases affinity reagents with unknown specificity may be included along with affinity reagents of known specificity, data from the known specificity affinity reagents may be used to identify proteins, and the pattern of binding of the unknown specificity affinity reagents to the identified proteins may be used to determine their binding specificity. It is also possible to reconfirm the specificity of any individual affinity reagent by using the known binding data of other affinity reagents to assess which proteins the individual affinity reagent bound. Thus with multiple uses of an affinity reagent panel the specificities of the affinity reagents may be increasingly refined with each iteration. While affinity reagents that are uniquely specific to particular proteins may be used, methods described herein may not require them. Additionally, methods may be effective on a range of specificities. In some examples, methods described herein may be particularly efficient when affinity reagents are not specific to any particular protein, but are instead specific to amino acid motifs (e.g. the tri-peptide AAA). In some cases, an affinity reagent may bind specifically to a specific protein secondary or tertiary structure.

In some examples, one or more affinity reagents may be chosen to bind amino acid motifs of a given length, such as 2, 3, 4, 5, 6, 7, 8, 9, 10, or more than 10 amino acids. In some examples, one or more affinity reagents may be chosen to bind amino acid motifs of a range of different lengths from 2 amino acids to 40 amino acids.

In some examples, the affinity reagents may be chosen to have high, moderate, or low binding affinities. In some cases affinity reagents with low or moderate binding affinities may be preferred. In some cases the affinity reagents may have dissociation constants of about $10^{-3}$ M, $10^{-4}$ M, $10^{-5}$ M, $10^{-6}$ M, $10^{-7}$ M, $10^{-8}$ M, $10^{-9}$ M, $10^{-10}$ M or lower. In some cases the affinity reagents may have dissociation constants of greater than about $10^{-10}$ M, $10^{-9}$ M, $10^{-8}$ M, $10^{-7}$ M, $10^{-6}$ M, $10^{-5}$ M, $10^{-4}$ M, $\mathbf{10^{-3}}$ M, $\mathbf{10^{-2}}$ M or higher.

Some of the affinity reagents may be chosen to bind modified amino acid sequences, such as phosphorylated or ubiquinated amino acid sequences. In some examples, one or more affinity reagents may be chosen to be broadly specific for a family of epitopes that may be contained by one or more proteins. In some examples, one or more affinity reagents may bind two or more different proteins. In some examples, one or more affinity reagents may bind weakly to their target or targets. For example, affinity reagents may bind less than 10%, less than 10%, less than 15%, less than 20%, less than 25%, less than 30%, less than 35%, or less than 35% to their target or targets. In some examples, one or more affinity reagents may bind moderately or strongly to their target or targets. For example, affinity reagents may bind more than 35%, more than 40%, more than 45%, more than 60%, more than 65%, more than 70%, more than 75%, more than 80%, more than 85%, more than 90%, more than 91%, more than 92%, more than 93%, more than 94%, more than 95%, more than 96%, more than 97%, more than 98%, or more than 99% to their target or targets.

To compensate for weak binding, an excess of the affinity reagent may be applied to the substrate. The affinity reagent may be applied at about a 1:1, 2:1, 3:1, 4:1, 5:1, 6:1, 7:1, 8:1, 9:1 or 10:1 excess relative to the sample proteins. The affinity reagent may be applied at about a 1:1, 2:1, 3:1, 4:1, 5:1, 6:1, 7:1, 8:1, 9:1 or 10:1 excess relative to the expected incidence of the epitope in the sample proteins.

The affinity reagents may also comprise a magnetic component. The magnetic component may be useful for manipulating some or all bound affinity reagents into the same imaging plane or z stack. Manipulating some or all affinity reagents into the same imaging plane may improve the quality of the imaging data and reduce noise in the system.

Binding Measurements

Given a set of modified affinity reagents and a conjugated substrate, affinity reagents may be iteratively applied to the substrate. Measurements of the sample can be performed in cycles. Each measurement cycle can comprise several stages. In some cases, a first stage can comprise application of one or more affinity reagents to the substrate where they may adsorb to the conjugated proteins.

In some cases, the substrate can subsequently be lightly washed to remove non-specific binding. This washing step can be performed under conditions which will not elute affinity reagents which have bound to the immobilized proteins. Some examples of buffers which could be used for this step include phosphate buffered saline, Tris buffered saline, phosphate buffered saline with Tween20, and Tris buffered saline with Tween20.

Following adsorption, the binding address, which can be a spatially discernible location e.g., on a grid, for each modified affinity reagent are determined, such as through measurement of a fluorophore that has been conjugated to the affinity reagents directly, or to a complement nucleic acid to a nucleic acid strand conjugated to the affinity reagents. The detection method is determined by the choice of detection moiety. Fluorophores and bioluminescent moieties may be optically detected, in some cases secondary detection reagents are required. The unique address of each immobilized protein on the substrate may be determined prior to the binding measurements, or a list of addresses containing immobilized proteins may be generated through the binding measurements.

A detector may be used to detect binding measurements. The term "detector," as used herein, generally refers to a device that is capable of detecting a signal, including a signal indicative of the presence or absence of a binding event of an affinity reagent to a protein. The signal may be a direct signal indicative of the presence or absence of a binding event, such as a surface plasmon resonance (SPR) signal. The signal may be an indirect signal indicative of the presence or absence of a binding event, such as a fluorescent signal. In some cases, a detector can include optical and/or electronic components that can detect signals. Detectors may be used in detection methods. Non-limiting examples of detection methods include optical detection, spectroscopic detection, electrostatic detection, electrochemical detection, magnetic detection, fluorescence detection, surface plasmon resonance (SPR), and the like. Optical detection methods include, but are not limited to, fluorimetry and UV-vis light absorbance. Spectroscopic detection methods include, but are not limited to, mass spectrometry, nuclear magnetic resonance (NMR) spectroscopy, and infrared spectroscopy. Electrostatic detection methods include, but are not limited to, gel based techniques, such as, for example, gel electrophoresis. Electrochemical detection methods include, but are not limited to, electrochemical detection of amplified product after high-performance liquid chromatography separation of the amplified products.

Detection signals comprising information of binding events using a detector may comprise a detector error rate associated with the information of binding measurements. For example, the detector error rate may be obtained from specifications of one or more detectors used to acquire the information of binding measurements. In some embodiments, the detector error rate is set to an estimated detector error rate. In some embodiments, the estimated detector error rate is set by a user of the computer. The estimated detector error rate may have a value of less than about 0.001, about 0.001, about 0.002, about 0.003, about 0.004, about 0.005, about 0.006, about 0.007, about 0.008, about 0.009, about 0.01, about 0.02, about 0.03, about 0.04, about 0.05, about 0.06, about 0.07, about 0.08, about 0.09, about 0.1, or more than about 0.1. Such an error rate may encompass a physical detector error. Alternatively, such an error rate may be attributable to a failure of a probe to "land on" a protein. For example, a probe may fail to "land on" or bind a protein when a probe is stuck in the system and not washing out properly. Alternatively or in combination, a probe may fail to "land on" or bind a protein when a probe binds to a protein that was not expected based on previous qualification and testing of the probes. Hence, the detector error rate may comprise a physical detector error rate, an off-target binding rate, an error rate due to stuck probes, or a combination thereof.

Detection of protein binding may be performed using fluorescence microscopy techniques suitable for imaging biological macromolecules (e.g., proteins and DNA) and cells. For example, protein binding may be performed using an air or an oil immersion microscopy method, such as that used in a conventional microscopy, holographic microscopy, or tomographic imaging. Microscopy techniques may use near-field, far-field, wide-field, and/or confocal imaging modes to achieve a high resolution of acquiring signals of interest, such as protein binding images. In some embodiments, such techniques may be used with conjunction with one or more fluorophores. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, R-Phycoerythrin, Allophcocyanin, or any other fluorophores . . . . The microscopy method may use a lens having a low magnification and/or a low numerical aperture (NA) to achieve a sufficiently large field of view (FOV) and depth of field at a desired spatial resolution of imaging. In some embodiments, the magnification of the imaging device may be about 1×, about 4×, about 5×, about 10×, about 20×, about 30×, about 40×, about 50×, about 60×, about 63×, about 80×, about 100×, about 150×, or more than about 150×. In some cases, the magnification may be between about 4× and about 200×, between about 4× and about 100×, between about 2× and about 80×, between about 10× and about 80×, between about 10× and about 40×, between about 20× and about 30×, or between about 4× and about 20×. In some embodiments, the magnification may range between a first magnification that is less than 4× and a second magnification that is more than 80×. In some embodiments, the magnification may range between a first magnification that is less than 4× and a second magnification that is more than 100×. For example, the imaging device may have a numerical aperture of more than 1.5, about 1.5, about 1.47, about 1.3, about 1.2, about 1.1, about 1, about 0.9, about 0.8, about 0.7, about 0.6, or less than about 0.6. In some cases, the numerical apertures may be greater than about 0.7, about 0.8, about 0.9, about 1, about 1.1, about 1.2, about 1.3, or about 1.4. An imaging device with a sufficiently large FOV may be used to simultaneously to acquire images of at least 10, at least 50, at least 100, at least 500, at least 1000, at least 5000, at least 10000, at least 100,000, at least 1,000,000 or more than 1,000,000 proteins simultaneously within a single field of view (FOV). The FOV may be a wide FOV. For example, the field of view may have a dimension of less than about 1 μm, about 1 μm, about 5 μm, about 10 μm, about 50 μm, about 100 μm, about 500 μm, about 1 mm, about 5 mm, about 10 mm, or more than about 10 mm. In some cases, the size of the field of view may be less than about 1 $μm^2$, about 1 $μm^2$, about 5 $μm^2$, about 10 $μm^2$, about 50 $μm^2$, about 100 $μm^2$, about 500 $μm^2$, about 1 $mm^2$, about 5 $mm^2$, about 10 $mm^2$, or more than about 10 $mm^2$. In some cases, the size of the field of view may be between about 10 $μm^2$ and about 10 $mm^2$; about 100 $μm^2$ and about 1 $mm^2$; about 100 $μm^2$ and about 10 $mm^2$; about 1000 $μm^2$ and about 5 $mm^2$; about 0.1 $mm^2$ and about 10 $mm^2$; about 0.5 $mm^2$ and about 5 $mm^2$; or about 0.5 $mm^2$ and about 1 $mm^2$. The imaging device may acquire images of binding measurements with a spatial resolution of less than about 100 nm, about 100 nm, about 500 nm, about 1 μm, about 5 μm, about 10 μm, about 50 μm, about 100 μm, about 500 μm, about 1 mm, or more than about 1 mm. The imaging device may acquire images of binding measurements with a spatial resolution of between about 100 nm and about 1 mm, between about 500 nm and about 10 μm, between about 50 nm and about 100 μm, between about 250 nm and about 750 nm, between about 300 nm and about 700 nm, or between about 100 nm and about 650 nm. The imaging device may be configured to gather z-stacks of images to generate three-dimensional images from acquired two-dimensional images. The imaging device may use an immersion lens. For example, the imaging device may use a water immersion lens, or an oil immersion lens. In some cases, the imaging device may use total internal reflection microscopy.

Images obtained using the systems and methods described herein may be processed or enhanced by performing one or more image analysis methods. Image analysis methods may be implemented using, for example, C, C++, ImageJ, Java, Matlab, Octave, Perl, Python, R, or a combination thereof. Image analysis method may be adapted from methods for processing fluorescence microscopy images of biological macromolecules (e.g., DNA, proteins) and/or cells. In some embodiments, image analysis method may be configurable to process two-dimensional and/or three-dimensional images. In some embodiments, image analysis methods may be fully automated and/or tunable by a user. In some embodiments, image analysis methods may allow high throughput of obtaining accurate binding measurements of proteins. For example, images may be acquired with a speed-up of at least about 1.25 times, about 1.5 times, 2 times, at least about 5 times, at least about 10 times, at least about 15 times, at least about 20 times, at least about 25 times, at least about 30 times, at least about 35 times, at least about 40 times, at least about 45 times, at least about 50 times, at least about 100 times, or more than 100 times, as compared to manual or semi-automated methods of acquiring binding measurements.

Image analysis methods may comprise performing a deconvolution of the acquired images. The deconvolution step may improve or enhance the contrast and/or resolution of binding measurement images for further image processing or analysis. For example, the deconvolution step may reduce or eliminate out-of-focus blur or other sources of signal noise in the acquired images, thereby enhancing the signal-to-noise ratio (SNR) of images. In some embodiments, the image analysis methods may comprise an iterative or non-iterative deconvolution of the image. For example, the image analysis methods may comprise at least 1, 2, 3, 4, 5, 6, 7, 8, 9, 10, or more than 10 iterations of deconvoluting the image.

In some cases, image analysis methods can comprise registration of one or more images. Registration can be performed manually or automatically. In some cases, automatically registered images can be manually checked or adjusted.

In some cases, image analysis methods can comprise selection of a region of interest. A region of interest can be selected by a user generally indicating a region of interest, a user outlining or tracing a region of interest, a user segmenting a region of interest, or automatic segmentation of a region of interest.

Image analysis methods may further comprise processing the images to extract a set of one or more features. For example, such sets of features may be selected to enable high performance (e.g., accuracy, throughput, sensitivity, specificity, etc.) and/or high throughput of acquiring binding measurements of interest. Physical features of proteins may be extracted, such as area, count, diameter, perimeter length, volume, size, etc. Image parameter features may also be extracted, such as brightness, color, contrast, correlation, entropy, energy, homogeneity, uniformity, etc. Feature sets may be stored as vectorized, scalar, categorical, or digital values (e.g., absolute or normalized). For example, categorical values (e.g., representing brightness) may be selected from a set of two or more categories, such as {"high", low}, {"on", "off"}, {"high", "medium", "low}, or {" high ", "medium", "low", or "zero"}. For example, digital values (e.g., representing brightness) may be selected from a set of two or more discrete values, such as {0, 1}, {0, 1, 2}, {0, 1, 2, 3}, {0, 1, 2, 3, 4}, etc. Digital values (e.g., representing brightness) may be represented using 1 bit, 2 bits, 3 bits, 4 bits, 5 bits, 6 bits, 7 bits, 8 bits, 9 bits, 10 bits, about 12 bits, about 16 bits, about 24 bits, about 32 bits, about 64 bits, about 128 bits etc.

Image analysis methods may analyze acquired image data to generate an output of measured protein binding. For example, the image analysis method may apply a prediction algorithm (e.g., a predictive analytics algorithm) to the acquired data to generate output of estimated or measured protein binding. The prediction algorithm may comprise an artificial intelligence based predictor, such as a machine learning based predictor, configured to process the acquired image data to generate the output of estimated or measured protein binding. The machine learning predictor may be trained using datasets from one or more sets of images of known protein binding as inputs and known protein binding data as outputs to the machine learning predictor.

The machine learning predictor may comprise one or more machine learning algorithms. Examples of machine learning algorithms may include a support vector machine (SVM), a naïve Bayes classification, a random forest, a neural network, deep learning, or other supervised learning algorithm or unsupervised learning algorithm for classification and regression. The machine learning predictor may be trained using one or more training datasets corresponding to image data.

The machine learning predictor may be trained until certain predetermined conditions for accuracy or performance are satisfied, such as having minimum desired values corresponding to estimating or measuring protein binding. For example, the protein binding accuracy measure may correspond to estimated or actual protein binding measurements. Examples of protein binding accuracy measures may include sensitivity, specificity, positive predictive value (PPV), negative predictive value (NPV), accuracy, and area under the curve (AUC) of a Receiver Operating Characteristic (ROC) curve.

For example, such a predetermined condition may be that the sensitivity of identifying a bound protein of interest comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the specificity of identifying a bound protein of interest comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the positive predictive value (PPV) of identifying a bound protein of interest comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the negative predictive value (NPV) of identifying a bound protein of interest comprises a value of, for example, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99%.

As another example, such a predetermined condition may be that the area under the curve (AUC) of a Receiver Operating Characteristic (ROC) curve of identifying a bound protein of interest comprises a value of at least about 0.50, at least about 0.55, at least about 0.60, at least about 0.65, at least about 0.70, at least about 0.75, at least about 0.80, at least about 0.85, at least about 0.90, at least about 0.95, at least about 0.96, at least about 0.97, at least about 0.98, or at least about 0.99.

Empirical measurement data (e.g., binding measurements) may be processed using deconvolution methods to perform deconvolution of the empirical measurement data to identify one or more proteins contained within a sample of unknown proteins. The deconvolution algorithms may use iterative methods, non-iterative methods, or a combination thereof. The deconvolution may comprise receiving binding measurements of each of a plurality of affinity reagent probes to unknown proteins in the sample. Each affinity reagent probe may be configured to selectively bind to one or more candidate proteins among a plurality of candidate proteins. The deconvolution method may comprise comparing (e.g., iteratively or non-iteratively) information of empirical measurements (e.g., binding measurements) against a database of protein sequences corresponding to candidate proteins. For example, the information of empirical measurements may be deconvolved into signal profiles that match profiles of one or more candidate proteins in the database. For each of one or more candidate proteins, the deconvolution may comprise generating a likelihood that each of the candidate proteins is present the sample, based on the comparison of empirical measurements (e.g., binding measurements) of the candidate proteins against the database. The deconvolution method may comprise excluding a portion of the candidate proteins from further consideration or analysis based on a determination that the portion of candidate proteins is not present in the sample.

The deconvolution method may account for affinity reagents that have a likelihood of binding to off-target sites, such as random off-target sites or biosimilar off-target sites. Random off-target sites may refer to an off-target site randomly chosen from a set of possible targets (e.g., a string of three random amino acids to form a trimer epitope). Bio-similar off-target sites may refer to an off-target site with a high degree of similarity (e.g., as measured by Hamming distance) to a target epitope. For example, an affinity reagent with an epitope of LLL may have a higher likelihood (e.g., about 0.45, about 0.4, about 0.35, about 0.3, about 0.25, about 0.2, about 0.15, or about 0.1) of binding to random off-target sites (e.g., YAD, FPV, HMW, GPF, and CLE) as compared to a likelihood (e.g., about 0.45, about 0.4, about 0.35, about 0.3, about 0.25, about 0.2, about 0.15, about 0.1, about 0.05, or about 0.01) of binding to biosimilar off-target sites (e.g., LLM, LML, LLI, ILL, LIL). The deconvolution method may account for such likelihoods (e.g., probabilities) of binding of an affinity reagent (e.g., probe) to random off-target sites and biosimilar off-target sites.

After binding measurements are acquired and analyzed, the affinity reagents can be desorbed through a more stringent wash. This wash step may remove some or all affinity reagents from the immobilized substrates. In some cases affinity reagents may have been chosen to have low to moderate binding affinities to facilitate removal. Used affinity reagents may be re-captured for reuse or discarded. In examples where affinity reagents with cleavable detection moieties are used, the detection moieties may be cleaved and removed at this stage. Following stringent washing, in some examples, any remaining fluorescence can be quenched and even more stringent washing applied to remove leftover affinity reagent. Carry-over/contamination can be detected by reimaging the substrate before applying the next affinity reagent. Contamination may also be detected by monitoring consecutive for images for recurring signals. This concludes one cycle of analysis.

In some embodiments the fluorescently tagged affinity reagents may be quenched by exposure to prolonged intense light at the activation wavelength. Quenching of the fluorescent tags may replace or supplement washing steps to remove the affinity reagents. In some embodiments, it may be desirable to cycle n fluorophores to distinguish which signals were derived from the previous n–1 cycles.

Figure 10:
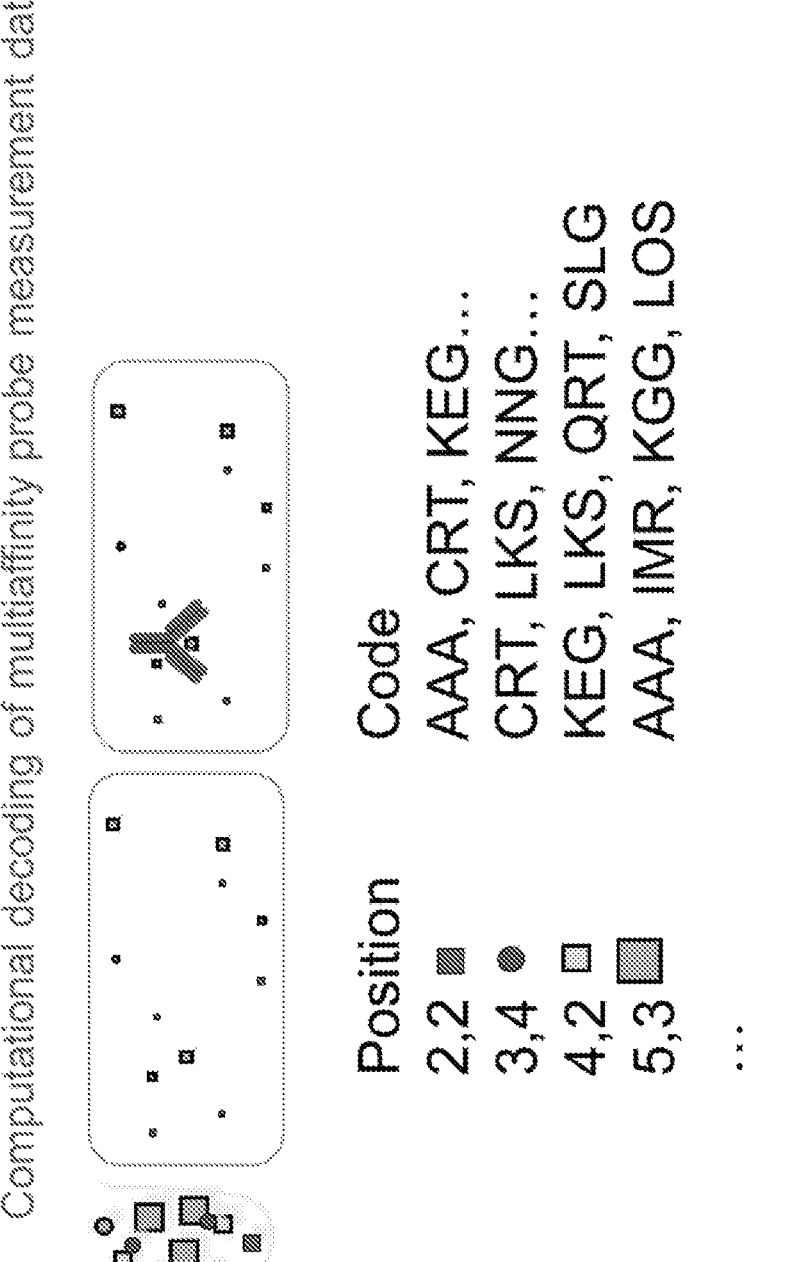
FIG. 10 illustrates computational decoding of antibody measurement data, in accordance with some embodiments.

Cycles may continue for each affinity reagent, or multiplexing thereof. The result of the measurement phase may be a very large table listing the binding coordinates for each affinity reagent, or the affinity reagents which bound at each coordinated location, as shown in, for example, FIG. 10.

In some cases, the affinity reagents may have low, moderate, or high affinity for their targets. In some cases, the affinity reagents may have low or moderate affinity for their targets. In some cases, affinity reagents with low or moderate affinity may attach and detach from different targets more rapidly than desired for the imaging step. In some cases, it may be desirable to alter the off-rate of one or more of the affinity reagents, where the off-rate can be the rate at which an affinity reagent can dissociate from a bound target.

In some cases, the substrate with attached, spatially separated, individual, protein molecules may be covered in a gel. In some cases, a gel covering the substrate and proteins may be a low, or very low, percentage gel. For example the gel may be about a 2%, 1.5%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% gel. The gel may be formed from any suitable compound. For example, the gel may be an agarose gel, a PAGE gel, an acrylamide gel, a bisacrylamide gel, or a di-sulfo bisacrylamide gel. In some cases, the gel may be formed on the substrate after the proteins have been attached. In some cases, the gel may be formed on the substrate before the proteins have been attached.

In some cases, it may be desirable to chemically link an affinity reagent to a bound protein. An affinity reagent may be cross linked to a protein it has bound so that even after it disassociates from the protein it remains in the immediate vicinity and may be detected in the imaging step at the same 'address' as the originally bound protein. The cross linking agent may include a bond which can be reversed, for example a photocleavable bond or a bond targeted by a specific enzyme. In some cases, the cross link may be broken or reversed by a chemical or physical change, for example adding a specific chemical, changing the pH or changing the temperature.

In some embodiments, the spatially separated individual protein molecules can be located in wells on the surface of the substrate. In some cases, it may be possible to seal, close or cap the wells on the substrate such that an affinity reagent bound to a particular individual protein remains trapped in the well of that particular individual protein molecule. In some cases, wells may be open during the affinity reagent binding step, and an initial washing step, and then may be closed during an imaging step.

In some cases, the affinity reagents may be bound to magnetic beads. In some cases, the affinity reagents may be bound to magnetic nanobeads or microbeads. In such cases, a magnetic field may be applied to the substrate to immobilize the affinity reagents in the immediate vicinity of the bound protein.

In some cases, the off-rate of the affinity reagent may be decreased by altering the temperature of the assay. For example the affinity reagent may be applied to the substrate in a buffer at room temperature, or 25° C., and after the affinity reagent has bound to a protein molecule on the substrate the temperature of the assay may be decreased to 15° C., 10° C., 5° C., 4° C., 3° C., 2° C., 1° C. or lower than 1° C. In some cases, the buffer on the substrate may be frozen to immobilize the affinity reagents.

In some cases, the affinity reagents can have fluorescent labels and may be detected by fluorescent imaging. After each round of binding, images may be taken to show where the affinity reagents bound. In some cases, a single image is taken of the entire substrate. In some cases, multiple images may be taken which cover different portions of the substrate. Each image of the multiple images may comprise a fiducial, and/or positive and negative controls. In some cases, each image of the multiple images comprises a distinct, non-overlapping, region of the substrate. In some cases, each image of the multiple images overlaps with other images. In such cases, images which overlap can comprise an overlapping area of at least 10%, 20%, 30%, 40%, 50%, 60%, 70%, or 80% of the size of the image. In some cases, the binding of a particular binding reagent at each distinct individual protein molecule may be depicted in 1, 2, 3, 4, 5, 6, 7, 8, 9, 10 or more than 10 different images.

For each individual spatially isolated protein molecule on the substrate data may be compiled regarding the affinity reagents which were detected at that spatial address. Once a particular affinity reagent has been observed to bind an individual protein molecule the likelihood of that protein containing various epitopes can be determined from the known binding properties of the affinity reagent. For example, if a particular affinity reagent is known to bind 3 different epitopes with about equal probability, then any protein which is bound by that affinity reagent has about 33% chance of containing any one of the three epitopes. In some cases, the probability may be decreased to allow for off target binding. For example, if a particular affinity reagent is known to bind 3 different epitopes with about equal probability but is also known to bind random sequences in about 4% of cases, then any protein which is bound by that affinity reagent has about 32% chance of containing any one of the three epitopes. In another example, if a particular affinity reagent is known to bind a single epitope, AAA, in about 60% of cases, and to bind to random sequences in about 40% of cases, then each protein which is observed to be bound by the affinity reagent has a 60% chance of containing the epitope AAA.

Analysis

A further step in protein identification may comprise a software tool to determine the most likely identity of each protein at each coordinate of the substrate from the information about which affinity reagents bound to that coordinate. In some cases, the identity of a protein can be determined with at least 50%, 60%, 70%, 80%, 90%, 95%, or 99% confidence. In some cases, the identity of a protein can be determined with at least 50%, 60%, 70%, 80%, 90%, 95%, or 99% accuracy. In some cases, the analysis or the whole protein identification process can be repeated to confirm the identity of a protein. In some cases, a protein can be identified using two or more affinity reagents to increase the confidence or the accuracy of the identity of that protein.

A software may utilize information about the binding characteristics of each affinity reagent. For example, if a given affinity reagent preferentially binds to proteins containing the tri-peptide epitope AAA. Given the information about the binding characteristic of each affinity reagent, a database of the proteins in the sample, and list of binding coordinates, the pattern of binding, the software tool can assign a probable identity to each coordinate as well as a confidence for that identity. In the extreme case of precise 1-1 mappings between affinity reagents and proteins, this can be accomplished with a simple lookup table. However, in the case where binding is more complex, this may be performed via solving the appropriate satisfaction problem. In cases where the binding characteristics are highly complex, an expectation maximization approach may be employed.

The software can utilize a listing of some or all locations in which each affinity reagent did not bind, and can use this information about the absence of epitopes to determine the protein present. The software can utilize information about which affinity reagents did and did not bind to each address.

Thus the software can use the information about both which epitopes were present and which epitopes were not present. The software may comprise a database. The database can comprise sequences of some or all known proteins in the species from which the sample was obtained. In some cases, a database can comprise partial sequences, for example in cases where the full sequence of a protein is unknown or variable. In some cases, a database can comprise sequences of proteins from related species. In some cases, a database can comprise other information about the proteins, such as structural information, expression information, or binding information. For example if the sample is known to be of human origin then a database with the sequences of some or all human proteins may be used. If the species of the sample is unknown then a database of some or all protein sequences may be used. The database may also contain the sequences of some or all known protein variants and mutant proteins, and the sequences of some or all possible proteins that could result from DNA frameshift mutations (see FIG. 12). The database may also contain sequences of possible truncated proteins that may arise from premature stop codons, or from degradation.

The software may comprise one or more algorithms, such as a machine learning, deep learning, statistical learning, supervised learning, unsupervised learning, clustering, expectation maximization, maximum likelihood estimation, Bayesian inference, linear regression, logistic regression, binary classification, multinomial classification, or other pattern recognition algorithm. For example, the software may perform the one or more algorithms to analyze the information (e.g., as inputs of the one or more algorithm) of (i) the binding characteristic of each affinity reagent, (ii) the database of the proteins in the sample, (iii) the list of binding coordinates, and/or (iv) the pattern of binding of affinity reagents to proteins, in order to generate or assign (e.g., as outputs of the one or more algorithms) (a) a probable identity to each coordinate and/or (b) a confidence (e.g., confidence level and/or confidence interval) for that identity. Examples of machine learning algorithms may include support vector machines (SVMs), neural networks, convolutional neural networks (CNNs), deep neural networks, cascading neural networks, k-Nearest Neighbor (k-NN) classification, random forests (RFs), and other types of classification and regression trees (CARTs).

The software may be trained by performing the methods of this disclosure on a substrate where the identity of the protein at each address is predetermined. For example the software may be trained using a Nucleic Acid-Programmable Protein Array or epitope tiling array as a training dataset.

The software may utilize a listing of sequences of all possible proteins in a proteome of the sample. For example, if the same comprised human cells then the software may utilize a listing of sequences of all known or predicted human proteins. In some cases, the software may also utilize a listing of sequences of known or predicted protein fragments. In some cases, proteins may have been crosslinked during sample preparation. In such cases, it may be useful for the software to use a table of all possible composite sequences of 2, 3, 4, 5, 6, 7, 8, 9, or 10 proteins.

In some cases, the software may be able to identify the parent protein of a protein fragment. In some case, the software may also be able to identify an approximate length of a protein fragment. For example if the parent protein contains two unique affinity reagent epitopes and only one of the unique epitopes is present in the fragment then the software may be able to predict that the fragment has been cleaved from the parent protein at a location between the two unique epitopes.

Determining Characteristics of Sample

Once decoding is complete, the probable identities of the proteins conjugated to each address are defined. Consequently, their abundance in the mixture can be estimated by counting observations (See FIG. 11). Thus a listing of each protein present in the mixture, and the number of observances of that protein can be compiled.

Further, if a photo-cleavable linker, or other form of specifically cleavable linker, is used to attach the proteins to the substrate then specific proteins of interest may be released from the substrate and collected for further study. For example specific proteins may be identified and eluted for further study. The methods of this disclosure may also serve as a way to purify and/or isolate a desired protein from a mixture. In some cases the method may be able to purify and/or isolate specific isotypes or post translationally modified proteins. In samples for which a complete list of possible proteins and associated sequences is not available this method may be able to distinguish different proteins of distinguish groups of proteins, these could then be eluted for further study. For example, for highly complex samples containing many unknown proteins, such as gut microbiome samples, the methods described herein may be used to fractionate the sample prior to mass spectrometry. In some cases proteins may be eluted from the substrate once their identities can be called. Removing the proteins from the substrate as they are identified allows subsequent rounds of affinity reagent binding to continue for the proteins whose identities cannot yet be called, and may decrease background noise and off target signals for the remaining rounds. In some examples one or more affinity reagents with specificity to particular proteins may be used as a first round to identify high abundance proteins such as serum albumin or immunoglobulins in a blood sample, these high abundance proteins may then be removed early in the process. In some cases a subset of the proteins on the substrate may be removed after every round of affinity reagent binding, or after every second, third, fourth, fifth, sixth, seventh, eighth, ninth, tenth, fifteenth, twentieth or more than twentieth round of affinity reagent binding. The signal to noise ratio may increase after each round of protein elution.

In some cases, unidentified proteins may be grouped or clustered based on their binding patterns. For example, in some cases, proteins present in the sample may not be represented in the sequence database. Unidentified proteins may be clustered into groups based on their binding patterns to the affinity probes with the goal of each group containing a set of unknown proteins in the sample with the same sequence. Protein quantities may be estimated for each group and included in quantitative analyses including, but not limited to, differential quantification between healthy and disease states, longitudinal analysis, or biomarker discovery. In some cases, an unidentified group may be selectively removed from the substrate for identification by mass spectrometry. In other cases, the unidentified group may be identified by performing further binding affinity measurement experiments specifically designed to generate confident identification.

In some cases after a protein or set of proteins have been removed it may be possible to add additional sample to the substrate. For example serum albumin is a high abundance protein in blood serum which may account for about half the protein in a sample, removing serum albumin after a first round of affinity reagent binding may allow the addition of further blood sample to the substrate. In some embodiments it may be preferred to remove high abundance proteins prior to immobilizing a sample on a substrate, for example through immunoprecipitation or affinity column purification.

Protein modifications may be identified using the methods of this disclosure. For example, post translational modifications may be identified by iterative cycles of detection using modification specific detection reagents interspersed with enzymatic processing (for example phosphatase treatment). Affinity reagents specific for different modifications may be used to determine the presence of absence of such modifications on the immobilized proteins. The method also allows quantification of the number of instances of each protein with and without a given modification.

Mutations in proteins may be detected by matching inconsistencies between the binding pattern of a sample protein and the predicted protein identity. For example an immobilized protein or polypeptide on the substrate which matches the affinity reagent binding profile of a known protein except for the binding of one affinity reagent may have an amino acid substitution. As affinity reagents may have overlapping epitopes an immobilized protein may have several mismatches from the predicted affinity binding pattern despite having a single amino acid substitution. DNA mutations which cause frameshifts of premature stop codons may also be detected.

Figure 13:
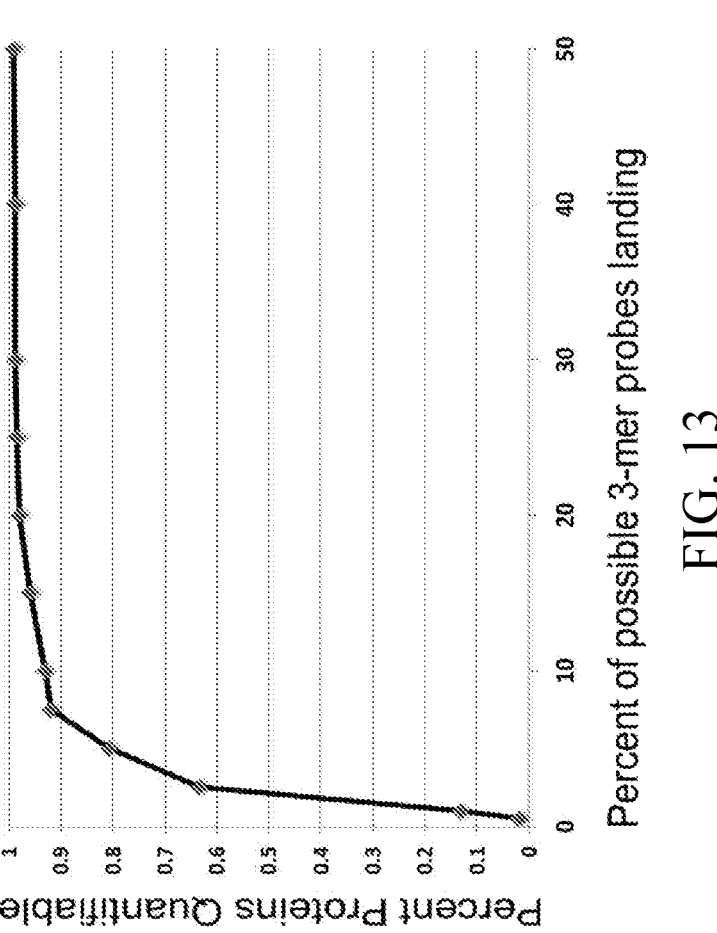
FIG. 13 illustrates coverage of 3-mer multiaffinity antibody sampling that may be required for quantification, in accordance with embodiments.

The number of affinity reagents required may be less than the total number of epitopes present in the sample. For example if the affinity reagents are selected such that each affinity reagent recognizes one unique three peptide epitope then the total set of affinity reagents to recognize all possible epitopes in the sample is 20×20×20=8000. However the methods of the present disclosure may only require about 100, 200, 300, 400, 500, 600, 700, 800, 900, 1000, 1500, 2000, 2500, 3000, 3500, 4000, 4500, 5000, 5500 or 6000 of these affinity reagents. In some cases the methods may only require less than about 500, 1000, 2500, 3000, 3500, 4000, 4500, 5000, 5500 or 6000 affinity reagents. FIG. 13 shows the results of a simulation demonstrating the percentage of known human proteins that can be identified given a set of x affinity reagents specific to unique amino acid 3-mers as a function of the binding efficiency of each affinity reagent. As seen in FIG. 13, 98% of human proteins can be uniquely identified with 8000 3-mer affinity reagents, and a binding likelihood of 10%.

The methods of the present disclosure may be highly accurate. The methods of the present disclosure may be able to identify each protein with about 90%, 91%, 92%, 93%, 94%, 95%, 96%, 97%, 98%, 98.5%, 99%, 99.5% 99.9% or more than 99.9% accuracy.

The methods of the present disclosure may be able to predict the identity of each protein with about 90%, 91%, 92%, 93%, 94%, 95%, 96%, 97%, 98%, 98.5%, 99%, 99.5% 99.9% or more than 99.9% confidence. The degree of confidence may be different for different proteins within the sample. For example proteins with very unique sequences may be identified with higher confidence than proteins which are highly similar to other proteins. In some cases a protein may be identified as part of a family of proteins with high confidence, however the exact identity of the protein may be predicted with lower confidence. In some cases proteins that are extremely large or extremely small may be predicted with lower confidence than proteins of more moderate size.

In some cases a protein may be identified as part of a family of proteins with high confidence, however the exact identity of the protein may be predicted with lower confidence. For example, a protein containing a single amino acid variant may be difficult to resolve from the canonical form of the protein with high confidence. In this case, neither the canonical sequence nor the single amino acid variant-containing form may have high confidence, but a high confidence can be assessed to the unknown protein being part of the group of proteins containing both sequences. A similar case may occur in instances where a protein may have multiple related isoforms with similar sequence.

The methods of the present disclosure may be able to identify some or all proteins in a given sample. The methods of the present disclosure maybe able to identify about 90%, 91%, 92%, 93%, 94%, 95%, 96%, 97%, 98%, 98.5%, 99%, 99.5% 99.9% or more than 99.9% of proteins in a sample.

The methods of the present disclosure may be able to rapidly identify proteins in a sample. The methods of the present disclosure may be able to identify more than about 100, about 1000, about 5000, about 10000, about 20,000, about 30,000, about 40,000, about 50,000, about 100,000, 1,000,000, about 10,000,000, about 100,000,000, about 1,000,000,000, about 10,000,000,000, about 100,000,000, 000, about 1,000,000,000,000 proteins per flowcell per day. The methods of the present disclosure may be able to identify more than about 1010, 1011, 1012, 1013, 1014, 1015, 1016, 1017, or more than about 1017 proteins per flowcell per day. The methods of the present disclosure may be able to identify about 1010-1012, 1011-1014, 1012-1016, or 1013-1017 proteins per flowcell per day. The methods of the present disclosure may be able to identify more than 95% of the proteins within about 10 pg, about 20 pg, about 30 pg, about 40 pg, about 50 pg, about 60 pg, about 70 pg, about 80 pg, about 90 pg, about 100 pg, about 300 pg, about 300 pg, about 400 pg, about 500 pg, about 600 pg, about 700 pg, about 800 pg, about 900 pg, about 1 ng, about 2 ng, about 3 ng, about 4 ng, about 5 ng, about 6 ng, about 7 ng, about 8 ng, about 8 ng, about 10 ng, about 10 ng, about 20 ng, about 30 ng, about 40 ng, about 50 ng, about 60 ng, about 70 ng, about 80 ng, about 90 ng, about 100 ng, about 300 ng, about 300 ng, about 400 ng, about 500 ng, about 600 ng, about 700 ng, about 800 ng, about 900 ng, about 1 μg, about 2 μg, about 3 μg, about 4 μg, about 5 μg, about 6 μg, about 7 μg, about 8 μg, about 8 μg, about 10 μg, about 10 μg, about 20 μg, about 30 μg, about 40 μg, about 50 μg, about 60 μg, about 70 μg, about 80 μg, about 90 μg, about 100 μg, about 300 μg, about 300 μg, about 400 μg, about 500 μg, about 600 μg, about 700 μg, about 800 μg, about 900 μg, or more than about 1 mg of protein per flowcell per day.

Applications

The methods of the present disclosure may be used to assess a proteome, for example after an experimental treatment. The methods of the present disclosure may be used to assess the effect of a therapeutic intervention, such as efficacy, toxicity, duration of effect, or other effect.

The methods of the present disclosure may be used for biomarker discovery. Monitoring proteome expression in subjects with and without disease may lead to the identification of biomarkers. In some cases, a biomarker can be a protein which can be increased or decreased in a subject with a disease compared with a subject without the disease. Monitoring proteome expression in subjects prior to developing a disease, or in subjects at risk of developing a disease may identify biomarkers that predict risk. Evaluating the proteome expression of a subject may indicate the health of the subject or the risk of developing certain diseases or disorders. The methods of this disclosure may be used to evaluate therapies, or differentiate drug/therapy responders from non-responders. The methods of this disclosure may be of particular use for personalized medicine.

In some cases, the methods of the present disclosure may be used in clinical trials. For example, in a clinical trial to determine efficacy of a medication protein samples may be collected from the subjects in both treatment and control groups, before, during and after the experimental/or vehicle treatment. The protein expression data may be analyzed together with the disease progression data from the clinical trial to determine whether the protein expression data can be used to stratify the subjects, or to predict subjects who will or won't respond well to the therapy. In some embodiments, a subject with a disease may provide a protein sample which may be analyzed using the methods of the present disclosure to determine an appropriate treatment.

In some embodiments, the methods of the present disclosure may be used to diagnose disease. Different diseases or disease stages may be associated with different panels of protein expression. Different panels of protein expression may be associated with different treatment outcomes for each given treatment. A subject's proteome expression data may be used to diagnose the subject and/or select the most appropriate therapy. In some cases, the methods of this disclosure may be able to diagnose a disease in a subject before the subject has any symptoms. In some cases, the methods of this disclosure may be able to differentiate between two or more diseases which present similarly or which have similar symptoms.

In some embodiments, the methods of the present disclosure may be used to characterize circulating tumor cells. Circulating tumor cells may be isolated from blood of subjects with cancer, or subjects suspected of having cancer, and protein may be extracted from the circulating cancer cells and assayed using the methods described herein. Protein expression data of circulating tumor cells may be used to determine the type of tumor or cancer that the cells are likely to have derived from, determine the status of the tumor or cancer, determine the stage of the tumor, select a therapeutic for treating the tumor or cancer, or evaluate a disease prognosis.

In some cases, the methods of this disclosure may be used to characterize immune cells. For example, the methods of this disclosure may be used to determine the activation state of immune cells. In some cases, a blood sample may be taken, and immune cells may be purified from the blood sample, and lysed to release proteins. In some cases, individual immune cells may be isolated, and may be separated before lysing, so as to determine the expression state of multiple individual cells. In some cases, the methods of the present disclosure may be used to determine the activation state of an immune cell.

In some embodiments, the methods of the present disclosure may be used to characterize proteins involved in disease processes, or developmental processes. For example, by obtaining a sample of proteins from a neovasculature, proteins which are involved in development of new blood vessels may be identified.

The methods of the present disclosure may be used to identify the individual or species a sample come from. For example the methods of the present disclosure could be used to determine if a sample is actually from the claimed species or source. The methods described herein may have an advantage over PCR based methods in samples with abundant protein but limited nucleic acid. For example, the methods can be used to identify the origins of some food samples, for example honey or fish. For further example, the methods of the present disclosure could be used to assess food safety and food quality control.

In some embodiments, the methods of the present disclosure may be used to assess protein-protein interactions. A cell, tissue, or cell free sample may be treated with a crosslinking reagent, or cross linking method such as ultraviolet light, to attach proteins to other molecules in their vicinity. The degree of crosslinking may be titrated to determine a crosslinking amount that does not cross link too many molecules together. The cross linked protein complexes may then be applied to a substrate such that each cross linked protein complex or protein molecule is physically separated from each and every other cross linked protein complex or protein molecule by an optically resolvable distance. The crosslinked protein complexes may be assayed as described above to determine affinity reagents which bind each protein complex. The binding data may be used to determine the combination of proteins present at each optically resolvable location.

The methods of the present disclosure may be used to assess protein-DNA interactions, or protein-RNA interactions. In some cases, the methods described herein may be used in place of a Chromatin Immunoprecipitation assay (ChIP), or a Chromatin Immunoprecipitation high throughput sequencing assay (ChIP-Seq). Samples may be prepared as for a traditional ChIP or ChIP-Seq assay. A cell, tissue, or cell free sample may be treated with a crosslinking reagent, or cross linking method such as ultraviolet light, to attach proteins to other molecules in their vicinity. In some cases, the samples may then be treated, for example by sonication, to cleave nucleic acids into fragments. Nucleic acid fragments may be less than about 100 bp, approximately 100 bp, 150 bp, 200 bp, 250 bp, 300 bp, 350 bp, 400 bp, 450 bp, 500 bp, 550 bp, 600 bp, 650 bp, 700 bp, 750 bp, 800 bp, 850 bp, 900 bp, 1 kb, 1.5 kb, or more than 1.5 kb. In some cases, the samples may not be treated to cleave nucleic acids into fragments, for example to assess interactions between proteins and mRNAs it may be preferred to maintain the mRNAs in as intact a form as possible. The crosslinked protein nucleic acid complexes may be attached to a substrate such that each complex is physically separated from each other complex by an optically resolvable distance. The identities of the proteins at each location may be determined using the methods described herein. The identities of the nucleic acids at each location may be determined by sequencing. In some cases, the nucleic acids may be eluted from the substrate prior to sequencing. For example, all nucleic acids bound to a given protein may be eluted from the substrate and sequenced to determine the identities of the nucleic acids bound to the given protein. Since some complexes may contain two or more proteins it may be necessary to generate a database of all possible protein sequences which includes to aggregate sequences of all possible combinations of 2, 3, 4, 5, or more than 5 proteins. In some cases, a database of all known DNA binding proteins may be used rather than a database of all known proteins.

The methods of the present disclosure may be used to assess protein localization within a cell. Subcellular organelles may be separated using any method known in the art, for example centrifugation, equilibrium density-gradient centrifugation, or affinity purification using organelle specific antibodies. Proteins isolated from each different organelle fraction, and from the cytoplasmic fraction, may be attached to different regions on a substrate, such that the proteins in each different fraction may be identified and quantified using the methods described herein. This information may be used to assess the localization of a novel or orphan protein, or to assess changes in localization of proteins during different treatments.

The methods of the present disclosure may be used to determine whether proteins are membrane bound, or membrane associated. A cellular, or tissue, sample may be homogenized and the membrane containing fraction may be separated from the non-membrane fraction. In some cases, the membrane associated fraction may be further separated to purify lipid rafts from other membrane. In some cases, the membrane associated fraction may comprise the cellular membrane, and membranes from organelles. In some cases, organelles may be isolated, and then membrane associated fractions isolated from each organelle. For example a sample may be treated to isolate nuclei, and then the nuclear membranes may be isolated to determine proteins associated with the nuclear membrane.

The methods of the present disclosure may be used to determine proteins which are secreted from cells into the extracellular space. In some examples, a sample of extracellular fluid, such as plasma, serum, lymph, interstitial fluid, synovial fluid, intravitreal fluid, aqueous humor, stomach acid, bile, saliva, pus, seminal fluid, vaginal discharge, tears, cerebrospinal fluid, urine, mucus, breast milk, sebum, sweat, phlegm, earwax, colostrum, chyme, chyle, smegma, pericardial effusion, transudate, rheum or feces. In some cases, the extracellular fluid may be filtered or centrifuged to remove cells or cellular debris in the sample. In some cases, the extracellular fluid may be filtered to remove cells, treated with a denaturing agent and then filtered to remove insoluble debris. In some cases, vesicles, for example exosomes, may be isolated from an extracellular fluid and analyzed using the methods disclosed herein.

In some embodiments, a tissue sample may be partially digested with proteases to weaken connections between cells, and between cells and extracellular matrix. The cells may be removed by filtration, centrifugation, or gradient centrifugation, and the cells and extracellular proteins may be analyzed separately. In some cases, cells may be cultured in media, and the media may be extracted and analyzed to investigate extracellular proteins.

In some embodiments, the methods of the present disclosure may be used to determine purity of a purified protein. For example, the methods of the present disclosure may be used to determine the purity of a purified recombinant protein. In some cases, the methods of the present disclosure may be used to determine the purity of a therapeutic protein.

In some embodiments, the methods of the present disclosure may be used to conduct a reverse drug screen. Using the methods of this disclosure, a candidate drug compound may be immobilized upon a support and exposed to a protein isolate. Proteins which bind to the immobilized drug candidate may then be analyzed using the methods of this disclosure to determine the identities of all bound proteins. In some cases, the drug candidate may be labeled with a moiety which may be used to pull down the drug candidate and bound proteins, and may be applied to cells or tissue samples. In some cases, the drug candidate may be applied to cells, tissue, or model organisms, and then the cells, tissues, model organisms, or biopsies from the model organisms maybe fractionated and different fractions analyzed for the presence of the drug candidate. A fraction containing the drug candidate may be analyzed to determine the proteins that separated with the drug candidate, and may be further fractionated if required.

In some embodiments, the methods disclosed herein may be used to identify drug targets. For example, a biopsy from a subject with a disease may be compared with an equivalent biopsy from a subject without the disease, and proteins with altered expression may be identified as putative targets. In some cases, many biopsies from many subjects with a disease may be compared to many equivalent biopsies from many subjects without the disease.

In some cases, the methods of the present disclosure may be used to identify proteins which can interact with one or more pathogens. For example, a sample of infected tissue, or infected cells, may be treated with a cross linking agent, and then analyzed using a database containing the host and pathogen protein sequences, and combinations of both sequences, to determine interactions between host and pathogen proteins. In some cases, a the pathogen protein which interacts with the host cells may be known, in such cases, the known protein may be used to pull down host proteins which may then be identified using the methods disclosed herein.

In some cases, the methods of the present disclosure may be used to determine antibody targets. For example, a sample of antibodies may be isolated from a subject, and then used to pull down target proteins from a tissue or cellular homogenate, or from a diagnostic protein library. The proteins bound by the antibodies may be used to identify the targets of the proteins. For example, a patient who presents with symptoms of infection may provide a blood sample. The blood sample may be purified to extract antibodies. The antibodies may then be exposed to a diagnostic protein library which contains proteins from different pathogens, as well as proteins involved in autoimmune diseases. The bound proteins are then analyzed to determine the characteristics of the isolated antibodies. For example, if the isolated antibodies comprise a large number of proteins which bind to *E. coli* proteins then they may indicate an *E. coli* infection.

The methods of the present disclosure may also be used to screen antibodies to identify antibodies which bind a desired target. For example, proteins may be expressed from a library of antibody coding sequences, and different pools of antibodies may be exposed to samples containing the target protein. Using the methods of this disclosure, the proteins bound by the pools of antibodies can be identified, and pools which contain antibodies binding the desired protein may be identified. The antibodies in the identified pools may be retested individually, or in smaller pools, to identify the antibodies which bind the desired protein. The samples containing the target protein may be purified samples of the target protein, or may be cellular lysates, or tissue homogenates. In cases, where the samples containing the target protein do not comprise purified protein then the binding data will also show the specificity of the antibodies for the target protein compared to other proteins in the sample, and will show the likely off target binding of the antibodies.

In some embodiments, the methods disclosed herein may be used to characterize neoantigens. Neoantigens may be antigens encoded by mutated genes. In some cases, neoantigens may be encoded by tumor specific genes. Neoantigens may play a key role in cancer immunotherapy. Methods of this disclosure may be used to identify neoantigens in a cancer or tumor biopsy In some cases, the methods of the present disclosure may be used to assess a microbiome. In some cases, the microbiome may be an intestinal microbiome, a skin microbiome, a vaginal microbiome, or an oral microbiome. In some cases, the microbiome may be a soil microbiome, or a plant microbiome. In some cases, the methods of the present disclosure may be able to identify bacterial species of the microbiome. In some cases, the methods of the present disclosure may be able to identify bacterial genuses, families or clades of the microbiome.

In some cases, the methods of the present disclosure may be used to identify pathogens and/or symbionts in plants. For example, the methods of the present disclosure could be used to determine the presence of bacterial or fungal pathogens in samples of plants, or plant products. In some cases, the bacterial or fungal pathogens may be plant pathogens which affect the health of the plant. In some cases, the bacterial or fungal pathogens may be human or animal pathogens which cause disease in people or animals eating the plants.

In some cases, the methods of the present disclosure may be used in agriculture. For example, the methods of the present disclosure may be used to determine proteins associated with different phenotypes. In some cases, samples may be taken from several strains of a crop plant which have different phenotypes of interest and protein expression may be compared to determine proteins which may be involved in the different phenotypes. For example several strains of wheat with increased drought tolerance may be compared to strains of wheat with poor drought tolerance to identify protein expression patterns which may contribute to the increased drought tolerance. Phenotypes which may be of interest include, drought tolerance, resistance to infection, temperature tolerance, storage tolerance, flavor, nutrition, ability to grow in soil with poor levels of nitrogen, phosphorus, or other minerals. Temperature tolerance may be either tolerance to high temperatures, tolerance to low temperatures or both. Resistance to infection may refer to general resistance to infections, or to resistance to infection by a specific disease or parasite.

In some cases, the methods of the present disclosure may be detect proteins which are not derived from the expected proteome. In such cases, the binding information of the proteins may be compared against a database comprising sequences from many other proteomes. For example, if a human tissue sample is analyzed proteins may be identified which do not match the human proteome. These proteins may be then be compared to a database comprising sequences of known human pathogens, or to a database of all known sequences. In some cases, the methods of the present disclosure may identify novel or unknown proteins. In some cases, it may not be possible to identify a protein with certainty, but it may be possible to identify one or more closest protein matches.

In some cases, the methods of the present disclosure may be used to develop a set of affinity reagents which may be used to screen for a particular protein. The particular protein may be a protein for which no specific antibody, aptamer, or binding protein may be available, or may be a protein for which there is a specific antibody, aptamer, or binding protein available.

The methods of the present disclosure may be used to identify any single protein molecule from a pool of protein molecules using less affinity reagents than the number of possible proteins. For example the methods may identify, with certainty above a threshold amount, an unidentified single protein molecule from a pool of n possible proteins, using a panel of affinity reagents, wherein the number of affinity reagents in the panel is m, and wherein m is less than n. The unidentified protein may be a known protein which corresponds to known protein and gene sequences, or may be an unknown protein without known protein or gene sequences. In the case of an unknown protein this method may identify a signature of the unknown protein, and thus the presence and quantity of the unknown protein, but not the amino acid sequence. The methods of the present disclosure may be used to select a panel of m affinity reagents capable of identifying an unidentified protein selected from a pool of n possible proteins. The methods disclosed herein are also capable of uniquely identifying and quantifying n proteins in a mixture of proteins using m binding reagents, and wherein each protein is identified via a unique profile of binding by a subset of the m the binding reagents. Further, m may be less than about a half, a third, a fourth, a fifth, a sixth, a seventh, a tenth, a twentieth, a fiftieth or a hundredth of n. For further example the present disclosure may be used to select a panel of less than about 100, 200, 300, 400, 500, 600, 700, 800, 900, 1000, 1500, 2000, 2500, 3000, 3500, or 4000 affinity reagents, such that the panel of affinity reagents is capable of uniquely identifying each of at least about 100, 500, 1000, 2000, 3000, 4000, 5000, 6000, 7000, 8000, 9000, 10,000, 12,000, 14,000, 16,000, 18,000, 20,000, 25,000, 30,000, 35,000, 40,000, 50,000, 100,000, 200,000, 300,000, 400,000, 500,000, 600,000, 700,000, 800,000, 900,000, 1,000,000, 2,000,000, 3,000,000, 4,000,000, or 5,000,000 different proteins.

The methods of the present disclosure may be capable of identifying most of the proteins in a proteome. The methods of the present disclosure may be capable of identifying most of the proteins in a mammalian, bird, fish, amphibian, reptilian, vertebrate, invertebrate, plant, fungal, bacterial or archaeal proteome. The methods of the present disclosure may be capable of identifying more than about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% of the proteins in a proteome.

In some cases, the methods of the present disclosure may be inverted. Each single, individual, protein molecule may be conjugated to a uniquely labeled nanobead. The nanobeads may be labeled by any detectable method, for example fluorescence. In some cases, each nanobead may comprise a unique combination of several possible fluorophores. In some cases, the nanobead may be a DNA cluster or another chemical polymer. The protein-nanobeads may then be applied to a substrate with immobilized affinity reagents. Each optically resolvable address on the substrate comprises either an individual affinity reagent of known properties, or a plurality of copies of a single affinity reagent species. In some cases, the substrate is imaged continuously, or every 5 minutes, 4 minutes, 3 minutes, 2 minutes, 1 minute, 0.5 minutes, 0.1 minutes, 0.05 minutes or less than 0.05 minutes. The location of each conjugated protein-nanobead is determined in each image, and then the amount of time which each protein spent at each address on the substrate is calculated. Protein binding to the affinity reagents may be detected by an increase in time spent at that address. This information may be used to determine the likely epitopes comprised by the protein, thus allowing the protein to be identified as described herein.

EXAMPLES

Example 1: Protein Identification Using Antibodies that Bind Unique 3-Mer Peptides A computational experiment was performed to determine the relationship between the percentage coverage of the set of all epitopes in a proteome and the percentage of the proteome that may be identified using the methods of this disclosure. For this experiment the set of all 3-mer amino acid epitopes was selected. Protein modifications were not considered. As there are 20 naturally occurring amino acids the total set of all 3-mer epitopes is 20×20×20=8000 possible epitopes. For the simulation x was set as the number of epitopes screened in an experiment, for each value of x from 1 to 8000 a set of x epitopes were randomly selected and the percentage of the proteome which could be identified was calculated. FIG. 13 shows the results of this simulation.

Figure 15:
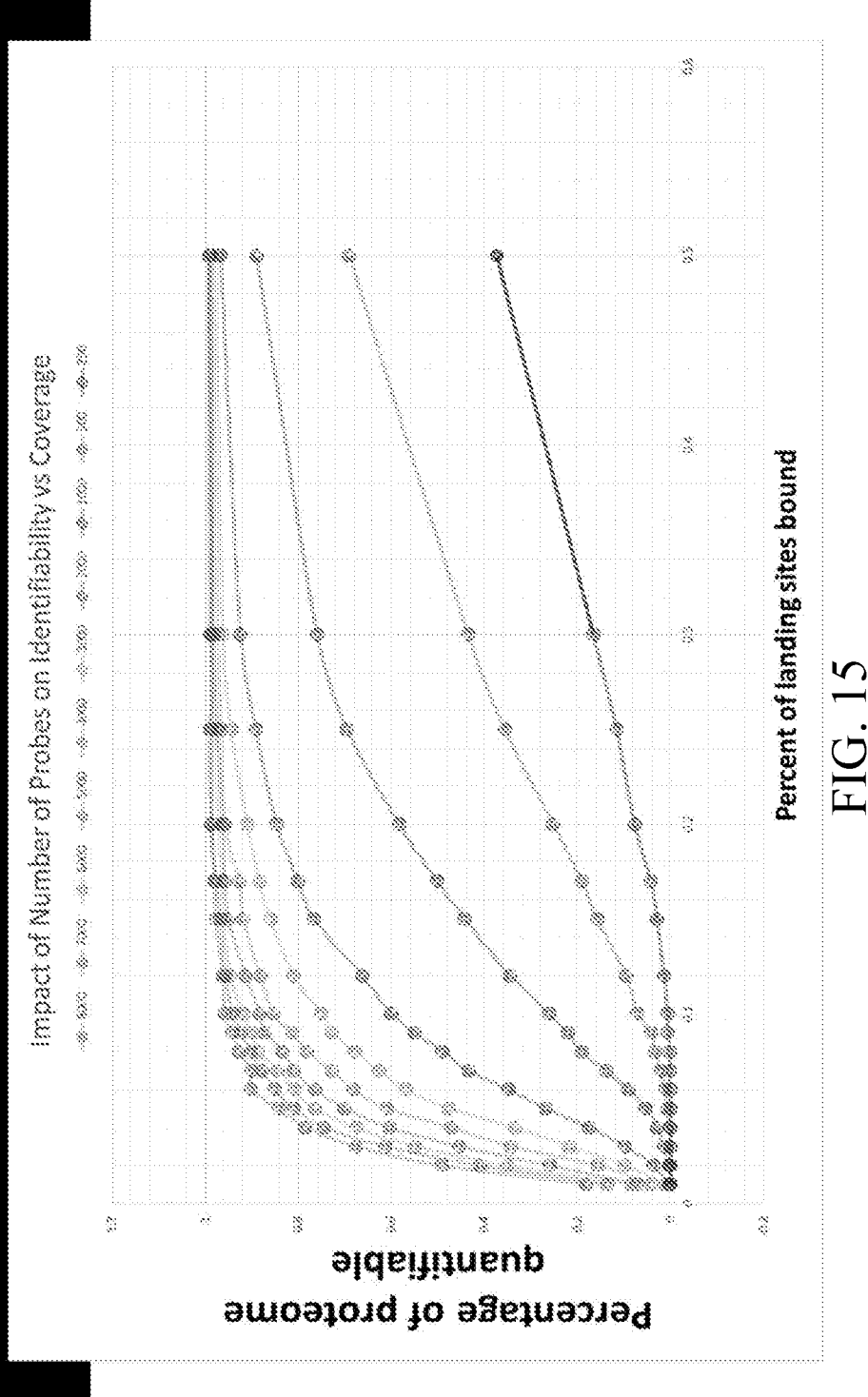
FIG. 15 illustrates an example of impact of number of 3-mer multiaffinity probes on identifiability vs coverage of proteome, in accordance with embodiments herein.

Example 2: Protein Identification Using Antibodies that Bind Unique 3-Mer Peptides A further computational experiment was performed to determine the impact of the number of affinity reagents on identifiability and coverage. Data series were calculated for a range of affinity reagent pool sizes to show the percentage of the proteome which may be identified (y axis) for each possible coverage of a protein and the results are shown in Table 1. For example, a protein with 100 amino acids has 98 3-mer amino acid epitopes "landing sites", if 20% of these 3-mer amino acid epitopes are bound that may or may not be sufficient to identify the protein. As shown in FIG. 15, with an affinity reagent pool of 250 3-mer specific affinity reagents if 20% of the landing sites of each protein are bound, then only about 7% of the proteome may be identified. For an affinity reagent pool of 8000 affinity reagents then with 20% of landing sites bound about 98% of the proteome may be identified.

Figure 17:
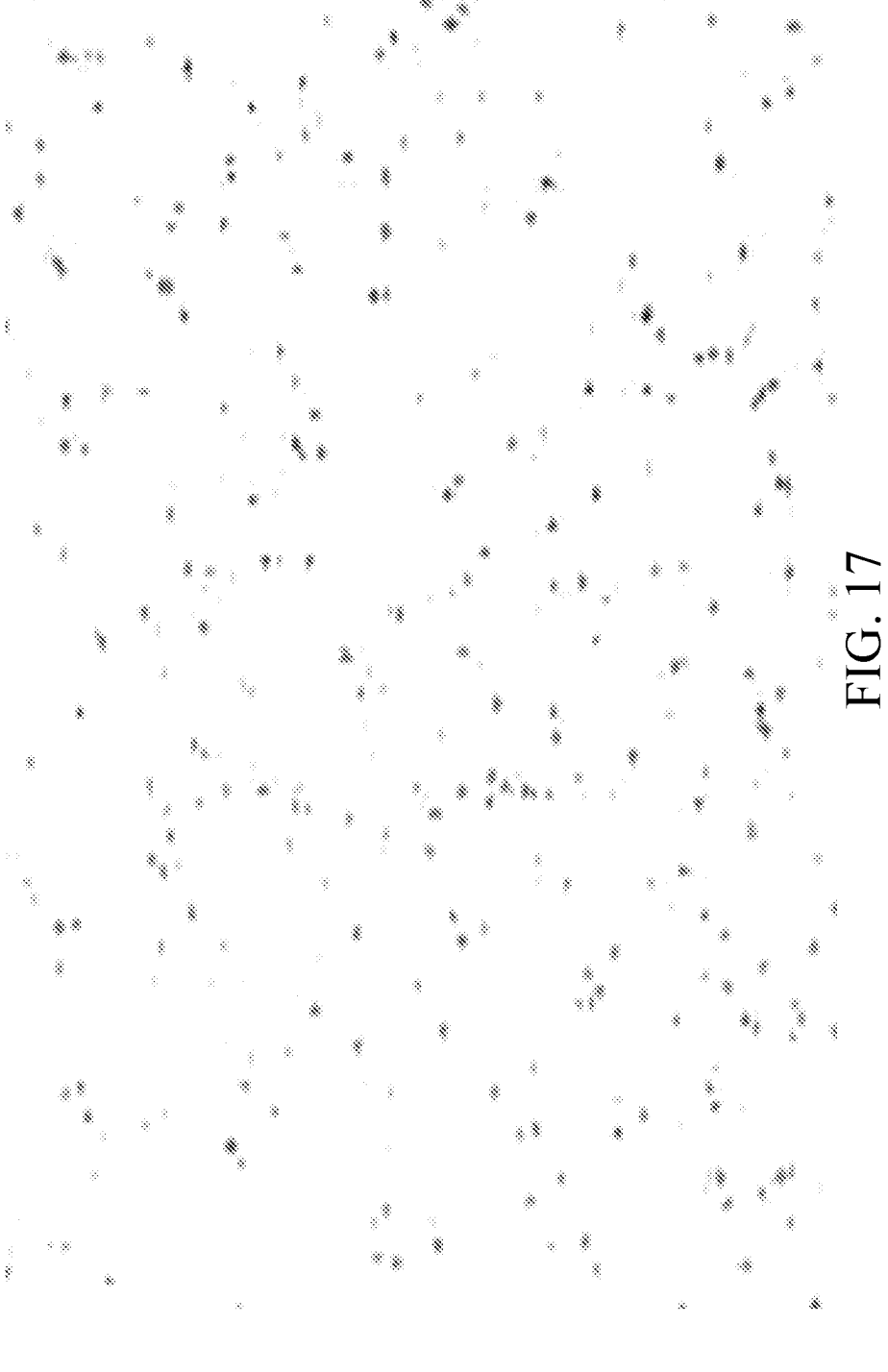
FIG. 17 illustrates identification of a protein, in accordance with embodiments herein.

Initial imaging showed no baseline residual fluorescence, indicating complete denaturation of the Green Fluorescent Protein. The protein was then incubated with an anti-peptide antibody with an attached Alexa-Fluor 647. The anti-peptide antibody was then rinsed with 0.1% Tween-20. This was then imaged using TIRF on a Nikon Eclipse Ti with an Andor NEO sCMOS camera. FIG. 17 shows a resulting image captured (colors reversed for clarity).

Example 4: Identification of a Protein

A proteome of four possible proteins, Green Fluorescent Protein, RNASE1, LTF, and GSTM1, is depicted in FIG. 18. In this example, a single molecule of an unknown protein from this proteome is conjugated to a position on a substrate. The unknown protein is sequentially interrogated by a panel of nine different affinity reagents. Each of the nine different affinity reagents recognize a different amino acid trimer [AAA, AAC, AAD, AEV, GDG, QSA, LAD, TRK, DGD], and each is labeled with a fluorescent dye. It is determined that the unknown protein is bound by the affinity reagents DGD, AEV, LAD, GDG, and QSA. Analysis of the sequences of the four proteins of this proteome indicates that only GFP contains all five of these three amino acid motifs, these motifs are underlined in the sequence of FIG. 18. Thus, it is determined that the single molecule of the unknown protein is a GFP protein.

TABLE 1

| | Impact of number of 3-mer multiaffinity probes on identifiability vs coverage of proteome | | | | | | | | | |
|---|---|---|---|---|---|---|---|---|---|---|
| | 8000 | 7000 | 6000 | 5000 | 4000 | 3000 | 2000 | 1000 | 500 | 250 |
| 1.00% | 0.1825 | 0.135 | 0.0845 | 0.072 | 0.042 | 0.0125 | 0.0035 | 0 | 0 | 0 |
| 2.00% | 0.492 | 0.41 | 0.3515 | 0.26 | 0.156 | 0.0985 | 0.037 | 0.0035 | 0.0005 | 0 |
| 3.00% | 0.677 | 0.614 | 0.55 | 0.455 | 0.344 | 0.2175 | 0.0985 | 0.015 | 0.0005 | 0 |
| 4.00% | 0.786 | 0.745 | 0.676 | 0.604 | 0.472 | 0.334 | 0.176 | 0.029 | 0.003 | 0 |
| 5.00% | 0.843 | 0.811 | 0.765 | 0.7005 | 0.61 | 0.4765 | 0.269 | 0.054 | 0.0075 | 0 |
| 6.00% | 0.9025 | 0.852 | 0.809 | 0.7645 | 0.6815 | 0.569 | 0.3485 | 0.092 | 0.012 | 0.0015 |
| 7.00% | 0.9005 | 0.877 | 0.8435 | 0.81 | 0.7285 | 0.626 | 0.4345 | 0.1395 | 0.022 | 0.0025 |
| 8.00% | 0.9275 | 0.9025 | 0.8875 | 0.835 | 0.782 | 0.678 | 0.491 | 0.192 | 0.034 | 0.002 |
| 9.00% | 0.9415 | 0.923 | 0.898 | 0.8725 | 0.814 | 0.728 | 0.5495 | 0.221 | 0.0415 | 0.0065 |
| 10.00% | 0.9575 | 0.941 | 0.919 | 0.8835 | 0.8535 | 0.751 | 0.601 | 0.261 | 0.0715 | 0.007 |
| 12.00% | 0.9635 | 0.957 | 0.946 | 0.913 | 0.8825 | 0.81 | 0.663 | 0.3445 | 0.0955 | 0.0145 |
| 15.00% | 0.978 | 0.969 | 0.962 | 0.9505 | 0.9185 | 0.8605 | 0.7675 | 0.443 | 0.1585 | 0.0295 |
| 17.00% | 0.981 | 0.9765 | 0.9645 | 0.9575 | 0.927 | 0.884 | 0.805 | 0.503 | 0.1915 | 0.0435 |
| 20.00% | 0.9885 | 0.986 | 0.9725 | 0.9635 | 0.9575 | 0.9105 | 0.847 | 0.584 | 0.2525 | 0.0775 |
| 25.00% | 0.99 | 0.9865 | 0.9785 | 0.9745 | 0.966 | 0.9445 | 0.8915 | 0.6955 | 0.357 | 0.1165 |
| 30.00% | 0.9865 | 0.9895 | 0.985 | 0.9825 | 0.973 | 0.9625 | 0.9245 | 0.76 | 0.4355 | 0.1665 |
| 50.00% | 0.9915 | 0.9915 | 0.9935 | 0.9895 | 0.9855 | 0.978 | 0.967 | 0.89 | 0.691 | 0.374 |

Example 3: Illuminated Protein Molecules Conjugated on a Substrate

Figure 16A:
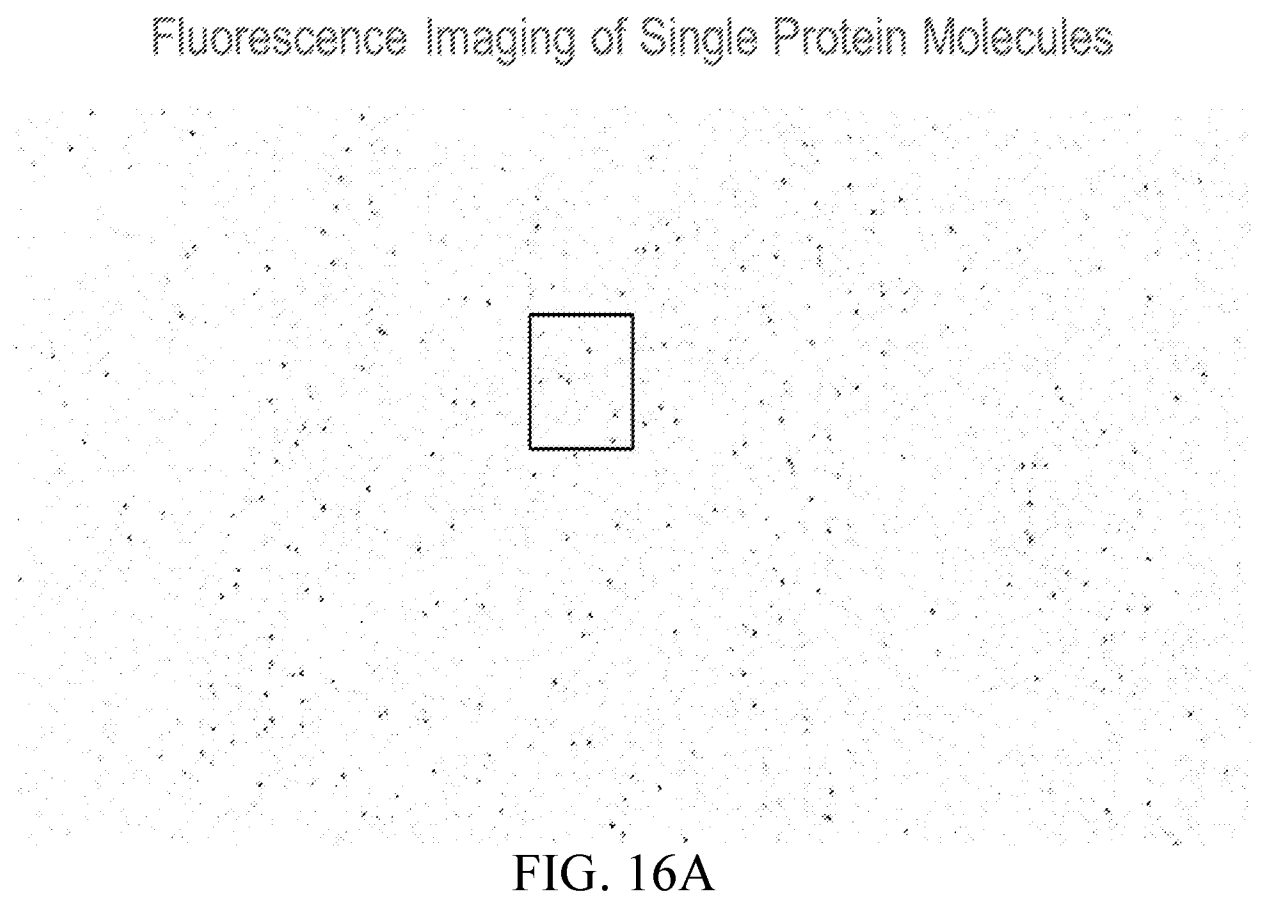
Figure 16B:
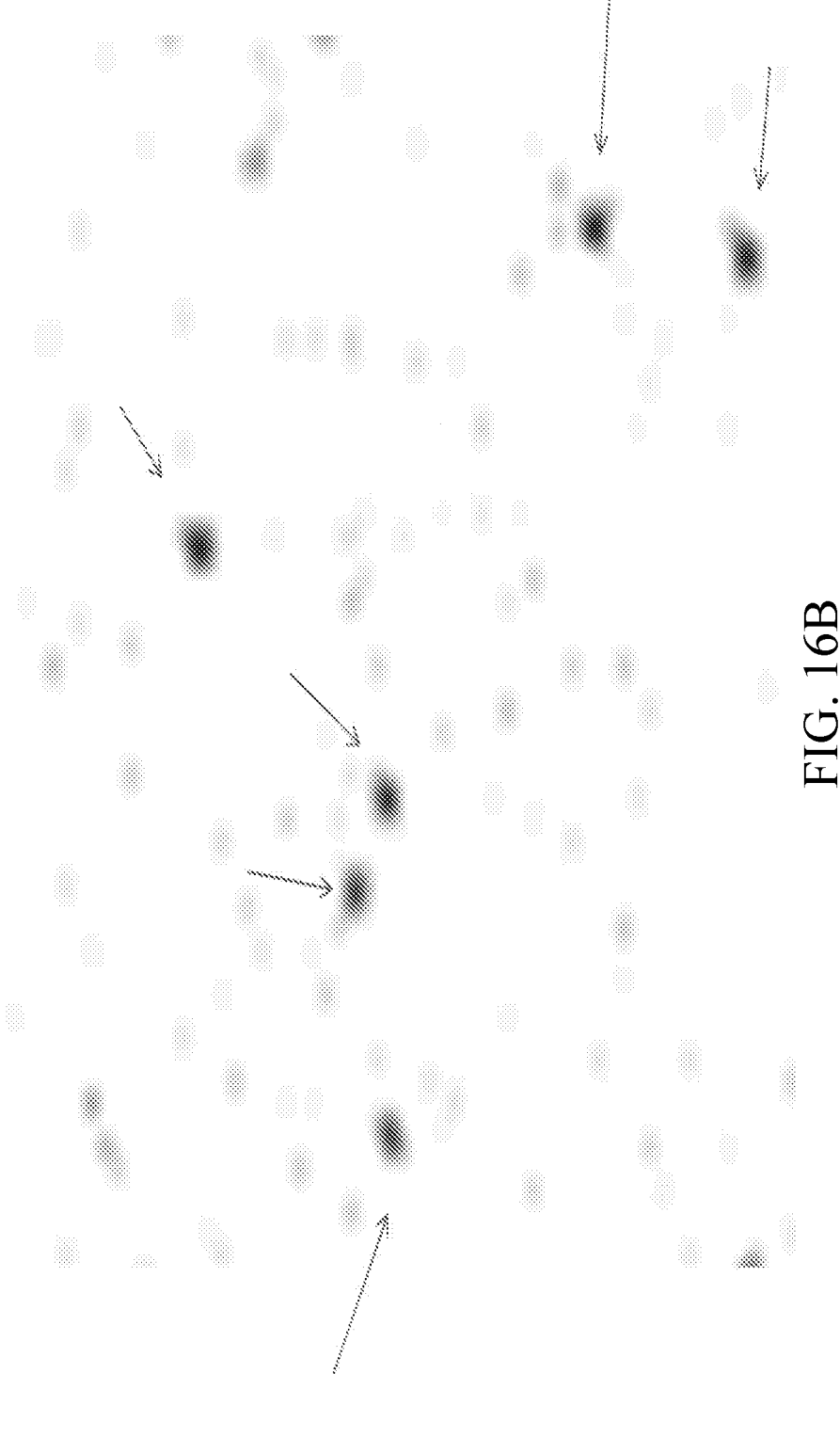
FIG. 16B illustrates an image showing a blown up portion of the indicated area of FIG. 16A with conjugated proteins indicated by arrows, in accordance with embodiments herein.

A fluorescent protein sample, Phycoerythrin, was directly conjugated to an NHS-Ester coated coverslip for 4 hours in an incubation chamber at 4 degrees. The fluorescent protein sample was then imaged on a Leica DMi8 with a Hamamatsu orca flash 4.0 camera using 300 ms exposure. FIGS. 16A and 16B show a resulting image captured (colors reversed for clarity). As seen in FIGS. 16A and 16B, each dark spot represents an area of fluorescence signal indicating the presence of a protein. FIG. 16B is a blow-up of FIG. 16A. Arrows in FIG. 16B indicate signals representing proteins that are clearly distinguishable from background noise.

A second protein sample, Green Fluorescent Protein, was denatured and directly conjugated to an NHS-Ester coated coverslip for 4 hours in an incubation chamber at 4 degrees.

Example 5: Subcellular Localization of Proteins

The methods of the present disclosure may be used to determine functional information about proteins. Cultured human cells known to express a protein or proteins of interest, or cultured human cells engineered to overexpress the protein or protein of interest, may be fractionated to separate subcellular organelles and cytoplasm. Alternatively a cell type of interest may be fractionated to investigate subcellular localizations of all proteins in the cell.

The initial step in purifying subcellular structures is to rupture the plasma membrane and the cell wall, if present. First, the cells will be suspended in a solution of isotonic sucrose (0.25 M) or a combination of salts similar in composition to those in the cell's interior. The cells may then be broken by stirring the cell suspension in a high-speed blender or by exposing it to highfrequency sound (sonication). Plasma membranes may also be sheared by special pressurized tissue homogenizers in which the cells are forced through a very narrow space between the plunger and the vessel wall. The cell solution is kept at 0° C. to best preserve enzymes and other constituents after their release from the stabilizing forces of the cell.

Because the plasma membrane is highly permeable to water but poorly permeable to the salts and other small molecules (solutes) within cells, osmotic flow can be enlisted to help rupture cells. Cells are placed in a hypotonic solution and water flows into the cells causing the cells to swell and then more easily rupture. Disrupting the cell produces a mix of suspended cellular components, the homogenate, from which the desired organelles can be retrieved.

The fractionation procedures may begin with differential centrifugation at increasingly higher speeds, also called differential-velocity centrifugation. The different sedimentation rates of various cellular components can make it possible to separate them partially by centrifugation. Nuclei and viral particles can sometimes be purified completely by such a procedure. After centrifugation at each speed for an appropriate time, the supernatant is poured off and centrifuged at higher speed. Each pelleted fraction can be resuspended and further separated by equilibrium density gradient centrifugation. The supernatant may be saved from the final centrifugation and assessed as the cytoplasmic fraction.

Equilibrium density-gradient centrifugation separates cellular components according to their density. The impure organelle fraction is layered on top of a solution that contains a gradient of a dense nonionic substance, such as sucrose or glycerol. The tube is centrifuged at a high speed (about 40,000 rpm) for several hours, allowing each particle to migrate to an equilibrium position where the density of the surrounding liquid is equal to the density of the particle. In typical preparations from animal cells, the rough endoplasmic reticulum (density=1.20 g/cm$^3$) separates well from the Golgi vesicles (density=1.14 g/cm$^3$) and from the plasma membrane (density=1.12 g/cm$^3$). (The higher density of the rough endoplasmic reticulum is due largely to the ribosomes bound to it.) This method also works well for resolving lysosomes, mitochondria, and peroxisomes in the initial mixed fraction obtained by differential centrifugation.

Since each organelle has unique morphological features, the purity of organelle preparations can be assessed by examination in an electron microscope. The purity of each organelle preparation is quantified and this information may be used to interpret the results.

Figure 2:
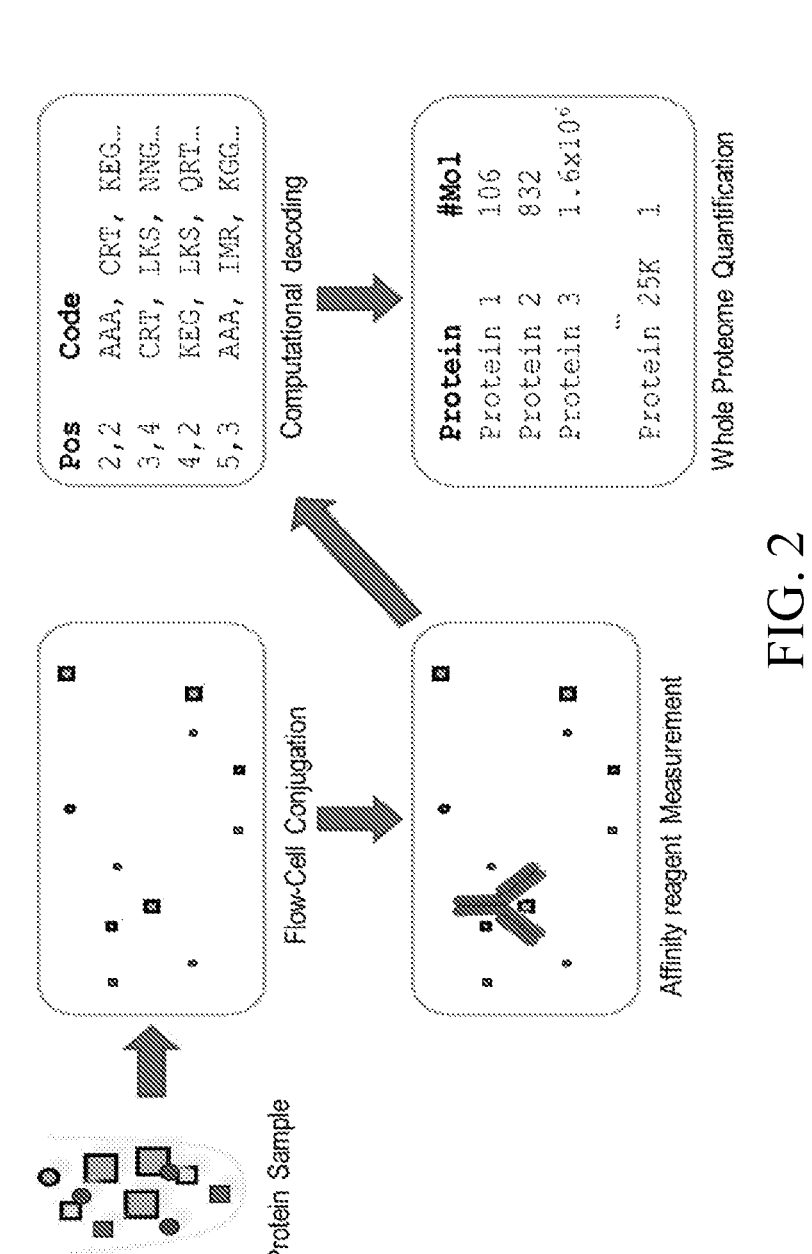
FIG. 2 illustrates a second schematic of protein quantification by anti-peptide antibody decoding, in accordance with some embodiments.

Once the organelles are separated proteins are extracted from each organelle preparation, and from the cytoplasmic sample. Additionally a whole cell preparation may be included in the protein identification assay. Where appropriate each organelle preparation may be further fractionated into a membrane fraction and a non-membrane fraction. The isolated proteins are applied to a substrate such that each fraction (organelle and/or membrane/non-membrane) is applied to a different region of the substrate, and each individual protein molecule is physically separated from all other protein molecules (including all other identical protein molecules) by an optically resolvable distance. A series of fluorescently labeled affinity reagents are applied to the substrate and images are taken after each application. The images are used to compile a list of affinity reagents which bind to each protein (based on the optically resolvable 'address' of the protein), and this data is used to identify each protein from a sequence listing of the human proteome. Once each individual protein molecule on the substrate is identified the number of instances of each protein may be quantified for each fraction (see FIG. 1 and FIG. 2). This information may be presented as a percentage location of each protein. For example it may be found that 50% of a first protein of interest is located in the nuclear fraction, 30% of the first protein of interest is located in the cytoplasm, and the remaining 20% of the first protein of interest was located in the rough endoplasmic reticulum.

Computer Control Systems

Figure 14:
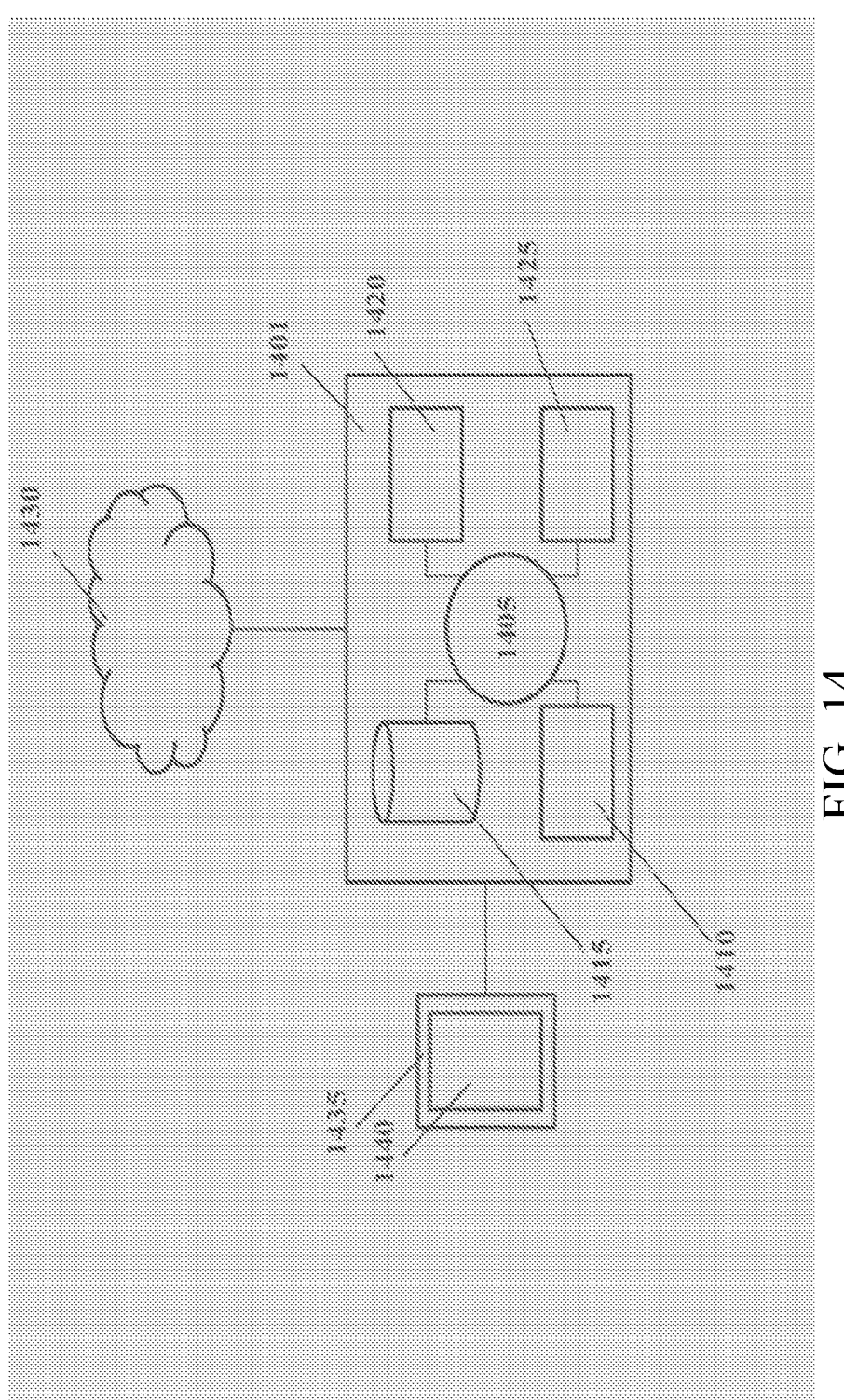
FIG. 14 illustrates a computer control system that is programmed or otherwise configured to implement methods provided herein.

The present disclosure provides computer control systems that are programmed to implement methods of the disclosure. FIG. 14 shows a computer system 1401 that is programmed or otherwise configured to characterize and identify biopolymers, such as proteins. The computer system 1401 can regulate various aspects of assessing and analyzing samples of the present disclosure, such as, for example, observing signals at unique spatial addresses of a substrate; determining a presence of an identifiable tag linked to a biopolymer portion at unique spatial addresses based on observed signals; assessing the determined identifiable tags against a database of biopolymer sequences to determine characteristics of biopolymer portions. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, determine characteristics and/or identities of biopolymer portions, such as protein portions. For example, algorithms may be used to determine a most likely identity of a candidate biopolymer portion, such as a candidate protein portion.

In some embodiments aptamers or peptamers which recognize short epitopes present in many different proteins may be referred to as digital aptamers or digital peptamers. An aspect of the invention provides a set of digital aptamers or digital peptamers, wherein the set comprises at least about 15 digital aptamers or digital peptamers, wherein each of the 15 digital aptamers or digital peptamers has been characterized to bind specifically to a different epitope consisting of 3 or 4 or 5 consecutive amino acids, and wherein each digital aptamer or digital peptamer recognizes a plurality of distinct and different proteins that comprise the same epitope to which the digital aptamer or digital peptamer binds. In some embodiments the set of digital aptamers or digital peptamers comprises 100 digital aptamers or digital peptamers that bind epitopes consisting of 3 consecutive amino acids. In some embodiments the set of digital aptamers or digital peptamers further comprises 100 digital aptamers that bind epitopes consisting of 4 consecutive amino acids. In some embodiments the set of digital aptamers or digital peptamers further comprises 100 digital aptamers or digital peptamers that bind epitopes consisting of 5 consecutive amino acids. In some cases, digital affinity reagents may be an antibody, aptamer, peptamer, peptide or Fab fragment.

In some embodiments the set of digital aptamers comprises at least about 20, 30, 40, 50, 60, 70, 80, 90, 100, 200, 300, 400, 500, 600, 700 800, 900, or 1000 digital aptamers. In some embodiments the set of digital aptamers comprises at least 1000 digital aptamers that bind epitopes consisting of 4 consecutive amino acids. In some embodiments the set of digital aptamers further comprises at least 100 digital aptamers that bind epitopes consisting of 5 consecutive amino acids. The set of digital aptamers further comprises at least 100 digital aptamers that bind epitopes consisting of 3 consecutive amino acids. In some embodiments the set of digital aptamers are immobilized on a surface. In some embodiments the surface is an array.

In another aspect the invention provides a method for generating a protein binding profile of a sample comprising a plurality of different proteins, said method comprising: contacting said sample with a set of digital aptamers, under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; and detecting binding of protein to said digital aptamers, whereby a protein binding profile of the sample is generated.

In some embodiments the method further comprises the step of treating the sample with a protein cleaving agent prior to step (a) of contacting the sample with the set of digital aptamers under conditions that permit binding.

In another aspect the invention comprises a library of protein binding profiles for two or more different samples each of which comprises a plurality of proteins, said method comprising: contacting a sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; generating a protein binding profile of the sample being tested by detecting binding of protein to the digital aptamers, whereby a protein binding profile is generated; and repeating the steps above with at least two samples.

In some embodiments the method further comprises the step of treating the sample with a protein cleaving agent prior to the step of contacting the sample with the set of digital aptamers under conditions that permit binding.

In another aspect the invention comprises a method for characterizing a test sample, comprising: contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein generating a protein binding profile of said test sample by detecting binding of protein to the digital aptamers; and comparing the generated protein binding profile of the test sample with a protein binding profile of a reference sample to characterize the test sample.

In another aspect the invention comprises a method for determining presence or absence of a bacteria, virus, or cell in a test sample, said method comprising: contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; optionally removing an unbound protein; generating a protein binding profile of the test sample by detecting binding of protein to the digital aptamers, whereby a protein binding profile is generated; and comparing the protein binding profile of the test sample with a protein binding profile of a reference sample, whereby presence or absence of the bacteria, virus or cell in the test sample is determined by the comparison.

In another aspect the invention comprises a method for identifying a test protein in a sample, said method comprising: contacting a sample comprising or suspected of comprising the test protein with a set of digital aptamers that comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; and determining the identity of the test protein by detecting of binding of the test protein to the set of digital aptamers, wherein at least about six digital aptamers bind the test protein; and wherein presence of binding indicates presence of at least about six epitopes in the test protein, wherein the identity of the at least about six epitopes is used to identify the test protein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Notwithstanding the appended claims, the disclosure set forth herein is also defined by the following clauses:

1. A set of digital aptamers, wherein the set comprises at least about 15 digital aptamers, wherein each of the 15 digital aptamers has been characterized to bind specifically to a different epitope consisting of 3 or 4 or 5 consecutive amino acids, and wherein each digital aptamer recognizes a plurality of distinct and different proteins that comprise the same epitope to which the digital aptamer binds.

2. The set of digital aptamers according to clause 1, wherein the set comprises 100 digital aptamers that bind epitopes consisting of 3 consecutive amino acids.

3. The set of digital aptamers according to clause 1, wherein the set further comprises 100 digital aptamers that bind epitopes consisting of 4 consecutive amino acids.

4. The set of digital aptamers according to clause 3, wherein the set further comprises 100 digital aptamers that bind epitopes consisting of 5 consecutive amino acids.

5. The set of digital aptamers according to clause 1, wherein the set comprises at least about 20, 30, 40, 50, 60, 70, 80, 90, 100, 200, 300, 400, 500, 600, 700 800, 900, or 1000 digital aptamers.

6. The set of digital aptamers according to clause 1, wherein the set comprises at least 1000 digital aptamers that bind epitopes consisting of 4 consecutive amino acids.

7. The set of digital aptamers according to clause 6, wherein the set further comprises at least 100 digital aptamers that bind epitopes consisting of 5 consecutive amino acids.

8. The set of digital aptamers according to clause 7, wherein the set further comprises at least 100 digital aptamers that bind epitopes consisting of 3 consecutive amino acids.

9. The set of digital aptamers according to any of clauses 1-8, wherein the digital aptamers are immobilized on a surface.

10. The set of digital aptamers according to clause 9, wherein the surface is an array.

11. A method for generating a protein binding profile of a sample comprising a plurality of different proteins, said method comprising:

a) contacting said sample with a set of digital aptamers, under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;

b) optionally removing an unbound protein; and c) detecting binding of protein to said digital aptamers, whereby a protein binding profile of the sample is generated.

12. The method of clause 11, wherein the method further comprises the step of treating the sample with a protein cleaving agent prior to step (a) of contacting the sample with the set of digital aptamers under conditions that permit binding.

13. A method for generating a library of protein binding profiles for two or more different samples each of which comprises a plurality of proteins, said method comprising:

a) contacting a sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;

b) optionally removing an unbound protein;

c) generating a protein binding profile of the sample being tested by detecting binding of protein to the digital aptamers, whereby a protein binding profile is generated; and d) repeating steps (a) through (c) with at least two samples.

14. The method of clause 13, wherein the method further comprises the step of treating the sample with a protein cleaving agent prior to step (a) of contacting the sample with the set of digital aptamers under conditions that permit binding.

15. A library of protein binding profiles, wherein the library is prepared using the method of clause 13.

16. A method for characterizing a test sample, comprising:

a) contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;

b) optionally removing an unbound protein;

c) generating a protein binding profile of said test sample by detecting binding of protein to the digital aptamers; and d) comparing the generated protein binding profile of the test sample with a protein binding profile of a reference sample to characterize the test sample.

17. A method for determining presence or absence of a bacteria, virus, or cell in a test sample, said method comprising a) contacting the test sample with a set of digital aptamers under conditions that permit binding, wherein the set of digital aptamers comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds;

b) optionally removing an unbound protein;

c) generating a protein binding profile of the test sample by detecting binding of protein to the digital aptamers, whereby a protein binding profile is generated; and d) comparing the protein binding profile of the test sample with a protein binding profile of a reference sample, whereby presence or absence of the bacteria, virus or cell in the test sample is determined by the comparison.

18. A method for identifying a test protein in a sample, said method comprising a) contacting a sample comprising or suspected of comprising the test protein with a set of digital aptamers that comprises at least about 15 digital aptamers, wherein each of the 15 digital aptamers has been characterized to bind specifically to a different epitope consisting of 3 or 4 or 5 consecutive amino acids, and each digital aptamer recognizes a plurality of distinct and different proteins that comprise the same epitope to which the digital aptamer binds; and b) determining the identity of the test protein by detecting of binding of the test protein to the set of digital aptamers, wherein at least about six digital aptamers bind the test protein; and wherein presence of binding indicates presence of at least about six epitopes in the test protein, wherein the identity of the at least about six epitopes is used to identify the test protein.

19. A method of determining protein characteristics, the method comprising:

obtaining a substrate in which portions of one or more proteins are conjugated to the substrate such that each individual (at the molecular level) protein portion has a unique, optically resolvable, spatial address;

applying a fluid containing a first through (ordered) nth set of one or more affinity reagents to the substrate, wherein each of the one or more affinity reagents is specific to one epitope (contiguous or non-contiguous amino acid sequence) of a portion of the one or more proteins, and wherein each affinity reagent of the first through nth set of one or more of affinity reagents is linked to an identifiable tag;

after each application to the substrate of the first and subsequent through nth set of one or more of affinity reagents, performing the following steps:

observing the identifiable tag;

identifying one or more unique spatial addresses of the substrate having one or more observed signal;

determining that each portion of the one or more proteins having an identified unique spatial address contains the one or more epitopes associated with the one or more observed signals; and determining the characteristics of each protein portion based on the one or more epitopes.

20. A method of determining protein characteristics, the method comprising:

obtaining a substrate in which portions of one or more proteins are conjugated to the substrate such that the substrate has a plurality of locations, each location comprising either a single protein, or a pool of proteins of which at least 60% of the proteins share the same amino acid sequence;

applying a fluid containing a first through (ordered) nth set of one or more affinity reagents to the substrate, wherein each of the one or more affinity reagents is specific to one epitope (contiguous or non-contiguous amino acid sequence) of a portion of the one or more proteins, and wherein each affinity reagent of the first through nth set of one or more of affinity reagents is linked to an identifiable tag;

after each application to the substrate of the first and subsequent through nth set of one or more of affinity reagents, performing the following steps:

observing the identifiable tag;

identifying one or more unique spatial addresses of the substrate having one or more observed signal;

determining that each portion of the one or more proteins having an identified unique spatial address contains the one or more epitopes associated with the one or more observed signals; and determining the characteristics of each protein portion based on the one or more epitopes.

21. The method of clause 19 or 20, wherein the method may be used to identify at least 400 different proteins at least 10% more quickly than techniques for protein identification that rely upon data from a mass spectrometer 22. The method of clause 21, wherein the method identifies the at least 400 different proteins with at least 50% accuracy.

23. The method of clause 22, wherein the method identifies a particular protein as a member of a particular family of proteins independent of whether the method identifies the particular protein itself within a threshold degree of confidence of more than 10%.

24. The method of clause 19 or 20, wherein the portions of one or more proteins are separated on the substrate based on the size of the protein.

25. The method of clause 19 or 20, wherein the portions of one or more proteins are separated on the substrate based on the charge of the protein.

26. The method of clause 19 or 20, wherein the substrate comprises microwells.

27. The method of clause 19 or 20, wherein the substrate comprises microwells of different sizes.

28. The method of clause 19 or 20, wherein the proteins are attached to the substrate via a biotin attachment.

29. The method of clause 19 or 20, wherein the proteins are attached to the substrate via a nucleic acid.

30. The method of clause 29, wherein the proteins are attached to the substrate via a nucleic acid nanoball.

31. The method of clause 19 or 20, wherein the proteins are attached to the substrate via a nanobead.

32. The method of clause 19 or 20, wherein obtaining the substrate in which portions of one or more proteins are bound comprises obtaining a substrate with an ordered array of functional groups and applying a protein sample such that each functional group conjugates to no more than one protein molecule from the sample.

33. The method of clause 32, wherein obtaining a substrate with an ordered array of functional groups comprises using a method selected from the group consisting of photolithography, Dip-Pen nanolithography, nanoimprint lithography, nanosphere lithography, thermal scanning probe lithography, local oxidation nanolithography, molecular self-assembly, stencil lithography, and electron-beam lithography.

34. The method of clause 32, wherein each functional group is located at least about 300 nm apart from each other functional group.

35. The method of clause 19 or 20, wherein the substrate comprises an ordered array of microwells of different sizes.

36. The method of clause 19 or 20, wherein obtaining the substrate comprises conjugating a first sample of proteins to the substrate, using a protein dye to detect each location with a bound protein from the first sample, conjugating a second sample, and using a protein dye to detect each location with a bound protein from the second sample.

37. The method of clause 19 or 20, wherein obtaining the substrate comprises conjugating a first sample of proteins to the substrate, using a protein dye to detect each location with a bound protein from the first sample, determining from the number of bound proteins the fraction of functional groups on the substrate which are not bound by a protein.

38. The method of clause 19 or 20, wherein an affinity reagent may comprise a pool of components which bind the same core sequence with different flanking sequences, such that at least one component has a binding affinity above a threshold for binding any instance of the core sequence regardless of flanking sequence.

What is claimed is:

1. A method of assaying proteins, comprising:

(a) providing a plurality of full length protein molecules immobilized on a substrate at unique spatial addresses, the unique spatial addresses being immobilized to an individual full length protein molecule of the plurality of full length protein molecules, wherein each unique spatial address is optically resolvable from each other unique spatial address on the substrate;

(b) binding composite affinity reagents to full length protein molecules of the plurality of full length protein molecules immobilized on the substrate, wherein each individual composite affinity reagent of the composite affinity reagents comprises a linker that is attached to a plurality of antibodies or fragments thereof and a common identifiable tag, and wherein each composite affinity reagent recognizes two or more differing full length the different protein molecules of the plurality of full length protein molecules;

(c) detecting signals from unique spatial addresses containing the immobilized full length protein molecules that are bound to the composite affinity reagents;

(d) repeating steps (b) and (c) using different composite affinity reagents; and (e) detecting a binding pattern comprising presences or absences of signals from each of the different composite affinity reagents bound to the immobilized full length protein molecules at the unique spatial addresses on the substrate.

2. The method of claim 1, wherein step (e) further comprises determining for each of the unique spatial addresses:

(i) a set of the different composite affinity reagents that bind to the individual full length protein molecule at the unique spatial address, and (ii) a set of the different composite affinity reagents that do not bind to the individual full length protein molecule at the unique spatial address.

3. The method of claim 1, wherein the substrate comprises beads.

4. The method of claim 1, wherein full length protein molecules of the plurality of full length protein molecules are immobilized to the substrate via nucleic acids.

5. The method of claim 1, wherein the signals are produced by fluorescent tags.

6. The method of claim 1, wherein the composite affinity reagents bind to amino acids comprising post translational modifications.

7. The method of claim 1, further comprising treating the plurality of full length protein molecules to remove the post translational modifications.

8. The method of claim 1, wherein the plurality of full length protein molecules comprises more than 1000 different full length protein molecules.

9. The method of claim 1, wherein the different composite affinity reagents have a known degree of non-specificity and known specificity for the full length protein molecules of the plurality of full length protein molecules.

10. The method of claim 1, further comprising: (f) assigning a protein identity to the full length protein molecules of the plurality of full length protein molecules based upon the binding pattern of the composite affinity reagents at the unique spatial addresses on the substrate.

11. The method of claim 10, wherein a number of full length protein molecules identified in step (f) is greater than the quantity of composite affinity reagents to which the plurality of full length protein molecules is exposed.

12. The method of claim 10, wherein the assigning of step (f) comprises executing software on a computer processor to assign a probable protein identity to each of the unique spatial addresses and a confidence for the protein identity.

13. The method of claim 12, wherein the software comprises a machine learning algorithm trained using binding characteristics of the composite affinity reagents as inputs.

14. The method of claim 10, wherein the assigning of step (f) comprises executing software on a computer processor to perform a Bayesian inference using as inputs:

(i) known binding properties of the composite affinity reagents, (ii) the binding pattern at each of the unique spatial addresses, and (iii) a database of the plurality of different proteins.

15. The method of claim 1, wherein antibodies or fragments thereof in the plurality of antibodies or fragments thereof may be of the same type.

16. The method of claim 1, wherein antibodies or fragments thereof in the plurality of antibodies or fragments thereof may be of the differing types.

17. The method of claim 1, wherein the linker comprises a nanoparticle that is attached to the common identifiable tag.

\* \* \* \* \*